(12) United States Patent
Holmström et al.

(10) Patent No.: US 12,600,940 B2
(45) Date of Patent: *Apr. 14, 2026

(54) STRAINS AND PROCESSES FOR SINGLE CELL PROTEIN OR BIOMASS PRODUCTION

(71) Applicant: Solar Foods Oyj, Vantaa (FI)

(72) Inventors: Sami Holmström, Espoo (FI); Juha-Pekka Pitkänen, Vantaa (FI)

(73) Assignee: Solar Foods Oyj, Vantaa (FI)

( * ) Notice: Subject to any disclaimer, the term of this patent is extended or adjusted under 35 U.S.C. 154(b) by 848 days.

This patent is subject to a terminal disclaimer.

(21) Appl. No.: 17/767,994

(22) PCT Filed: Oct. 22, 2020

(86) PCT No.: PCT/FI2020/050699
§ 371 (c)(1),
(2) Date: Apr. 11, 2022

(87) PCT Pub. No.: WO2021/084159
PCT Pub. Date: May 6, 2021

(65) Prior Publication Data
US 2024/0093141 A1     Mar. 21, 2024

(30) Foreign Application Priority Data
Oct. 29, 2019    (EP) ..................................... 19205786

(51) Int. Cl.
*C12N 1/20* (2006.01)
*A23L 33/135* (2016.01)
(Continued)

(52) U.S. Cl.
CPC ............ *C12N 1/205* (2021.05); *A23L 33/135* (2016.08); *C12N 15/52* (2013.01); *C12R 2001/01* (2021.05)

(58) Field of Classification Search
CPC .......... C12N 1/205; C12N 1/20; A23K 10/16; A23L 33/135; C12R 2001/01;
(Continued)

(56) References Cited

U.S. PATENT DOCUMENTS

2020/0165733 A1     5/2020   Reed et al.

FOREIGN PATENT DOCUMENTS

| CN | 109154006 A | 1/2019 | |
| JP | S6258989 | * 12/1991 | ........... A23L 33/135 |

(Continued)

OTHER PUBLICATIONS

Copeland et al., "Complete sequence of chromosome of Xanthobacter autotrophicus Py2." Submitted (Jul. 2007) to the EMBL/GenBank/DDBJ databases (Year: 2007).*

(Continued)

*Primary Examiner* — Jana A Hines
(74) *Attorney, Agent, or Firm* — Ziegler IP Law Group, LLC.

(57) ABSTRACT

A bacterial strain of the genus *Xanthobacter* and continuous culture processes for the production of protein or biomass using bacteria of the genus *Xanthobacter*, said process including supply of gases and minerals to the cells. The present disclosure also relates to the products of these processes and use of these products in e.g. food or feed. Reference is made to the Identification of the Microorganism, having the Identification reference given by the DEPOSITOR of SoF1 and with the Accession number given by the INTERNATIONAL DEPOSITORY AUTHORITY of VTT E-193585. The date of the original deposit is Jun. 11, 2019.

3 Claims, 2 Drawing Sheets

Specification includes a Sequence Listing.

(51) Int. Cl.

| | |
|---|---|
| *C12N 1/205* | (2026.01) |
| *C12N 15/52* | (2006.01) |
| *C12R 1/01* | (2006.01) |

(58) Field of Classification Search

CPC .......... A01G 18/20; C12P 13/00; Y02P 20/59; Y02E 50/30; C12M 35/08; C12M 23/58; C12M 41/12

See application file for complete search history.

(56) References Cited

FOREIGN PATENT DOCUMENTS

| | | | | |
|---|---|---|---|---|
| JP | S 6258989 A | * | 12/1991 | |
| JP | 2019517775 A | | 6/2019 | |
| RU | 2688486 C2 | | 5/2019 | |
| RU | 2765490 C2 | | 1/2022 | |
| RU | 2771261 C2 | | 4/2022 | |
| WO | 2013148348 A1 | | 10/2013 | |
| WO | 2015027209 A2 | | 2/2015 | |
| WO | WO-2017048773 A1 | * | 3/2017 | ............... C12P 7/02 |
| WO | 2017165244 A1 | | 9/2017 | |
| WO | 2018052295 A1 | | 3/2018 | |
| WO | WO-2018144965 A1 | * | 8/2018 | ............ A01G 18/20 |
| WO | 2018213568 A1 | | 11/2018 | |

OTHER PUBLICATIONS

Padden et al., (Intl J Systematic Bacteriology, Apr. 1997, vol. 47, No. 2,p. 394-401) (Year: 1997).*

T.G.Volova and V.A. Barashkov, Characteristics of Proteins Synthesized by Hydrogen-Oxidizing Microorganisms, Institute of Biophysics, Siberian Branch, Russian Academy of Sciences, Krasnoyarsk, 660036 Russia, Siberian Federal University, Krasnoyarsk, 660036 Russia, Sep. 17, 2000 (6 pages).

Padden, A.N., et al., "*Xanthobacter tagetidis* sp. nov., an organism associated with Tagetes species and able to grow on substituted thiphenes", Int. J. Syst. Bacteriol., vol. 47, No. 2, pp. 394-401, Apr. 1997 (Apr. 1997).

Canadian Intellectual Property Office, Canadian Office Action, Examination Search Report, Application No. 3153196, Jun. 8, 2023, 7 pages.

Croes, L.M., et al., "Regulation of methanol oxidation and carbon dioxide fixation in Xanthobacter strain 25a grown in continuous culture", Arch. Microbiol., vol. 155, pp. 159-163, 1991.

Genbank KF560403.1, 1447 bp DNA, from *Xanthobacter* sp. W31 16S ribosomal RNA gene, partial sequence, Aug. 20, 2013 (Aug. 20, 2013), retrieved May 18, 2023 (May 18, 2023) at: https://www.ncbi.nlm.nih.gov/nucleotide/KF560403.

Japanese Patent Office; Notification of Reasons for Refusal, Application No. 2022-519493, Date of Drafting Jun. 6, 2023, 6 pages.

Meijer, W.G., et al., "Characterization of Xanthobacter strains H4-14 and 25a and enzyme profiles after growth under autotrophic and heterotrophic conditions", Arch. Microbiol., vol. 153, pp. 360-367, 1990.

Wiegel, J., "The genus Xanthobacter", Chapter 3.1.15 in: Prokaryotes, vol. 5, pp. 290-314, DOI: 10.1007/0-387-30745-1_16, 2006.

Berekhtin 2007 = 2007. URL: https://www.geokniga.org/bookfiles/geokniga-kurs-mineralogiiuchebnoe-posobie-agbetehtin2008.pdf, last accessed on May 19, 2023.), 2 pages.

International Mineralogical Association, Commision of New Minerals, Nomenclature and Classification, The Wayback Machine— https://web.archive.org/web/20190401074106/http://cnmnc.main.jp/, 1 page.

The Federal Service for Intellectual Property, The Federal State Budgetary Institution, The Federal Institute of industrial property (FIPS), Application No. 2022110524/10 (022157), Office Action, May 22, 2023, 9 Pages.

Andersen et al., "Mutations Altering the Catalytic activity of a plant-type ribulose bisphosphate carboxylase/oxygenase in Alcaligenes Eutrophus" Biochimica et Biophysica Acta, General Subjects, Elsevier, Amsterdam, NL, vol. 585, No. 1, Jun. 1, 1979, ISSN: 0304-4165, DOI: 10.1016/0304-4165(79)90319-2, 12 pages.

International Search Report and Written Opinion of the International Searching Authority, European Patent Office, Application No. PCT/FI2020/050699, mailed Feb. 1, 2021, 16 pages.

Ohmiya K et al, "Application of Microbial Genes to Recalcitrant Biomass Utilization and Environmental Conservation" Journal of Bioscience and Bioengineering, vol. 95, No. 6, Jan. 1, 2003, 14 pages.

Yu Jian et al., "The energy efficiency of carbon dioxide fixation by a hydrogen-oxidizing bacterium" International Journal of Hydrogen Energy, Elsevier Science Publishes B.V., Barking, GB, vol. 38, No. 21, May 31, 2013 ISSN: 0360-3199 DOI: 10.1016/J.IJHYDENE. 2013.04.153, 8 pages.

Riemann et al., "The Native Bacterioplankton Community in the Central Baltic Sea is Influenced by Freshwater Bacterial Species", Applied and Enviornmental Microbiology, DOI: 10.1128/AEM. 01983-07, vol. 74, No. 2, Jan. 2008, 13 pages.

Korean Patent Office, Office Action Application No. 10-2022-7012566, mailed Feb. 29, 2024, 8 pages.

Van Den Bergh et al. "Fructosebisphosphatase Isoenzymes of teh Chemoautotroph Xanthobacter flavus" Journal of Bacteriology, vol. 177, No. 20, Oct. 1995, 5 pages.

Republic of Colombia, Office Action, Application No. NC2022/0003736, mailed May 20, 2024, 8 pages.

China National Intellectual Property Administration, First Office Action, Application No. 202080069118.3, mailed Nov. 1, 2023, 13 pages.

Chun et al. "Proposed minimal standards for the use of genome data for the taxonomy of prokaryotes" International Journal of Systematic and Evolutionary Microbiology, DOI: 10.1099/ijsem.0.002516, 2018, 6 pages.

Copeland et al. "Xanthobacter autotrophicus strain Py2 16S ribosomal RNA, partial sequence" National Center for Biotechnology Information, Jan. 28, 2013, 2 pages.

Fu Bo et al., "Isolation and Identification of Hydrogen-oxidizing Bacteria in Medicago sativa Rhizosphere" Chin J Appl Environ Biol, 2009, DOI: 10.3724/SP.J.1145.2009.00650, 5 pages. English Translation, 8 pages.

Jämsä et al. "Inactivation of poly(3-hydroxybutyrate) (PHB) biosynthesis in 'Knallgas' bacterium *Xanthobacter* sp. SoF1" AMB Express, https://doi.org/10.1186/s13568-023-01577-0, 2023, 11 pages.

Lee et al. "OrthoANI: An improved algorithm and software for calculating average nucleotied identity" International Journal of Systemic and Evolutionary Microbiology, 2016, DOI 10.1099/ijsem. 0.000760, 5 pages.

Nakamura et al., "Fed-Batch Culture of Nitrogen-Fixing Hydrogen Bacterium Xanthobacter-Autotophicus Strain Y38" Report of the Fermentation Research Institute, Issue 69, 1988, 4 pages.

Padden et al., "Chemolithoutotrophy and mixotrophy in the thiophene-2-carboxylic acid-utilizing Xanthobacter tagetidis" Arch Microbiol (1998), 8 pages.

Page et al., "Roary: rapid large-scale prokaryote pan genome analysis" Bioinformatics, 31(22) 2015, Advance Access Publication Date Jul. 20, 2015, 3 pages.

Seemann et al. "Prokka: rapid prokaryotic genome annotation" Bioinformatics, vol. 30, No. 14, 2014, doi: 10.1093/bioinformatics/but153, 2 pages.

Shively et al. "Something From Almost Nothing: Carbon Dioxide Fixation in Chemoautotrophs", Annu. rev. Micorbiol, 1998, 40 pages.

State Committee on Science and Technology of the Republic of Belarus, National Center of Intellectual Property, Office Action, Application No. a20220102, mailed Sep. 26, 2024, 3 pages.

Tikhonva et al. "Xanthobacter oligotrophicus strain BF-7S 16S ribosomal RNA gene, partial sequence" Ministry of Industry and Trade Russia, Mar. 1, 2022, 1 page.

Wang et al. "Isolation and identification of a strain of Yellow bacillus and degradation of phthalates" Biotechnology Bulletin, vol. 34 Issue 10, Jun. 27, 2016, 8 pages. English Translation, 17 pages.

(56)                    References Cited

OTHER PUBLICATIONS

Wick et al. "Unicycler: Resolving bacterial genome assemblies from short and long sequencing reads" PLOS Computational Biology, Published Jun. 8, 2017, https://doi.org/10.1371/journal.pcbi. 1005595, 22 pages.

Yarza et al. "Aquabacter spiritensis strain SPL-1 16S ribosomal RNA, partial sequence" Syst Appl. Microbiol. 36 (1),, 2013, 2 pages.

* cited by examiner

STRAINS AND PROCESSES FOR SINGLE CELL PROTEIN OR BIOMASS PRODUCTION

FIELD OF THE INVENTION

The present invention relates to the production of protein and/or other macromolecules using microorganisms. In particular, the invention relates to novel bacterial strains and continuous culture processes for the production of protein or biomass using bacteria wherein gases and minerals are supplied to the cells. The invention also relates to the products of these processes and use of these products in e.g. food or feed.

BACKGROUND OF THE INVENTION

Growing world population, climate change and shortage of water increasingly pose a threat to traditional agriculture and thus sufficient supply of food and feed. Therefore, alternative sources of organic molecules, such as proteins, are being investigated. A potential alternative is single cell production, i.e. the production of protein and/or other macromolecules using microorganisms.

Chemoautotrophic microorganisms have been described which are able to grow on minimal mineral medium with hydrogen gas as the energy source and carbon dioxide as the only carbon source. For a review of these microorganisms, see e.g. Shively et al. (1998) Annu Rev Microbiol 52:191. Patent application WO2018144965 describes various microorganisms and bioprocesses for converting gaseous substrates into high-protein biomass. Andersen et al. (1979) Biochim Biophys Acta 585:1-11 describes mutant strains of *Alcaligenes eutrophus*, a hydrogen bacterium that grows readily under heterotrophic and autotrophic conditions. Mutants having altered ribulose-1,5-bisphosphate carboxylase/oxygenase (rubisco) activity were characterised. Ohmiya et al. (2003) J. Biosci. Bioeng. 95:549-561 reviews the application of microbial genes to recalcitrant biomass utilization. Yu Jian et al. (2013) Int J Hydrogen Ener 38:8683-8690 describes carbon dioxide fixation by a hydrogen-oxidizing bacterial isolate. A high energy efficiency of 50% was measured under a moderate oxygen concentration (10 mol %).

However, various chemoautotrophic microorganisms have different properties in terms of growth rate, yield, biomass composition as well as properties related to being used as a food ingredient such as safety in human consumption, taste, smell, mouth-feel, technical and functional properties in cooking, etc. Not every chemoautotrophic microorganism has sufficient growth rate and provides sufficient yield and not every process can realistically be upscaled to an economically viable large-scale process. In order to have sufficient output of functional protein, e.g. for food or feed applications, it is important to find a suitable production organism and a suitable process which can be performed at large scale. This need is addressed by the present invention.

SUMMARY OF THE INVENTION

In a first main aspect, the invention relates to an isolated bacterial strain VTT-E-193585 or a derivative thereof.

In further aspects, the invention relates to a culture comprising the bacterial strain of the invention or derivative thereof. Furthermore, the invention relates to a process for the production of biomass and/or protein, said process comprising culturing the bacterial strain of the invention or a derivative thereof.

In a further aspect, the invention relates to a process for the production of biomass and/or protein, said process comprising culturing a bacterial strain of the genus *Xanthobacter* in continuous culture with hydrogen as energy source and an inorganic carbon source, wherein the inorganic carbon source comprises carbon dioxide.

In further main aspects, the invention relates to bulk protein, biomass or non-protein cellular or chemical components obtained or obtainable by the process of the invention, and to a food or feed product obtained or obtainable by a process of the invention.

DETAILED DESCRIPTION OF THE INVENTION

Definitions

Figure 1:
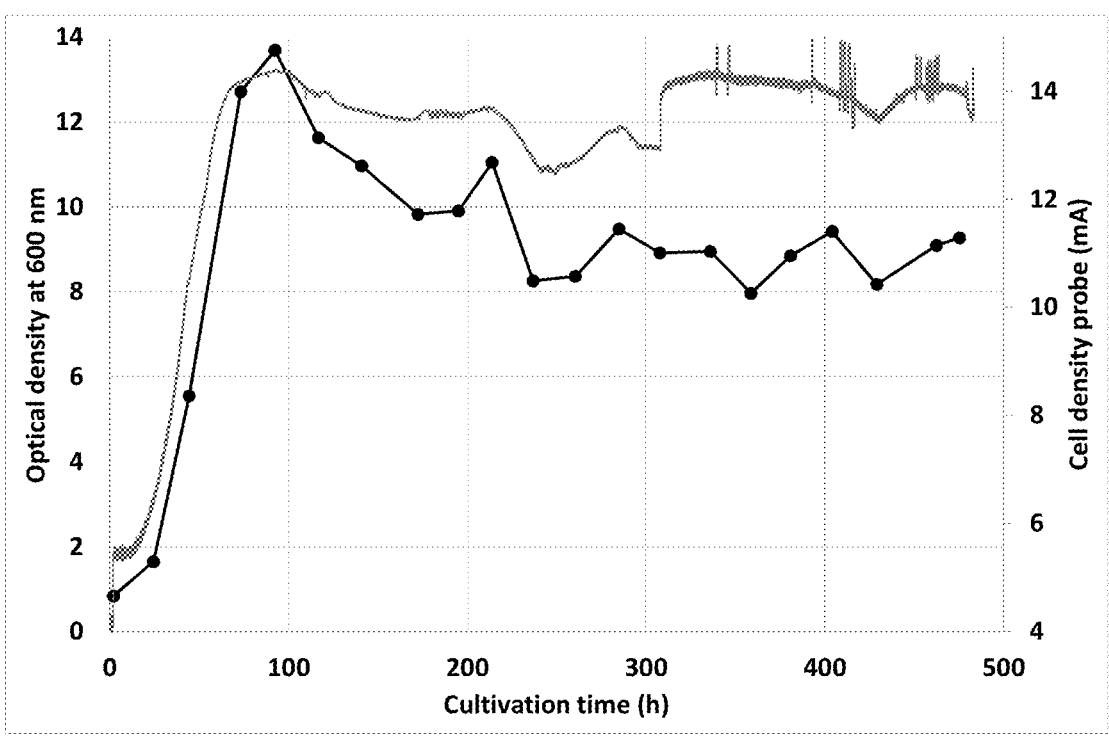
FIG. 1. Optical density measured at 600 nm (black circles) and optical density probe readings during chemoautotrophic 200-L cultivation of isolated bacterial strain deposited as VTT-E-193585.

When used herein, the term "isolated", e.g. in the context of a strain, means isolated from its natural environment. Preferably, an isolated strain is pure, i.e. free of other strains.

The term "derivative", when used herein in the context of a strain, refers to a strain which is derived from a reference strain, i.e. generated using the reference strain as starting point. E.g. a genetically-engineered or otherwise mutated or genetically-modified strain is an embodiment of such a derivative. Genetic modifications include point mutations, as well as insertions or deletions, including insertions or deletions of entire loci or fragments thereof. The derivative preferably has fewer than 10 genetic modifications, e.g. fewer than 5, such as 4, 3, 2 or 1 genetic modification(s) compared to the reference strain.

When used herein, the noun "culture" refers to a suspension of viable cells in a liquid medium.

The term "biomass" has its usual meaning in the field of bacterial fermentation and refers to cellular material.

The term "continuous culture", when used herein, refers to a culturing process wherein fresh media is added continuously to the culture and media with bacterial culture is removed continuously at essentially the same rate.

ASPECTS AND EMBODIMENTS OF THE INVENTION

In a first main aspect, the invention relates to an isolated bacterial strain VTT-E-193585 or a derivative thereof.

Strain VTT-E-193585 has been isolated from the seashore of the Baltic sea in Naantali, Finland. This organism is able to grow in suitable bioreactor conditions with minimal mineral medium with hydrogen as the energy source and carbon dioxide as the carbon source at limited oxygen conditions. 16S sequencing and Illumina metagenomics sequencing have shown that the strain most likely is a member of the genus *Xanthobacter*, but is not a known species. The bacterial strain is highly suitable for food and feed applications, because the dried cell powder has a high protein content and contains all the essential amino acids. It also contains more unsaturated than saturated fatty acids and a high level of B-group vitamins. The levels of peptidoglycans and lipopolysaccharides, which may cause allergy or toxicity, are low. A toxicity analysis was performed and no genotoxicity or cytotoxicity was observed for the strain. In addition, the strain is generally sensitive to antibiotics.

Strain VTT-E-193585 (SoF1) has been deposited on Jun. 11, 2019 in the VTT Culture Collection at the VTT Technical Research Centre of Finland, P.O. Box 1000, FI-02044 VTT, Finland, an International Depositary Authority under the Budapest Treaty. Further information on the characteristics of the strain and methods for culturing the strain are provided in the Examples herein.

In a preferred embodiment, if the strain is a derivative of strain VTT-E-193585, the derivative has retained the ability to grow using hydrogen gas as energy source and carbon dioxide as the only carbon source.

In one embodiment, if the strain is a derivative of strain VTT-E-193585, the derivative comprises the 16S ribosomal RNA set forth in SEQ ID NO:1 or a 16S ribosomal RNA having up to 20 nucleotide differences with SEQ ID NO:1, e.g. 1 to 10, such as 1 to 5, e.g. one, two or three nucleotide differences with SEQ ID NO: 1.

```
16S ribosomal RNA sequence of strain
VTT-E-193585:
                                        SEQ ID NO: 1
CTTGAGAGTTTGATCCTGGCTCAGAGCGAACGCTGGCGGCAGGCCT

AACACATGCAAGTCGAGCGCCCAGCAATGGGAGCGGCAGACGGGT

GAGTAACGCGTGGGGATGTGCCCAATGGTACGGAATAACCCAGGG

AAACTTGGACTAATACCGTATGAGCCCTTCGGGGGAAAGATTTAT

CGCCATTGGATCAACCCGCGTCTGATTAGCTAGTTGGTGGGGTAA

CGGCCCACCAAGGCGACGATCAGTAGCTGGTCTGAGAGGATGATC

AGCCACACTGGGACTGAGACACGGCCCAGACTCCTACGGGAGGCA

GCAGTGGGGAATATTGGACAATGGGCGCAAGCCTGATCCAGCCAT

GCCGCGTGTGTGATGAAGGCCTTAGGGTTGTAAAGCACTTTCGCC

GGTGAAGATAATGACGGTAACCGGAGAAGAAGCCCCGGCTAACTT

CGTGCCAGCAGCCGCGGTAATACGAAGGGGGCTAGCGTTGCTCGG

AATCACTGGGCGTAAAGCGCACGTAGGCGGATCGTTAAGTCAGGG

GTGAAATCCTGGAGCTCAACTCCAGAACTGCCCTTGATACTGGCG

ACCTTGAGTTCGAGAGAGGTTGGTGGAACTGCGAGTGTAGAGGTG

AAATTCGTAGATATTCGCAAGAACACCAGTGGCGAAGGCGGCCAA

CTGGCTCGATACTGACGCTGAGGTGCGAAAGCGTGGGGAGCAAAC

AGGATTAGATACCCTGGTAGTCCACGCCGTAAACGATGGATGCTA

GCCGTTGGGCAGCTTGCTGTTCAGTGGCGCAGCTAACGCATTAAG

CATCCCGCCTGGGGAGTACGGTCGCAAGATTAAAACTCAAAGGAA

TTGACGGGGGCCCGCACAAGCGGTGGAGCATGTGGTTTAATTCGA

AGCAACGCGCAGAACCTTACCAGCCTTTGACATGGCAGGACGATT

TCCAGAGATGGATCTCTTCCAGCAATGGACCTGCACACAGGTGCT
```

4

```
                    -continued
GCATGGCTGTCGTCAGCTCGTGTCGTGAGATGTTGGGTTAAGTCC

CGCAACGAGCGCAACCCTCGCCTCTAGTTGCCAGCATTCAGTTGG

GCACTCTAGAGGGACTGCCGGTGATAAGCCGAGAGGAAGGTGGGG

ATGACGTCAAGTCCTCATGGCCCTTACGGGCTGGGCTACACACGT

GCTACAATGGTGGTGACAGTGGGATGCGAAAGGGCGACCTCTAGC

AAATCTCCAAAAGCCATCTCAGTTCGGATTGTACTCTGCAACTCG

AGTGCATGAAGTTGGAATCGCTAGTAATCGTGGATCAGCATGCCA

CGGTGAATACGTTCCCGGGCCTTGTACACACCGCCCGTCACACCA

TGGGAGTTGGCTTTACCCGAAGGCGCTGCGCTAACCCGCAAGGGA

GGCAGGCGACCACGGTAGGGTCAGCGACTGGGGTGAAGTCGTAAC

AAGGTAGCCGTAGGGGAACCTGCGGCTGGATCACCTCCTTT.
```

In a further aspect, the invention relates to a culture comprising the bacterial strain of the invention or derivative thereof. In a preferred embodiment, the volume of the culture is 100 mL or more, e.g. 1 L or more, such as 10 L or more, e.g. 1,000 L or more, such as 10,000 L or more, e.g. 50,000 L or more, such as 100,000 L or more, e.g. 200,000 L or more.

In a further aspect, the invention relates to a process for the production of biomass and/or protein, said process comprising culturing the bacterial strain of the invention or a derivative thereof. In one embodiment, the process is for the production of biomass. In another embodiment, the process is for the production of protein. In one embodiment, the process comprises culturing the strain in continuous culture with hydrogen as energy source and an inorganic carbon source, wherein the inorganic carbon source comprises carbon dioxide. In a further embodiment, the process is for the production of biomass and comprises culturing the strain in continuous culture with hydrogen as energy source and an inorganic carbon source, wherein the inorganic carbon source comprises carbon dioxide. Various further embodiments of the process are described herein below.

In a further main aspect, the invention relates to a process for the production of biomass and/or protein, said process comprising culturing a bacterial strain of the genus *Xanthobacter* in continuous culture with hydrogen as energy source and an inorganic carbon source, wherein the inorganic carbon source comprises carbon dioxide. In one embodiment, the process is for the production of biomass. In another embodiment, the process is for the production of protein. Various further embodiments of the process are described herein below.

According to the genome sequence, the strain deposited under number VTT-E-193585 uses most likely Calvin-Benson-Bassham cycle for the carbon fixation where carbon dioxide molecule is connected to 5-carbon chain of ribulose 1,5-bisphosphate forming two molecules of glycerate 3-phosphate. This enables the strain to synthesise all the other organic molecules it requires for growth. Energy from hydrogen comes into the cell most likely through $NAD^+$-reducing hydrogenases and/or NiFeSe-hydrogenases. In essence that is a redox reaction where hydrogen $(H_2)$ is oxidized to $H^+$ and $NAD^+$ is reduced to NADH. In addition to ATP, NADH is one of the main energy carriers inside living organisms. Alternatively, some other energy equivalent is reduced by another hydrogenase enzyme using $H_2$. The Calvin-Benson-Bassham cycle requires energy in the form of ATP and NADH/NADPH in order to fix $CO_2$. The strain most likely generates ATP through oxidative phosphorylation, which consists of four protein complexes generating a proton gradient across a membrane. The proton gradient is generated using mainly energy from NADH. The proton gradient drives the ATP synthase complex generating ATP. According to the genome sequence, the strain has a bacterial F-type ATP synthase.

It is to be understood, when it is specified that the process comprises culturing the strain with an inorganic carbon source, that the inorganic carbon source is the main carbon source in the culture. Thus, there may be minor amounts of organic carbon sources present in the culture, but the main metabolism and growth of the culture is based on the utilisation of the inorganic carbon source, preferably carbon dioxide, as carbon source. Preferably the proportion of the carbon supplied to the culture that is organic is less than 5%, such as less than 1%, e.g. less than 0.1% of all carbon supplied to the culture during the process. Preferably, no organic carbon sources are supplied to the process.

Similarly, it is to be understood, when it is specified that the process comprises culturing the strain with hydrogen ($H_2$) as energy source, that hydrogen is the main energy source in the culture. Thus, there may be other minor energy sources present in the culture such as ammonia, which may be supplied as nitrogen source, or minor amounts of organic compounds, but the main metabolism and growth of the culture is based on the utilisation of hydrogen as energy source. In the overall process hydrogen is preferably produced by water electrolysis; i.e. by splitting water with electricity to hydrogen and oxygen gases. Thus, the hydrogen and oxygen gases are provided to the bioreactor from an electrolyser nearby. Alternatively, electrodes may be placed inside the bioreactor to produce hydrogen and oxygen in the bioreactor rather than in a separate electrolyser.

The inorganic carbon source comprising carbon dioxide may comprise other inorganic carbon sources, such as e.g. carbon monoxide. In one embodiment, only carbon sources in gaseous form are provided to the culture. In a preferred embodiment, carbon dioxide is the only inorganic carbon source, and indeed the only carbon source, provided to the culture. In one embodiment, only gases and minerals are provided to the culture and the level of carbon dioxide in the gas provided is between 10% and 50%, e.g. between 15% and 45%, such as between 20% and 40%, e.g. between 25% and 35%, such as between 26% and 30%.

In another embodiment, gases and minerals are provided to the culture and the level of hydrogen ($H_2$) in the gas provided is between 30% and 80%, e.g. between 35% and 75%, such as between 40% and 70%, e.g. between 45% and 65%, such as between 50% and 60%.

In another embodiment, gases and minerals are provided to the culture and the level of oxygen ($O_2$) in the gas provided is between 10% and 25%, e.g. between 15% and 20%, such as between 16% and 18%. In another embodiment, the level of oxygen provided is such that the level of dissolved oxygen in the culture is maintained at between 5% and 10%.

In a preferred embodiment, only gases and minerals are provided to the culture and the gas provided comprising $H_2$, $CO_2$ and $O_2$, wherein the percentage of $H_2$ is between 40% and 70%, the percentage of $CO_2$ is between 18% and 28% and the percentage of $O_2$ is between 12% and 22%.

Typically, the process of the invention includes the addition of a nitrogen source. The nitrogen source may for example be provided in the form of ammonium hydroxide, an ammonium salt, such as ammonium sulphate or ammonium chloride, ammonia, urea or nitrate, e.g. potassium nitrate. In other embodiments, nitrogen gas ($N_2$) is provided as nitrogen source. In a preferred embodiment, the nitrogen source is ammonium hydroxide or an ammonium salt, such as ammonium sulphate.

In one embodiment, the nitrogen source provided is ammonium hydroxide at a concentration of between 100 mg/L and 10 g/L, such as between 250 mg/L and 4 g/L, e.g. between 0.5 g/L and 2 g/L, such as between 0.75 g/L and 1.5 g/L.

Typically, the process of the invention includes the addition of minerals, such as minerals containing ammonium, phosphate, potassium, sodium, vanadium, iron, sulphate, magnesium, calcium, molybdenum, manganese, boron, zinc, cobalt, selenium, iodine, copper and/or nickel. Suitable mineral media are well-known art, and have e.g. been described in *Thermophilic Bacteria*, CRC Press, Boca Raton, FL, Jacob K. Kristjansson, ed., 1992, for example on page 87, Table 4.

In one embodiment, the minerals added include one or more of the following: ammonia, ammonium (e.g., ammonium chloride ($NH_4Cl$), ammonium sulphate (($NH_4)_2SO_4$)), nitrate (e.g., potassium nitrate ($KNO_3$)), urea or an organic nitrogen source; phosphate (e.g., disodium phosphate ($Na_2HPO_4$), potassium phosphate ($KH_2PO_4$), phosphoric acid ($H_3PO_4$), potassium dithiophosphate ($K_3PS_2O_2$), potassium orthophosphate ($K_3PO_4$), disodium phosphate ($Na_2HPO_4 \cdot 2H_2O$) dipotassium phosphate ($K_2HPO_4$) or monopotassium phosphate ($KH_2PO_4$); sulphate; yeast extract; chelated iron (chelated e.g. with EDTA or citric acid); potassium (e.g., potassium phosphate ($KH_2PO_4$), potassium nitrate ($KNO_3$), potassium iodide ($KI$), potassium bromide ($KBr$)); and other inorganic salts, minerals, and trace nutrients (e.g., sodium chloride ($NaCl$), magnesium sulphate ($MgSO_4 \cdot 7H_2O$) or magnesium chloride ($MgCl_2$), calcium chloride ($CaCl_2$), calcium sulphate ($CaSO_4$) or calcium carbonate ($CaCO_3$), manganese sulphate ($MnSO_4 \cdot 7H_2O$) or manganese chloride ($MnCl_2$), ferric chloride ($FeCl_2$), ferrous sulphate ($FeSO_4 \ 7H_2O$) or ferrous chloride ($FeCl_2 \ 4H_2O$), sodium bicarbonate ($NaHCO_3$) or sodium carbonate ($Na_2CO_3$), zinc sulphate ($ZnSO_4$) or zinc chloride ($ZnCl_2$), ammonium molybdate ($NH_4MoO_4$) or sodium molybdate ($Na_2MoO_4 \cdot 2H_2O$), cuprous sulphate ($CuSO4$) or copper chloride ($CuCl_2 \cdot 2H_2O$), cobalt chloride ($CoCl_2 \cdot 6H_2O$) or cobalt sulphate ($CoSO_4$), aluminium chloride ($AlCl_3 \cdot 6H_2O$), lithium chloride ($LiCl$), boric acid ($H_3BO_3$), nickel chloride $NiCl_2 \cdot 6H_2O$) or nickel sulphate ($NiSO_4$), tin chloride ($SnCl_2 \cdot H_2O$), barium chloride ($BaCl_2 \cdot 2H_2O$), copper selenate ($CuSeO_4 \ 5H_2O$), sodium selenate ($Na_2SeO_4$) or sodium selenite ($Na_2SeO_3$), sodium metavanadate ($NaVO_3$), chromium salts).

In a preferred embodiment, the process of the invention includes the addition of one, more or all of: $NH_4OH$, $KH_2PO_4$, $Na_2HPO_4 \cdot 2H_2O$, $NaVO_3 \cdot H_2O$, $FeSO_4 x7H_2O$, $MgSO_4 \cdot 7H_2O$, $CaSO_4$, $Na_2MoO_4 \cdot 2H_2O$, $MnSO_4 \cdot 7H_2O$, $ZnSO_4 \cdot 7H_2O$, $H_3BO_3$, $CoSO_4$, $CuSO_4$, $NiSO_4$.

In one embodiment, the medium provided to the cells comprises less than 1 g/L of chloride salts, such as less than 0.25 g/L of chloride salts, e.g. less than 0.1 g/L of chloride salts, such as less than 0.025 g/L of chloride salts, e.g. less than 0.01 g/L of chloride. In one embodiment, no chloride salts are supplied to the culture.

In another embodiment, no vitamins are supplied during the process, i.e. the media provided to the culture does not contain vitamins.

In another embodiment, no amino acids are supplied during the process, i.e. the media provided to the culture does not contain amino acids.

In another embodiment, no organic compounds are supplied during the process, i.e. the media provided to the culture does not contain any organic compounds.

In certain embodiments, the pH of the bacterial culture is controlled at a certain level. In certain embodiments, pH is controlled within an optimal range for bacterial maintenance and/or growth and/or production of organic compounds. In one embodiment, the pH in the culture is maintained between 5.5 and 8.0, e.g. between 6.5 and 7.0, such as at 6.8.

In certain embodiments, the temperature of the bacterial culture is controlled. In certain embodiments, temperature is controlled within an optimal range for bacterial maintenance and/or growth and/or production of organic compounds. In one embodiment, the culture is grown at a temperature between 25° C. and 40° C., e.g. between 28° C. and 32° C., such as at 30° C.

Typically, the process of the invention is carried out in a bioreactor. A bioreactor is utilized for the cultivation of cells, which may be maintained at particular phases in their growth curve. The use of bioreactors is advantageous in many ways for cultivating chemoautotrophic growth. Generally, the control of growth conditions, including control of dissolved carbon dioxide, oxygen, and other gases such as hydrogen, as well as other dissolved nutrients, trace elements, temperature and pH, is facilitated in a bioreactor. Nutrient media, as well as gases, can be added to the bioreactor as either a batch addition, or periodically, or in response to a detected depletion or programmed set point, or continuously while the period the culture is grown and/or maintained. In a continuous culture process, nutrient media, as well as gases, are added to the bioreactor continuously. Furthermore, bacteria-containing medium is being removed from the bioreactor continuously.

In a preferred embodiment, the volume of the bacterial culture is 100 mL or more, such as 1 L or more, e.g. 10 L or more, such as 100 L or more, e.g. 1,000 L or more, such as 10,000 L or more, e.g. 50,000 L or more, such as 100,000 L or more, e.g. 200,000 L or more.

In one embodiment, the productivity of the culture is more than 0.1 g cell dry weight per liter per hour, such as more than 0.2, e.g. more than 0.3, such as more than 0.4, e.g. more than 0.5, such as more than 0.6, e.g. more than 0.7, such as more than 0.8, e.g. more than 0.9, such as more than 1 g per liter per hour.

Bacteria can be inoculated directly from a cell bank, or via a seed culture at a smaller scale. Preferably, supply of fresh media to the culture and removal of used up media with bacteria is occurring at the same rate, such that the volume in the bioreactor remains the same.

In one embodiment, after an initial phase of reaching a suitable cell density, the bacteria grow at steady state or pseudo steady state, remaining continuously in their log phase, at an OD600 above 5, such as above 10, e.g. above 20, such as between 50 and 200, e.g. between 50 and 100.

In one embodiment of the process of the invention, the bacterial strain has a growth rate of 0.04-0.12 h$^{-1}$.

In another embodiment of the process of the invention, the liquid feed rate in the continuous phase is 50-80% of the growth rate.

*Xanthobacter* is a genus of Gram-negative bacteria from the Xanthobacteraceae family.

In one embodiment, the *Xanthobacter* strain used in the process of the invention is a strain which uses the Calvin Benson Bassham pathway to convert carbon dioxide into organic compounds, e.g. glucose, essential for living organisms.

In one embodiment, the *Xanthobacter* strain used in the process of the invention is a strain which uses NiFeSe-hydrogenases for converting hydrogen (H$_2$) into cellular energy equivalents.

In one embodiment, the *Xanthobacter* strain used in the process of the invention is a strain which uses NAD$^+$-reducing hydrogenases for converting hydrogen (H$_2$) into cellular energy equivalents.

In one embodiment, the *Xanthobacter* strain used in the process of the invention capable of nitrogen fixation.

In one embodiment, the bacterial strain used in the process of the invention is selected from the group consisting of: *X. agilis*, *X. aminoxidans*, *X. autotrophicus*, *X. flavus*, *X. tagetidis*, *X. viscosus*, *Xanthobacter* sp. 126, *Xanthobacter* sp. 91 and strain VTT-E-193585.

In a preferred embodiment, the bacterial strain used in the process of the invention is VTT-E-193585 or *X. tagetidis*. Most preferably the strain used in the process of the invention is VTT-E-193585.

In another embodiment, the bacterial strain used in the process of the invention comprises the 16S ribosomal RNA set forth in SEQ ID NO:1 or a 16S ribosomal RNA having up to 20 nucleotide differences with SEQ ID NO:1, e.g. 1 to 10, such as 1 to 5, e.g. one, two or three nucleotide differences with SEQ ID NO: 1.

In another embodiment, the bacterial strain used in the process of the invention comprises a gene encoding a ribulose-1,5-bisphosphate carboxylase/oxygenase (rubisco) large chain having the sequence set forth in SEQ ID NO:3 or a sequence having more than more than 93% identity, e.g. more than 95% identity, such as more than 96% identity, e.g. more than 97% identity, such as more than 98% identity, e.g. more than 99% sequence identity to the sequence set forth in SEQ ID NO:3.

In another embodiment, the bacterial strain used in the process of the invention comprises a gene encoding a ribulose-1,5-bisphosphate carboxylase/oxygenase (rubisco) small chain having the sequence set forth in SEQ ID NO:5 or a sequence having more than 83% sequence identity, e.g. more than 86%, identity such as more than 90% identity, e.g. more than 95% identity, such as more than 96% identity, e.g. more than 97% identity, such as more than 98% identity, e.g. more than 99% sequence identity to the sequence set forth in SEQ ID NO:5.

```
SEQ ID NO: 2:
Nucleotide sequence of Ribulose
bisphosphate carboxylase large chain:
ATGGGTGCCGAAGCAACCGTCGGGCAGATCACGGACGCCAAGAAG

AGATACGCCGCCGGCGTGCTGAAGTACGCCCAGATGGGCTACTGG

AACGGCGACTACGTTCCCAAGGACACCGACCTCCTGGCGGTGTTC

CGCATCACCCCCCAGGCGGGCGTGGACCCGGTGGAAGCCGCCGCG

GCGGTCGCCGGCGAAAGCTCCACCGCTACCTGGACCGTGGTGTGG

ACCGACCGGCTCACCGCCGCCGACGTCTACCGCGCCAAGGCCTAC

AAGGTGGAGCCGGTGCCGGGCCAGGAAGGCCAGTATTTCTGCTAC

ATCGCCTATGATCTCGATTTGTTCGAGGAAGGCTCCATCGCCAAC

CTCACGGCCGTCGATCATCGGCAACGTCTTCTCCTTCAAGCCGCTG

AAGGCGGCGCGGCTGGAGGACATGCGGCTTCCCGTCGCCTATGTG

AAGACCTTCCGCGGCCCGCCCACCGGCATCGTGGTCGAGCGCGAG
```

-continued

```
CGCCTGGACAAGTTCGGCCGCCCCCTTCTGGGCGCCACCACCAAG

CCGAAGCTTGGCCTCTCGGGCAAGAATTACGGCCGCGTGGTCTAT

GAGGCCCTCAAGGGCGGCCTCGACTTCGTGAAGGACGACGAGAAC

ATCAACTCGCAGCCCTTCATGCACTGGCGCGATCGCTTCCTCTAT

TGCATGGAGGCCGTCAACAAGGCCCAGGCCGAGACCGGCGAGGTG

AAGGGGCACTATCTCAACATCACCGCCGGGACCATGGAGGAGATG

TACCGCCGCGCCGAGTTCGCCAAGGAACTGGGCTCCGTGGTGGTG

ATGGTGGATCTCATCATCGGCTGGACCGCCATCCAGTCCATGTCC

AACTGGTGCCGCGAGAACGACATGATCCTGCACATGCACCGTGCG

GGCCATGGCACCTACACGCGCCAGAAGAGCCACGGCGTCTCCTTC

CGCGTCATCGCCAAGTGGCTGCGGCTCGCCGGCGTCGACCACCTG

CACACCGGCACCGCCGTGGGCAAGCTGGAAGGCGACCCCATGACC

GTGCAGGGCTTCTACAATGTCTGCCGCGAGACGACGACGCAGCAG

GACCTCACCCGCGGCCTGTTCTTCGAGCAGGACTGGGGCGGCATC

CGCAAGGTGATGCCGGTGGCCTCCGGCGGCATCCATGCGGGCCAG

ATGCACCAGCTCATCGACCTGTTCGGCGAGGACGTGGTGCTCCAG

TTCGGCGGCGGCACCATCGGCCACCCGGACGGCATCCAGGCCGGC

GCCACCGCCAACCGCGTGGCGCTGGAAACCATGATCCTCGCCCGC

AACGAGGGCCGCGACATCAGGAACGAGGGCCCGGAAATCCTGGTG

GAAGCCGCCAAATGGTGCCGTCCGCTGCGCGCGGCGCTCGATACC

TGGGGCGAGGTGACCTTCAACTACGCCTCCACCGACACGTCCGAT

TACGTGCCCACCGCGTCCGTCGCCTGA
```

SEQ ID NO: 3:
Amino acid sequence of Ribulose
bisphosphate carboxylase large chain
```
MGAEATVGQITDAKKRYAAGVLKYAQMGYWNGDYVPKDTDLLAVF

RITPQAGVDPVEAAAAVAGESSTATWTVVWTDRLTAADVYRAKAY

KVEPVPGQEGQYFCYIAYDLDLFEEGSIANLTASIIGNVFSFKPL

KAARLEDMRLPVAYVKTFRGPPTGIVVERERLDKFGRPLLGATTK

PKLGLSGKNYGRVVYEALKGGLDFVKDDENINSQPFMHWRDRFLY

CMEAVNKAQAETGEVKGHYLNITAGTMEEMYRRAEFAKELGSVVV

MVDLIIGWTAIQSMSNWCRENDMILHMHRAGHGTYTRQKSHGVSF

RVIAKWLRLAGVDHLHTGTAVGKLEGDPMTVQGFYNVCRETTTQQ

DLTRGLFFEQDWGGIRKVMPVASGGIHAGQMHQLIDLFGEDVVLQ

FGGGTIGHPDGIQAGATANRVALETMILARNEGRDIRNEGPEILV

EAAKWCRPLRAALDTWGEVTFNYASTDTSDYVPTASVA
```

SEQ ID NO: 4:
Nucleotide sequence of Ribulose
bisphosphate carboxylase small chain:
```
ATGCGCATCACCCAAGGCTCCTTCTCCTTCCTGCCGGACCTCACC

GACACGCAGATCAAGGCCCAGGTGCAATATTGCCTGGACCAGGGC

TGGGCGGTCTCGGTGGAGCACACCGACGATCCCCACCCGCGCAAC

ACCTATTGGGAGATGTGGGGCCCGCCCATGTTCGATCTGCGCGAC

GCGGCCGGCGTCTTCGGCGAGATCGAAGCCTGCCGGGCCGCCAAT
```

-continued

```
CCCGAGCATTATGTGCGGGTGAACGCCTTCGATTCCAGCCGCGGA

TGGGAGACGATCCGCCTGTCCTTCATCGTTCAGCGGCCCACCGTG

GAAGAGGGCTTCCGCCTCGACCGCACCGAAGGCAAGGGCCGCAAC

CAGAGCTACGCCATGCGCTACCGGGCGCAGTTCGCGCCGCGCTGA
```

SEQ ID NO: 5:
Amino acid sequence of Ribulose
bisphosphate carboxylase small chain:
```
MRITQGSFSFLPDLTDTQIKAQVQYCLDQGWAVSVEHTDDPHPRN

TYWEMWGPPMFDLRDAAGVFGEIEACRAANPEHYVRVNAFDSSRG

WETIRLSFIVQRPTVEEGFRLDRTEGKGRNQSYAMRYRAQFAPR
```

In another embodiment, the bacterial strain used in the process of the invention comprises a gene encoding a NAD$^+$-reducing hydrogenase HoxS subunit alpha having the sequence set forth in SEQ ID NO:7 or a sequence having more than 70% sequence identity, such as more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:7.

In another embodiment, the bacterial strain used in the process of the invention comprises a gene encoding a NAD$^+$-reducing hydrogenase HoxS subunit beta having the sequence set forth in SEQ ID NO:9 or a sequence having more than 77% sequence identity, such as more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:9.

In another embodiment, the bacterial strain used in the process of the invention comprises a gene encoding a NAD$^+$-reducing hydrogenase HoxS subunit gamma having the sequence set forth in SEQ ID NO: 11 or a sequence having more than 70% sequence identity, such as more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:11.

In another embodiment, the bacterial strain used in the process of the invention comprises a gene encoding a NAD$^+$-reducing hydrogenase HoxS subunit delta having the sequence set forth in SEQ ID NO: 13 or a sequence having more than 79% sequence identity, such as more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:13.

SEQ ID NO: 6:
Nucleotide sequence of NAD$^+$-
reducing hydrogenase HoxS subunit alpha:
```
ATGATGCCATCTGAGCCGCACGGCGCGGGCATGCCGCCCCCACGG

GAAGCGGCCGCGGTTCCCACCCCCCAGGAGGTGAGCGCGGTGGTG

GCCGAGGTGGTCGCGGATGCCGTGGCATCGGTGGGCGGCGCACGC

ACCCGGCTCATGGACATCGTCCAGCTGGCCCAGCAGCGTCTCGGC

CATCTCTCCGAAGAGACCATGGCGGCCATTGCCGCGCGGCTCGCC
```

-continued
```
ATTCCGCCGGTGGAAGTGGCGGACATGGTGTCCTTCTACGCCTTC

CTGAACCGCGCGCCCAAGGGCCGCTACCACATCCGCCTGTCGCGC

AGCCCCATCTCGCTGATGAAGGGCGCCGAGGCGGTGGCTGCCGCC

TTCTGCCAGATCCTCGGCATCGCCATGGGCGAGACCTCGCAGGAT

GGCGACTTCACCCTGGAATGGACCAACGACATCGGCATGGCCGAC

CAGGAGCCGGCCGCCCTCGTCAACGGCACGGTGATGACGCAGCTC

GCGCCCGGCGATGCGGCCATCATCGTCGGCCGGCTGCGGGCCCAT

CACGCGCCCAATGCCCTGCCGCTGTTCCCTGGAGCCGGCGTGGCC

GGCTCCGGCCTGCCCCATGCCCGGATCCGCCCCAGCCTGGTGATG

CCGGGACAGCTTCTGTTCCGCGAGGACCACACGACGCCGGGCGCC

GGCATCAAGGCGGCACTCGCCCTCACCCCGGACGAAGTGGTGCAG

AAGGTCTCCGCCGCGCGCCTGCGCGGGGGGGGTGGCGCCGGCTTT

CCCACCGGTCTCAAATGGAAGCTCTGCCGCCAGTCGCCCGCCACC

ACCCGCCATGTGATCTGCAATGCGGACGAGGGCGAGCCCGGCACC

TTCAAGGATCGCGTGCTGCTCACGCAGGCGCCGCACCTCATGTTC

GACGGCATGACCATCGCCGGCTACGCCTTGGGGGCGCGGGAGGGC

GTGGTCTATCTGCGCGGCGAGTACGCCTATCGTGGGAGCCTCTG

CATGCGGTCCTGCGCGAGCGCTATGGGCTCGGGCTCGCCGGCGCG

AACATCCTGGGACACGCGGGCTTCGACTTCGACATCCGCATCCAG

CTGGGCGCCGGCGCCTATATCTGCGGCGAGGAATCCGCGCTGGTG

GAATCGCTGGAAGGCAAGCGCGGCTCGCCCCGCGACCGCCCCCCC

TTCCCCACCGTGCGCGGCCATCTCCAGCAGCCCACCGCCGTGGAC

AATGTGGAGACCTTCGCCTGCGCCGCCCGCATCCTGGAGGATGGC

GTGGAGGCGTTCGCGGGCATCGGCACGCCCGAATCCGCCGGCACG

AAGCTCCTCTCGGTGTCGGGCGATTGCCCGCGCCCCGGCGTGTAT

GAGGTGCCCTTCGGCCTCACGGTGAACGCGCTGCTCGACCTTGTC

GGCGCGCCGGACGCCGCCTTCGTGCAGATGGGTGGGCCGTCCGGC

CAATGCGTGGCGCCGAAGGATTACGGCCGCCGCATCGCCTTCGAG

GACCTGCCCACCGGCGGCTCGGTGATGGTGTTCGGCCCGGGGCGC

GACGTGCTCGCCATGGTGCGCGAGTTCGCGGATTTCTTCGCCGGC

GAATCCTGCGGCTGGTGCACGCCCTGCCGGGTGGGCACCACCTTG

CTCAAGGAAGAGCTGGACAAGCTCCTCGCCAACCGCGCCACCCTC

GCCGACATCCGCGCGCTGGAGACCCTGGCCACGACCGTCTCCCGC

ACCAGCCGCTGCGGCCTCGGCCAGACGGCGCCCAACCCCATCCTT

TCCACCATGCGCAACCTGCCGGAAGCCTATGAGGCGAGGCTGAGG

CCCGAAGACTTCCTGCCCTGGGCCTCGCTCGACGAGGCGCTGAAG

CCCGCCATCGTCATCCAGGGCCGCGCGCCCGTGCCGGAGGAAGAG

GCATGA
```

SEQ ID NO: 7:
Amino acid sequence of NAD⁺-
reducing hydrogenase HoxS subunit alpha:
```
MMPSEPHGAGMPPPREAAAVPTPQEVSAVVAEVVADAVASVGGAR
```

-continued
```
TRLMDIVQLAQQRLGHLSEETMAAIAARLAIPPVEVADMVSFYAF

LNRAPKGRYHIRLSRSPISLMKGAEAVAAAFCQILGIAMGETSQD

GDFTLEWTNDIGMADQEPAALVNGTVMTQLAPGDAAIIVGRLRAH

HAPNALPLFPGAGVAGSGLPHARIRPSLVMPGQLLFREDHTTPGA

GIKAALALTPDEVVQKVSAARLRGRGGAGFPTGLKWKLCRQSPAT

TRHVICNADEGEPGTFKDRVLLTQAPHLMFDGMTIAGYALGAREG

VVYLRGEYAYLWEPLHAVLRERYGLGLAGANILGHAGFDFDIRIQ

LGAGAYICGEESALVESLEGKRGSPRDRPPFPTVRGHLQQPTAVD

NVETFACAARILEDGVEAFAGIGTPESAGTKLLSVSGDCPRPGVY

EVPFGLTVNALLDLVGAPDAAFVQMGGPSGQCVAPKDYGRRIAFE

DLPTGGSVMVFGPGRDVLAMVREFADFFAGESCGWCTPCRVGTTL

LKEELDKLLANRATLADIRALETLATTVSRTSRCGLGQTAPNPIL

STMRNLPEAYEARLRPEDFLPWASLDEALKPAIVIQGRAPVPEEE

A
```

SEQ ID NO: 8:
Nucleotide sequence of NAD⁺-
reducing hydrogenase HoxS subunit beta:
```
ATGAGCCGGGGATCCCCCGATGCCGGGAAAGACCGCACCATGAGC

GCCACCGACGGCACCACCGCCCCCCCGCAAGATCGTCATCGATCCG

GTGACCCGCGTGGAGGGCCACGGCAAGGTCACCATCCGCCTGGAT

GAAGCCGGCGCGGTGGAGGATGCGCGTTTCCACATCGTGGAGTTC

CGCGGCTTCGAGCGGTTCATCCAGGGCCGGATGTACTGGGAAGTG

CCCCTTATCATCCAGCGGCTGTGCGGCATCTGCCCGGTGAGCCAC

CATCTGGCGGCGGCGAAAGCCATGGACCAGGTGGCGGGCGTGGAC

CGCGTACCGCCCACCGCCGAGAAACTGCGCCGGCTGATGCATTAT

GGGCAGGTGCTGCAATCCAACGCTTTGCACATCTTCCACCTCGCC

TCGCCCGACCTCCTGTTCGGCTTCGACGCGCCGGCCGAGCAGCGC

AACATCATCGCCGTGCTCCAGCGTTATCCGGAGATCGGCAAATGG

GCGATCTTCATCAGGAAGTTCGGCCAGGAGGTCATCAAGGCCACC

GGCGGGCGCAAGATCCATCCCACCAGCGCCATTCCCGGCGGGGTC

AACCAGAACCTCGCCGTGGAGGACCGCGACGCCCTGCGCGCCAAG

GTGGGCGAGATCATCAGCTGGTGCATGGCGGCGCTGGACCATCAC

AAGGCCTATGTGGCGGAAAACCGGGCGCTGCATGACAGCTTCGCC

GCCTTCCCCTCCGCCTTCATGAGCCTCGTGGGGCCGGATGGCGGC

ATGGACCTTTATGACGGCACCCTGCGGGTGATCGATGCCGAGGGC

GCCCCCCTCATCGAAGGCGCGCCGCCCGCCTCCTACCGCGACCAC

CTCATCGAGGAGGTGCGCGCCCTGGAGCTATCTGAAATTCCCCCAT

CTGCGCGCCTTCGGCCGCGACGATGGCTGGTATCGGGTCGGCCCC

CTCGCCCAGGTCAATTGCGCCGCGTCCATCGACACGCCCCGCGCC

GAGGCGGCCCGGCGGGACTTCATGGCCGAGGGGGGGGGCAAGCCGG

TGCATGCCACCCTCGCTTATCACTGGGCGCGGCTCATCGTGCTGG

TCCATTGCGCGGGAGAAGATCGAACAGCTGCTGTTCGACGACGACC
```

-continued

TGCAAGGCTGCGATCTGCGTGCGGAGGGCACCCGGCGCGGGGAAG

GCGTCGCCTGGATCGAGGCGCCGCGCGGCACCCTCATCCACCATT

ACGAGGTGGACGAGAACGACCAGGTGCGCCGCGCCAACCTCATCG

TCTCCACCACCCACAATAACGAGGCCATGAACCGCGCCGTGCGGC

AGGTGGCGAAGACGGACCTTTCCGGTCGCGAGATCACCGAAGGGC

TGCTGAACCATATCGAGGTGGCCATCCGCGCCTTCGACCCCTGCC

TGTCCTGCGCCACCCATGCGCTGGGCCAGATGCCGCTGATCGTGA

CGCTTGAAGATGCCTCCGGCGCAGAGATCGCCCGCGGAGTGAAGG

AATGA

SEQ ID NO: 9:
Amino acid sequence of NAD$^+$-
reducing hydrogenase HoxS subunit beta:
MSRGSPDAGKDRTMSATDGTTAPRKIVIDPVTRVEGHGKVTIRLD

EAGAVEDARFHIVEFRGFERFIQGRMYWEVPLIIQRLCGICPVSH

HLAAAKAMDQVAGVDRVPPTAEKLRRLMHYGQVLQSNALHIFHLA

SPDLLFGFDAPAEQRNIIAVLQRYPEIGKWAIFIRKFGQEVIKAT

GGRKIHPTSAIPGGVNQNLAVEDRDALRAKVGEIISWCMAALDHH

KAYVAENRALHDSFAAFPSAFMSLVGPDGGMDLYDGTLRVIDAEG

APLIEGAPPASYRDHLIEEVRPWSYLKFPHLRAFGRDDGWYRVGP

LAQVNCAASIDTPRAEAARRDFMAEGGGKPVHATLAYHWARLIVL

VHCAEKIEQLLFDDDLQGCDLRAEGTRRGEGVAWIEAPRGTLIHH

YEVDENDQVRRANLIVSTTHNNEAMNRAVRQVAKTDLSGREITEG

LLNHIEVAIRAFDPCLSCATHALGQMPLIVTLEDASGAEIARGVK

E

SEQ ID NO: 10:
Nucleotide sequence of NAD$^+$-
reducing hydrogenase HoxS subunit gamma:
ATGAGCGAGACCCCCTTCACCTTTACCGTGGACGGCATCGCGGTC

CCGGCCACCCCCGGCCAGAGCGTCATCGAGGCGTGCGATGCGGGG

GCATCTATATCCCGCGCCTGTGCCACCACCCGGACCTGCCGCCGG

CGGGCCATTGCCGGGTGTGCACCTGCATCATCGACGGGCGGCCGG

CCAGCGCCTGCACCATGCCCGCCGCCAGGGGCATGGTGGTGGAGA

ACGAGACGCCCGCTTTGCTGGCGGAGCGGCGCACGCTGATCGAGA

TGCTGTTCGCGGAAGGCAACCATTTCTGCCAGTTCTGCGAGGCGA

GCGGCGATTGCGAATTGCAGGCGCTGGGCTACCTGTTCGGCATGG

TGGCCCCGCCCTTCCCCCATCTGTGGCCGAAGCGGCCGGTGGATG

CCAGCCATCCGGATATCTATATCGACCACAATCGCTGCATCCTGT

GCTCGCGCTGCGTGCGCGCCTCGCGCACCCTGGACGGCAAGTCCG

TGTTCGGCTTCGAGGGGCGCGGCATCGAGATGCATCTGGCGGTGA

CCGGCGGGCACCTGGACGACAGCGCCATCGCCGCCGCCGACAGGG

CGGTTGAGATGTGCCCGGTGGGCTGCATCGTCCTCAAGCGCACCG

GCTACCGCACGCCCTATGGCCGGCGGCGCTACGACGCCGCGCCCA

TCGGCTCCGACATCACCGCCCGGCGCGGCGGCGCGAAGGACTGA

-continued

SEQ ID NO: 11:
Amino acid sequence of NAD$^+$-
reducing hydrogenase HoxS subunit gamma:
MSETPFTFTVDGIAVPATPGQSVIEACDAAGIYIPRLCHHPDLPP

AGHCRVCTCIIDGRPASACTMPAARGMVVENETPALLAERRTLIE

MLFAEGNHFCQFCEASGDCELQALGYLFGMVAPPFPHLWPKRPVD

ASHPDIYIDHNRCILCSRCVRASRTLDGKSVFGFEGRGIEMHLAV

TGGHLDDSAIAAADRAVEMCPVGCIVLKRTGYRTPYGRRRYDAAP

IGSDITARRGGAKD

SEQ ID NO: 12:
Nucleotide sequence of NAD$^+$-
reducing hydrogenase HoxS subunit delta:
ATGGCCAAGCCCAAACTCGCCACCTGCGCGCTGGCCGGCTGCTTC

GGCTGCCACATGTCCTTCCTGGACATGGACGAGCGCATCGTCGAG

CTCATCGACCTGGTGGACCTCGACGTCTCGCCCCTCGACGACAAG

AAAAACTTCACCGGCATGGTGGAAATCGGCCTGGTGGAAGGCGGC

TGCGCCGACGAGCGCCATGTGAAGGTGCTGCGCGAGTTCCGCGAG

AAATCCCGCATCCTGGTGGCGGTGGGCGCCTGCGCCATCACCGGC

GGCATCCCGGCATTGCGCAACCTCGCCGGCCTCGACGAATGCCTG

AGGGAAGCCTACCTCACCGGCCCCACGGTGGAAGGCGGCGGGCTC

ATTCCCAACGACCCGGAGCTGCCGCTGCTGCTGGACAAGGTCTAT

CCGGTGCAGGACTTCGTGAAGATCGACCATTTCCTGCCCGGCTGC

CCGCCCTCGGCCGACGCCATCTGGGCGGCTCTGAAGGCGCTGCTG

ACCGGCACCGAGCCGCATCTGCCCTACCCGCTTTTCAAGTACGAA

TGA

SEQ ID NO: 13:
Amino acid sequence of NAD$^+$-
reducing hydrogenase HoxS subunit delta:
MAKPKLATCALAGCFGCHMSFLDMDERIVELIDLVDLDVSPLDDK

KNFTGMVEIGLVEGGCADERHVKVLREFREKSRILVAVGACAITG

GIPALRNLAGLDECLREAYLTGPTVEGGGLIPNDPELPLLLDKVY

PVQDFVKIDHFLPGCPPSADAIWAALKALLTGTEPHLPYPLFKYE

In another embodiment, the bacterial strain used in the process of the invention comprises a gene encoding a NiFeSe hydrogenase large subunit having the sequence set forth in SEQ ID NO:15 or a sequence having more than 84% sequence identity, e.g. more than 90% identity, such as more than 95% identity, e.g. more than 96% identity, such as more than 97% identity, e.g. more than 98%, such as more than 99% sequence identity to the sequence set forth in SEQ ID NO:15.

In another embodiment, the bacterial strain used in the process of the invention comprises a gene encoding a NiFeSe hydrogenase small subunit having the sequence set forth in SEQ ID NO: 17 or a sequence having more than 90% identity, such as more than 95% identity, e.g. more than 96% identity, such as more than 97% identity, e.g. more than 98%, such as more than 99% sequence identity to the sequence set forth in SEQ ID NO:17.

SEQ ID NO: 14:
Nucleotide sequence of Periplasmic [NiFeSe] hydrogenase large subunit:

-continued

TCCAGACCCGGGCAACATTGCTCCATGTGCTGGGCACCCTGGCCG

GCCGCTGGCCCCATACCCTCGCGCTCCAGCCCGGCGGGGTGACCC

GAAGCGCCGACCAGCACGACCGCATGCGCCTGCTCGCGACGCTGA

AGGCGGTGCGGGGGGCGCTGGAAGAGACCTTGTTCGGCGCGCCTT

TGGAAGAGGTGGCGGCCCTGGACGGCGCCGCCGCCGTGGAGGCCT

GGCGCGCCAACGGCCCGGAAGGGGATTTCCGCCTGTTCCTGGAGA

TCGCCGCCGACCTGGAGCTGGACCGGCTCGGCCGCGCGCACGACC

GCTTTCTCTCCTTCGGCGCCTACGCCCAGGACGAGGGGCGCCTTT

ATGGCGCCGGCACCTTCGAGGCCGGGACGGGGGAGGGCTCGATCC

CAACGCCATCACCGAGGACCACGCCTTCGCCCGCATGGAGGACCG

CGCGGCGCCCCATGCGCCCTTTGACGGCTCCACCTTCCCCGATGC

CGACGACACCGAGGGCTACACCTGGTGCAAGGCGCCGCGCCTTGC

CGGCCTGCCCTTCGAGACCGGCGCCTTCGCCCGGCAGGTGGTGGC

GGGCCATCCGCTCGCCCGGGACCTCGTGACGCGGGAAGGCGGCAC

TGTGCGCAGCCGCGTGGTCGGCCGGCTGCTGGAAACCGCGCGCAC

CCTGATCGCCATGGAGGGCTGGGTGAAGGAACTGCGGCCCGAAGG

GCCCTGGTGCGCCCAGGGCCACCTGCCCCAGGAAGGCCGCGCCTT

CGGCCTCACCGAGGCGGCGCGCGGGGCGCTCGGCCACTGGATGGT

GGTGGAGAAGGGCCGCATTGCCCGCTACCAGATCATCGCCCCCAC

CACCTGGAACTTCTCCCCCCGCGACGGCGCGGGCCTGCCCGGCCC

GCTGGAGACGGCCCTGGTGGGCGCGCCCGTGCGGCAGGGAGAGAC

GACGCCCGTGAGCGTGCAGCACATCGTGCGCTCCTTCGACCCGTG

CATGGTCTGCACTGTGCATTGA

SEQ ID NO: 15:
Amino acid sequence of Periplasmic [NiFeSe]
hydrogenase large subunit:
MSAETRRLVVGPFNRVEGDLEVRLDVQDGRVQQAFVSSPLFRGFE

RILEGRDPRDALVIAPRICGICSVSQSHAAALALAGLQGIAPTHD

GRIATNLIVAAENVADHLTHFHVFFMPDFARAVYEDRPWFAQAAR

RFKANQGVSVRRALQTRATLLHVLGTLAGRWPHTLALQPGGVTRS

ADQHDRMRLLATLKAVRAALEETLFGAPLEEVAALDGAAAVEAWR

ANGPEGDFRLFLEIAADLELDRLGRAHDRFLSFGAYAQDEGRLYG

AGTFEAGTAGGLDPNAITEDHAFARMEDRAAPHAPFDGSTFPDAD

DTEGYTWCKAPRLAGLPFETGAFARQVVAGHPLARDLVTREGGTV

RSRVVGRLLETARTLIAMEGWVKELRPEGPWCAQGHLPQEGRAFG

LTEAARGALGHWMVVEKGRIARYQIIAPTTWNFSPRDGAGLPGPL

ETALVGAPVRQGETTPVSVQHIVRSFDPCMVCTVH

SEQ ID NO: 16:
Nucleotide sequence of Periplasmic [NiFeSe]
hydrogenase small subunit
ACGGGGAGGAAGCCCGCGCCATCTTCGACGCCATCCTTGCCGGC

GTTATCGTCCTCGACGCCCTGTGCGTGGAAGGCGCGCTGCTGCGC

GGGCCGAACGGCACCGGGCGCTTCCATGTGCTGGCGGGCACGGAC

ACCCCCACCATCGACTGGGCGCGGCAGCTCGCCGGCATGGCGCGC

-continued

CACGTGGTGGCGGTGGGCACCTGCGCCGCCTATGGGGGCGTGACG

GCGGCGGGCATCAACCCCACCGATGCCTGCGGCCTCCAGTTCGAC

GGACGCCGGAAGGGTGGGGCGCTGGGGGGGGACTTCCGCTCCCGC

TCGGGGCTTCCGGTCATCAATGTGGCCGGCTGCCCCACCCATCCC

AACTGGGTGACGGAAACCCTGATGCTGCTCGCCTGCGGCCTGCTG

GGCGAGGCCGACCTCGACGTCTATGGCCGCCCGCGCTTCTATGCG

GACCTGCTGGTGCATCACGGCTGCCCGCGCAACGAATACTATGAA

TACAAGGCGAGCGCCGAGAAGATGAGCGACCTCGGCTGCATGATG

GAGCATCTGGGCTGCCTCGGCACCCAGGCCCACGCCGACTGCAAC

ACGCGCCTTTGGAATGGCGAGGGCTCGTGCACCCGCGGCGGCTAT

GCCTGCATCAACTGCACGGCGCCGGAATTCGAGGAGCCGGGCCAC

GCCTTCCTGGAGACGCCCAAGATCGGCGGCATCCCCATCGGCCTG

CCCACCGACATGCCCAAGGCCTGGTTCATCGCCTTGTCCTCCCTC

GCCAAGGCGGCGACGCCGGAGCGGCTGCGCAAGAACGCGGTGTCC

GACCATGTGGTCACGCCGCCCGCCGTCAAGGACATCAAGCGGCGA

TGA

SEQ ID NO: 17:
Amino acid sequence of Periplasmic [NiFeSe]
hydrogenase small subunit
MSTPFSVLWLQSGGCGGCTMSLLCAEAPDLATTLDAAGIGFLWHP

ALSEETGEEARAIFDAILAGVIVLDALCVEGALLRGPNGTGRFHV

LAGTDTPTIDWARQLAGMARHVVAVGTCAAYGGVTAAGINPTDAC

GLQFDGRRKGGALGADFRSRSGLPVINVAGCPTHPNWVTETLMLL

ACGLLGEADLDVYGRPRFYADLLVHHGCPRNEYYEYKASAEKMSD

LGCMMEHLGCLGTQAHADCNTRLWNGEGSCTRGGYACINCTAPEF

EEPGHAFLETPKIGGIPIGLPTDMPKAWFIALSSLAKAATPERLR

KNAVSDHVVTPPAVKDIKRR

In another embodiment, the bacterial strain used in the process of the invention comprises a gene encoding an ATP synthase gamma chain atpG_1 having the sequence set forth in SEQ ID NO: 19 or a sequence having more than 70% identity, such as more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:19.

In another embodiment, the bacterial strain used in the process of the invention comprises a gene encoding an ATP synthase subunit alpha atpA_1 having the sequence set forth in SEQ ID NO:21 or a sequence having more than 78% identity, such as more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:21.

In another embodiment, the bacterial strain used in the process of the invention comprises a gene encoding an ATP synthase subunit b atpF_1 having the sequence set forth in SEQ ID NO:23 or a sequence having more than 62% identity, e.g. more than 70% identity, such as more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:23.

In another embodiment, the bacterial strain used in the process of the invention comprises a gene encoding an ATP synthase subunit c, sodium ion specific atpE_1 having the sequence set forth in SEQ ID NO:25 or a sequence having more than 90% identity, such as more than 95% identity, e.g. more than 96% identity, such as more than 97% identity, e.g. more than 98%, such as more than 99% sequence identity to the sequence set forth in SEQ ID NO:25.

In another embodiment, the bacterial strain used in the process of the invention comprises a gene encoding an ATP synthase subunit a atpB_1 having the sequence set forth in SEQ ID NO:27 or a sequence having more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:27.

In another embodiment, the bacterial strain used in the process of the invention comprises a gene encoding an ATP synthase epsilon chain atpC_1 having the sequence set forth in SEQ ID NO:29 or a sequence having more than 71% identity, such as more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:29.

In another embodiment, the bacterial strain used in the process of the invention comprises a gene encoding an ATP synthase subunit beta atpD_1 having the sequence set forth in SEQ ID NO:31 or a sequence having more than 84% identity, e.g. more than 90% identity, such as more than 95% identity, e.g. more than 96% identity, such as more than 97% identity, e.g. more than 98%, such as more than 99% sequence identity to the sequence set forth in SEQ ID NO:31.

In another embodiment, the bacterial strain used in the process of the invention comprises a gene encoding an ATP synthase subunit beta atpD_2 having the sequence set forth in SEQ ID NO:33 or a sequence having more than 97% identity, e.g. more than 98%, such as more than 99% sequence identity to the sequence set forth in SEQ ID NO:33.

In another embodiment, the bacterial strain used in the process of the invention comprises a gene encoding an ATP synthase gamma chain atpG_2 having the sequence set forth in SEQ ID NO:35 or a sequence having more than 86% identity, e.g. more than 90% identity, such as more than 95% identity, e.g. more than 96% identity, such as more than 97% identity, e.g. more than 98%, such as more than 99% sequence identity to the sequence set forth in SEQ ID NO:35.

In another embodiment, the bacterial strain used in the process of the invention comprises a gene encoding an ATP synthase subunit alpha atpA_2 having the sequence set forth in SEQ ID NO:37 or a sequence having more than 98%, such as more than 99% sequence identity to the sequence set forth in SEQ ID NO:37.

In another embodiment, the bacterial strain used in the process of the invention comprises a gene encoding an ATP synthase subunit delta atpH having the sequence set forth in SEQ ID NO:39 or a sequence having more than 85% identity, e.g. more than 90% identity, such as more than 95% identity, e.g. more than 96% identity, such as more than 97% identity, e.g. more than 98%, such as more than 99% sequence identity to the sequence set forth in SEQ ID NO:39.

In another embodiment, the bacterial strain used in the process of the invention comprises a gene encoding an ATP synthase subunit b atpF_2 having the sequence set forth in SEQ ID NO:41 or a sequence having more than 87% identity, e.g. more than 90% identity, such as more than 95% identity, e.g. more than 96% identity, such as more than 97% identity, e.g. more than 98%, such as more than 99% sequence identity to the sequence set forth in SEQ ID NO:41.

In another embodiment, the bacterial strain used in the process of the invention comprises a gene encoding an ATP synthase subunit b' atpG_3 having the sequence set forth in SEQ ID NO:43 or a sequence having more than 81% identity, e.g. more than 90% identity, such as more than 95% identity, e.g. more than 96% identity, such as more than 97% identity, e.g. more than 98%, such as more than 99% sequence identity to the sequence set forth in SEQ ID NO:43.

In another embodiment, the bacterial strain used in the process of the invention comprises a gene encoding ATP synthase subunit c atpE_2 having the sequence set forth in SEQ ID NO:45 or a sequence having more than 98%, such as more than 99% sequence identity to the sequence set forth in SEQ ID NO:45.

In another embodiment, the bacterial strain used in the process of the invention comprises a gene encoding an ATP synthase subunit a atpB_2 having the sequence set forth in SEQ ID NO:47 or a sequence having more than 92% identity, such as more than 95% identity, e.g. more than 96% identity, such as more than 97% identity, e.g. more than 98%, such as more than 99% sequence identity to the sequence set forth in SEQ ID NO:47.

In another embodiment, the bacterial strain used in the process of the invention comprises a gene encoding an ATP synthase protein I atpI having the sequence set forth in SEQ ID NO:49 or a sequence having more than 60% identity, e.g. more than 70% identity, such as more than 80% identity, e.g. more than 90% identity, such as more than 95% identity, e.g. more than 96% identity, such as more than 97% identity, e.g. more than 98%, such as more than 99% sequence identity to the sequence set forth in SEQ ID NO:49.

```
SEQ ID NO: 18:
Nucleotide sequence of ATP synthase gamma
chain atpG_1
GTGACCGAGCGCCTGTCCGACGTCAACGCCCGCATCGCCTCGGTG

CGGCAGCTCTCATCGGTCATCACGGCCATGCGGGGCATTGCGGCG

GCGCGGGCGCGGGAGGCGCGGGGTCGGCTCGACGGCATCCGCGCC

TATGCGCAGACCATCGCCGAGGCCATCGGCCATGTGCTCGCCGTG

CTGCCCGAGGAGGCCCGCGCCCGGTCCTCCGGGCACCGGCATCGG

GGCCATGCGGTCATCGCCCTGTGCGCGGAGCAGGGCTTTGCCGGC

GTCTTCAACGAGCGGGTGCTGGACGAGGCCGCCCGGCTGCTGACC

GGCGGGGCGGGGCCGGCCGAGCTGCTGCTGGTGGGCGACCGGGGC

CTGATGGTGGCCCGCGAGCGGGGGCTCGATGTCTCCTGGTCGGTG

CCCATGGTGGCCCATGCGGGCCAGGCCTCGGCGCTGGCGGACCGC

ATCAGCGAGGAGCTCTACCGGCGGATCGATGCGGGACGGGTGACG
```

-continued

CGGGTGTCGGTGGTGCACGCCGAGCCCGCCGCGTCCGCCGCCATC

GAGACGGTGGTGAAAGTGCTGGTGCCGTTCGACTTCGCCCGCTTC

CCCCTGGCGCGGGTGGCATCCGCCCCGCTCATGACCATGCCGCCG

CCGCGGCTGCTGGCCCAGCTGTCGGAGGAATATGTGTTCGCCGAG

CTGTGCGAGGCGCTCACCTTGTCCTTCGCGGCGGAGAACGAGGCC

CGCATGCGGGCCATGATCGCCGCCCGCGCCAATGTGGCCGATACC

CTGGAGGGCCTCGTCGGCCGCGCCCGGCAGATGCGCCAGGAGGAG

ATCACCAACGAGATCATCGAGCTGGAAGGCGGCGCCGGCAGCGCC

CGGCATGCGGATTGA

SEQ ID NO: 19:
Amino acid sequence of ATP synthase gamma
chain atpG_1
MTERLSDVNARIASVRQLSSVITAMRGIAAARAREARGRLDGIRA

YAQTIAEAIGHVLAVLPEEARARSSGHRHRGHAVIALCAEQGFAG

VFNERVLDEAARLLTGGAGPAELLLVGDRGLMVARERGLDVSWSV

PMVAHAGQASALADRISEELYRRIDAGRVTRVSVVHAEPAASAAI

ETVVKVLVPFDFARFPLARVASAPLMTMPPPRLLAQLSEEYVFAE

LCEALTLSFAAENEARMRAMIAARANVADTLEGLVGRARQMRQEE

ITNEIIELEGGAGSARHAD

SEQ ID NO: 20:
Nucleotide sequence of ATP synthase subunit
alpha atpA_1
ATGAGCACGGGCGCGCAAGCGAGCGAGGATTGGCTCACCCGGAGC

CGGGCGGCCCCTGGCCGGGACGCGCCTTTCCCAGCAATCCCAATCG

GTGGGCCGGGTGGAGGAGATGGCCGACGGCATCGCCCGCGTCTCC

GGCCTGCCGGATGTGCGGCTCGACGAGCTTCTCACCTTCGAGGGC

GGCCAGACCGGCTATGCCCTCACCCTCGATCGCACCGAGATCGCC

GTGGTGCTGCTGGATGACGCCTCCGGCGTGGAGGCGGGCGCCCGG

GTGTTCGGCACCGGCGAGGTGGTGAAGGTGCCGGTGGGGCCGGGG

CTGCTGGGCCGCATCGTCGACCCCCTCGGCCGGCCCATGGACCGC

TCCGAGCCGGTGGTGGCGCAGGCGCACCATCCCATCGAGCGGCCG

GCGCCGGCCATCATCGCCCGCGACCTGGTCTCGCAGCCGGTTCAG

ACCGGCACGCTGGTGGTGGATGCGCTGTTCTCCCTCGGCCGGGGC

CAGCGCGAGCTCATCATCGGCGACCGGGCTACCGGCAAGACCGCC

ATCGCGGTGGACACCATCATCAGCCAGAAGCATTCGGACATCGTG

TGCATCTACGTGGCGGTGGGCCAGCGCGCCGCCGCCGTGGAGCGG

GTGGTGGAGGCGGTGCGCGCCCACGGGGCGATCGAGCGCTGCATC

TTCGTGGTCGCCTCGGCCGCCGCCTCGCCAGGGCTGCAATGGATC

GCGCCGTTCGCCGGCATGACCATGGCGGAATATTTCCGCGACAAC

GGCCAGCATGCGCTCATCATCATCGATGATCTCACCAAGCATGCG

GCCACCCATCGCGAGCTGGCGCTGCTCACCCACGAGCCGCCGGGC

CGCGAGGCCTATCCCGGCGACATCTTCTATGTGCACGCCCGCCTT

CTGGAGCGGGCCGCCAAGCTCTCCGCCGAGCTGGGCGGTGGCTCG

CTCACCGCCCTGCCCATCGCGGAGACGGACGCGGGAAACCTCTCC

-continued

GCCTATATCCCCCACCAACCTCATCTCCATCACCGATGGGCAGATC

GTGCTGGATTCGCGGCTGTTCGCGGCCAACCAGCGCCCGGCGGTG

GATGTGGGCCTCTCCGTGAGCCGGGTGGGCGGCAAGGCGCAGCAT

CCCGCGCTTCGGGCCGTGTCCGGGCGCATCCGGCTCGATTATTCC

CAGTTCCTGGAGCTGGAAATGTTCACCCGCTTCGGCGGCATCACC

GATACCCGCGTGAAGGCGCAGATCACCCGGGGCGAGCGCATCCGC

GCGCTGCTCACCCAGCCGCGCTTTTCCACCCTGCGCCTTCAGGAC

GAGGTGGCGCTGCTGGCCGCGCTGGCGGAGGGGGTGTTCGACACT

TTGGCCCCGGGGCTGATGGGCGCCGTGCGTGCCCGCATTCCGGCC

CAGCTGGATGCGCAGGTGAAGGACGTGGCCTCGGCCCTCGCCGAG

GGCAAGGTGCTGGAGGAGGGCTTGCACGCCCGTCTCGTGGCGGCC

GTGCGGGCCGTCGCGGCCGGACGTGGCCGCGACCGCGAAGGCCGGG

CCGTGA

SEQ ID NO: 21:
Amino acid sequence of ATP synthase subunit
alpha atpA_1
MSTGAQASEDWLTRSRAALAGTRLSQQSQSVGRVEEMADGIARVS

GLPDVRLDELLTFEGGQTGYALTLDRTEIAVVLLDDASGVEAGAR

VFGTGEVVKVPVGPGLLGRIVDPLGRPMDRSEPVVAQAHHPIERP

APAIIARDLVSQPVQTGTLVVDALFSLGRGQRELIIGDRATGKTA

IAVDTIISQKHSDIVCIYVAVGQRAAAVERVVEAVRAHGAIERCI

FVVASAAASPGLQWIAPFAGMTMAEYFRDNGQHALIIIDDLTKHA

ATHRELALLTHEPPGREAYPGDIFYVHARLLERAAKLSAELGGGS

LTALPIAETDAGNLSAYIPTNLISITDGQIVLDSRLFAANQRPAV

DVGLSVSRVGGKAQHPALRAVSGRIRLDYSQFLELEMFTRFGGIT

DTRVKAQITRGERIRALLTQPRFSTLRLQDEVALLAALAEGVFDT

LAPGLMGAVRARIPAQLDAQVKDVASALAEGKVLEEGLHARLVAA

VRAVAADVAATAKAGP

SEQ ID NO: 22:
Nucleotide sequence of ATP synthase subunit
b atpF_1
ATGCAGATCGACTGGTGGACGCTGGGCCTGCAGACGGTCAACGTC

CTCGTTCTCATCTGGCTCCTGAGCCGCTTCCTGTTCAAGCCGGTG

GCGCAGGTCATCGCGCAGCGCCGTGCCGAGATCGAGAAGCTGGTG

GAGGATGCGCGCGCCGCCAAGGCCGCCGCCGAGGCCGAGCGGGAC

ACGGCGAAGGCGGAGGAGGCGCGCCTTGCCGCCGAGCGCGGCGCC

CGCATGGCGGCGGTCGCCAAGGAGGCGGAGGCGCAGAAGGCGGCA

TTGCTGGCCGCCGCCAAGACCGAGGCCGAGGCCCTGCACGCGGCC

GCGGAAGCGGCCATCGTCCGGGCGCGGGCGAGCGAGGAGGAAGCC

GCCGCCGACCGCGCCAGCCGCCTTGCCGTGGACATCGCCGCCAAG

CTGCTGGACCGGCTGCCCGACGACGCCCGGGTCGCGGGCTTCATC

GATGGCCTCGCCGAGGGGCTTGAAGCCCTGCCCGAGGCGAGCCGG

GCGGTGATCGGCGTCGACGGCGCGCCCAGTGCGCGTGACGGCCGCG

-continued

CGCGCCCTTATGCCGGCGGAGGAGGAGGCCTGCCGCACGCGGCTC

TCCCAGGCGCTGGGCCGTCCGGTGACGCTGGCCGTGACCATCGAC

CCCGCCCTCATCGCCGGCCTGGAGATGGAGACGCCCCACGCGGTG

GTGCGCAATTCCTTCAAGGCCGATCTCGACCGCGTCACCGCGGCG

CTCACCCATCATGGGACCTGA

SEQ ID NO: 23:
Amino acid sequence of ATP synthase subunit
b atpF_1
MQIDWWTLGLQTVNVLVLIWLLSRFLFKPVAQVIAQRRAEIEKLV

EDARAAKAAAEAERDTAKAEEARLAAERGARMAAVAKEAEAQKAA

LLAAAKTEAEALHAAAEAAIVRARASEEEAAADRASRLAVDIAAK

LLDRLPDDARVAGFIDGLAEGLEALPEASRAVIGVDGAPVRVTAA

RALMPAEEEACRTRLSQALGRPVTLAVTIDPALIAGLEMETPHAV

VRNSFKADLDRVTAALTHHGT

SEQ ID NO: 24:
Nucleotide sequence of ATP synthase subunit c,
sodium ion specific atpE_1
ATGACTGTCGAGATGGTCAGCATCTTCGCGGCGGCGCTCGCCGTC

TCCTTCGGCGCCATCGGGCCGGCCCTGGGCGAGGGCCGGGCGGTG

GCCGCGGCCATGGACGCCATCGCCCGCCAGCCGGAGGCGGCCGGA

ACCTTGTCGCGCACGCTCTTCGTCGGCCTCGCCATGATCGAGACC

ATGGCGATCTACTGCCTGGTGATCGCGCTCCTGGTGCTCTTCGCC

AATCCGTTCGTGAAGTGA

SEQ ID NO: 25:
Amino acid sequence of ATP synthase subunit c,
sodium ion specific atpE_1
MTVEMVSIFAAALAVSFGAIGPALGEGRAVAAAMDAIARQPEAAG

TLSRTLFVGLAMIETMAIYCLVIALLVLFANPFVK

SEQ ID NO: 26:
Nucleotide sequence of ATP synthase subunit a
atpB_1
ATGGGCTCGCCGCTGATCCTCGAACCCCTGTTCCATATCGGGCCC

GTGCCCATCACCGCGCCGGTGGTGGTCACCTGGCTCATCATGGCC

GCCTTCATTGGGCTGGCGCGGCTCATCACCCGGAAGCTTTCCACC

GATCCCACCCGGACCCAGGCGGCGGTGGAAACGGTGCTGACCGCC

ATCGATTCCCAGATCGCCGACACCATGCAGGCCGATCCCGCGCCT

TATCGCGCGCTCATCGGCACCATCTTCCTTTATGTGCTGGTGGCC

AACTGGTCCTCGCTCATCCCGGGCATCGAGCCGCCCACGGCGCAT

ATCGAGACCGATGCGGCGCTCGCCTTTCATCGTGTTCGCCGCCACC

ATCGGGTTCGGGTTGAAGACAAGGGGTGTGAAGGGCTATCTCGCC

ACCTTCGCCGAACCCTCCTGGGTGATGATCCCGCTCAATGTGGTG

GAGCAGATCACCCGGACCTTCTCGCTCATCGTGCGCCTGTTCGGC

AACATCATGAGCGGGGTGTTCGTGGTCGGCATCATCCTGTCCCTC

GCCGGGCTGCTGGTGCCCATCCCCCTCATGGCGCTCGATCTCCTG

ACCGGCGCCGTGCAGGCCTACATCTTCGCGGTGCTGGCCTGCGTG

TTCATCGGCGCGGCCATTGGCGAGGCGCCGGCAAAGCCCCAATCG

AAGGAGCCAGGGAAAACATCATGA

-continued

SEQ ID NO: 27:
Amino acid sequence of ATP synthase subunit a
atpB_1
MGSPLILEPLFHIGPVPITAPVVVTWLIMAAFIGLARLITRKLST

DPTRTQAAVETVLTAIDSQIADTMQADPAPYRALIGTIFLYVLVA

NWSSLIPGIEPPTAHIETDAALAFIVFAATIGFGLKTRGVKGYLA

TFAEPSWVMIPLNVVEQITRTFSLIVRLFGNIMSGVFVVGIILSL

AGLLVPIPLMALDLLTGAVQAYIFAVLACVFIGAAIGEAPAKPQS

KEPGKTS

SEQ ID NO: 28:
Nucleotide sequence of ATP synthase epsilon
chain atpC_1
GTGAGCGCGCCGCTGCACCTCACCATCACCACGCCGGCCGCCGTT

CTGGTGGACCGTGCCGACATCGTGGCCCTGCGTGCCGAGGACGAG

AGCGGCAGCTTCGGCATCCTGCCCGGCCATGCGGATTTCCTGACC

GTTCTGGAGGCCTGCGTGGTGCGCTTCAAGGATGGGGCCGACGGC

GTGCATTATTGTGCTCTCAGTGGTGGCGTGCTGTCGGTCGAGGAG

GGCCGGCGCATCGCCATCGCCTGCCGTCAGGGCACGGTGAGCGAC

GACCTGGTCGCCCTGGAAGGGGCGGTGGACGCCATGCGTTCGGCG

GAGAGCGATGCCGACAAGCGGGCCCGGGTGGAGCAGATGCGCCTT

CATGCCCACGCCGTGCGCCAGCTCCTGCACTATCTGCGGCCCGGC

CGGGCCGGCGGCGTGGCGCCGGCCGCCGCGCCGGAGGAGGGGCCG

TCATGA

SEQ ID NO: 29:
Amino acid sequence of ATP synthase epsilon
chain atpC_1
MSAPLHLTITTPAAVLVDRADIVALRAEDESGSFGILPGHADFLT

VLEACVVRFKDGADGVHYCALSGGVLSVEEGRRIAIACRQGTVSD

DLVALEGAVDAMRSAESDADKRARVEQMRLHAHAVRQLLHYLRPG

RAGGVAPAAAPEEGPS

SEQ ID NO: 30:
Nucleotide sequence of ATP synthase subunit
beta atpD_1
ATGGCAGCGGCAGATGAGGAGGCGCAATCGGCCGCCGGCCCCGCC

TCGGGCCGGGTGGTGGCCGTGCGCGGCGCGGTGATCGACATCGCC

TTTGCCCAGCCTCCGCTGCCGCCGCTGGACGACGCCCTTCTCATC

ACCGACGGCCGGGGCGGCACGGTGCTGGTGGAGGTGCAGAGCCAT

ATGGATCGGCACACGGTGCGCGCCATCGCCCTTCAGGCCACCACC

GGCCTCAGCCGGGGGCTGGAGGCGGCGCGGGTGGGCGGGCCGGTG

AAGGTGCCGGTGGGAGACCATGTGCTCGGCCGCCTCCTGGATGTC

ACCGGCGCCATCGGCGACAAGGGGGGCCGCTGCCGGCCGACGTGC

CCACGCGGCCGATCCACCACGCGCCGCCATCCTTCGCCGCGCAGG

GCGGCACGTCCGATCGTGTTTCGCACCGGCATCAAGGTCATCGACC

TCCTGGCGCCCCTCGCCCAGGGCGGCAAGGCGGCCATGTTCGGCG

GGGCCGGCGTGGGCAAGACCGTGCTGGTGATGGAGCTGATCCACG

CCATGGTGGCGAGCTACAAGGGCATCTCGGTGTTTGCCGGCGTGG

-continued

```
GGGAGCGCTCCCGCGAGGGCCACGAGATGCTGCTGGACATGACCG

ATTCCGGCGTGCTCGACCGCACCGTTCTGGTCTATGGCCAGATGA

ACGAGCCCCCCGGGGCCCGCTGGCGGGTGCCCATGACGGCGCTGA

CCATCGCCGAATATTTCCGCGACGAGAAGCACCAGAACGTCCTGC

TGCTGATGGACAACATCTTCCGCTTCGTCCAGGCGGGGGCGGAGG

TCTCCGGCCTTTTGGGCCGTCCGCCCTCCCGGGTGGGATACCAGC

CGACGCTGGCGAGCGAGGTGGCGGCGCTCCAGGAACGCATCACCT

CCGTGGGCGAGGCCTCGGTGACCGCCATCGAGGCGGTCTACGTGC

CGGCGGATGACTTCACCGATCCCGCCGTGACCACCATCGCCGCCC

ACGTGGATTCCATGGTGGTGCTCTCCCGCGCCATGGCGGCGGAGG

GCATGTATCCGGCGGTGGACCCCATCTCCTCCTCGTCGGTGCTGC

TCGACCCGCTCATCGTGGGGGACGAGCATGCGCGCGTCGCCAACG

AGGTGCGCCGGACCATCGAGCATTATCGCGAGCTTCAGGATGTGA

TCTCGCTGCTGGGCATGGAGGAATTGGGCACCGAGGATCGCCGCA

TCGTGGAGCGGGCGCGCCGGCTCCAGCGCTTCCTCACCCAGCCCT

TCACGGTCACCGAGGCCTTCACCGGCGTGCCCGGCCGCTCGGTGG

CCATCGCCGACACCATCGCCGGCTGCAGGATGATCCTGTCCGGCG

CCTGCGACGACTGGCAGGAAAGCGCCCTCTACATGGTGGGCACCA

TCGACGAGGCCCGCCAGAAGGAGGAGGCCGCTCGCGCCAAGGCGG

GGCAGGGCGCCCCGGCCGGGACGGCAGCCGAGACGGCGGAGGCCG

CCCCGTGA
```

SEQ ID NO: 31:
Amino acid sequence of ATP synthase subunit
beta atpD_1
```
MAAADEEAQSAAGPASGRVVAVRGAVIDIAFAQPPLPPLDDALLI

TDGRGGTVLVEVQSHMDRHTVRAIALQATTGLSRGLEAARVGGPV

KVPVGDHVLGRLLDVTGAIGDKGGPLPADVPTRPIHHAPPSFAAQ

GGTSDLFRTGIKVIDLLAPLAQGGKAAMFGGAGVGKTVLVMELIH

AMVASYKGISVFAGVGERSREGHEMLLDMTDSGVLDRTVLVYGQM

NEPPGARWRVPMTALTIAEYFRDEKHQNVLLLMDNIFRFVQAGAE

VSGLLGRPPSRVGYQPTLASEVAALQERITSVGEASVTAIEAVYV

PADDFTDPAVTTIAAHVDSMVVLSRAMAAEGMYPAVDPISSSSVL

LDPLIVGDEHARVANEVRRTIEHYRELQDVISLLGMEELGTEDRR

IVERARRLQRFLTQPFTVTEAFTGVPGRSVAIADTIAGCRMILSG

ACDDWQESALYMVGTIDEARQKEEAARAKAGQGAPAGTAAETAEA

AP
```

SEQ ID NO: 32:
Nucleotide sequence of ATP synthase subunit
beta atpD_2
```
ATGGCGAACAAGGTCGGACGCATCACCCAGATCATCGGCGCCGTC

GTCGACGTGCAGTTCGACGGGCATCTGCCGGCGATTCTCAACGCG

ATCGAGACCACCAACCAGGGCAACCGGCTGGTGCTCGAAGTGGCT

CAGCATCTCGGCGAGAACACCGTGCGCTGCATCGCCATGGATGCC

ACTGAAGGCCTGGTGCGTGGCCAGGAGGTGGCCGACACCGATGCG
```

-continued

```
CCCATCCAGGTGCCCGTGGGCGCCGCCACCCTCGGCCGCATCATG

AACGTGATCGGCGAGCCGGTGGACGAGCTGGGCCCCATCGAGGGC

GAAGCGCTGCGCGGCATCCATCAGCCGGCCCCCTCCTATGCGGAG

CAGGCCACGGAAGCTGAGATCCTCGTCACCGGCATCAAGGTGGTG

GATCTGCTGGCGCCCTATTCCAAGGGCGGCAAGGTGGGCCTGTTC

GGCGGCGCCGGCGTGGGCAAGACCGTGCTCATCATGGAGCTGATC

AACAACGTGGCCAAGGCGCACGGCGGCTATTCCGTGTTCGCCGGC

GTGGGTGAGCGCACCCGCGAGGGCAACGACCTCTACCACGAGATG

ATCGAGTCCAACGTGAACAAGGACCCGCACGAGAACAATGGCTCG

GCGGCCGGTTCCAAGTGCGCCCTGGTCTATGGCCAGATGAACGAG

CCGCCCGGCGCCCGCGCCCGCGTGGCCCTCACCGGCCTCACCGTC

GCCGAGCATTTCCGCGACCAGGGCCAGGACGTGCTGTTCTTCGTG

GACAACATCTTCCGCTTCACCCAGGCGGGCTCCGAGGTGTCGGCG

CTTCTCGGCCGCATCCCCTCGGCGGTGGGCTACCAGCCGACGCTG

GCCACCGACATGGGCCAGCTGCAGGAGCGCATCACCACCACCACC

AAGGGCTCCATCACCTCGGTGCAGGCCATCTACGTGCCGGCGGAC

GATCTGACCGATCCGGCGCCGGCCGCCTCCTTCGCCCATCTGGAC

GCCACCACGGTGCTGTCGCGCTCCATCGCGGAGAAGGGCATCTAC

CCGGCGGTGGATCCGCTGGACTCCACCTCGCGCATGCTGTCTCCC

GCCATCCTCGGCGACGAGCACTACAACACCGCGCGCCAGGTGCAG

CAGACCCTGCAGCGCTACAAGGCGCTCCAGGACATCATCGCCATC

CTGGGCATGGACGAACTCTCCGAAGAGGACAAGCTCACCGTGGCC

CGCGCCCGCAAGATCGAGCGCTTCCTCTCCCAGCCCTTCCACGTG

GCCGAGGTGTTCACCGGTTCGCCCGGCAAGCTGGTCGACCTCGCC

GACACCATCAAGGGCTTCAAGGGCCTGGTGGACGGCAAGTACGAC

TACCTGCCCGAGCAGGCCTTCTACATGGTGGGCACCATCGAAGAA

GCCATCGAGAAGGGCAAGAAGCTGGCGGCCGAGGCGGCCTGA
```

SEQ ID NO: 33:
Amino acid sequence of ATP synthase subunit
beta atpD_2
```
MANKVGRITQIIGAVVDVQFDGHLPAILNAIETTNQGNRLVLEVA

QHLGENTVRCIAMDATEGLVRGQEVADTDAPIQVPVGAATLGRIM

NVIGEPVDELGPIEGEALRGIHQPAPSYAEQATEAEILVTGIKVV

DLLAPYSKGGKVGLFGGAGVGKTVLIMELINNVAKAHGGYSVFAG

VGERTREGNDLYHEMIESNVNKDPHENNGSAAGSKCALVYGQMNE

PPGARARVALTGLTVAEHFRDQGQDVLFFVDNIFRFTQAGSEVSA

LLGRIPSAVGYQPTLATDMGQLQERITTTTKGSITSVQAIYVPAD

DLTDPAPAASFAHLDATTVLSRSIAEKGIYPAVDPLDSTSRMLSP

AILGDEHYNTARQVQQTLQRYKALQDIIAILGMDELSEEDKLTVA

RARKIERFLSQPFHVAEVFTGSPGKLVDLADTIKGFKGLVDGKYD

YLPEQAFYMVGTIEEAIEKGKKLAAEAA
```

-continued

-continued

SEQ ID NO: 34:
Nucleotide sequence of ATP synthase gamma
chain atpG_2
ATGGCGAGTCTGAAGGACCTGAGAAACCGCATTGCCTCGGTGAAG

GCGACGCAGAAGATCACCAAGGCGATGCAGATGGTCGCCGCGGCG

AAGCTGCGTCGCGCCCAGGCGGCGGCTGAAGCGGCCCGTCCCTAT

GCGGAACGCATGGAGACGGTGCTCGGAAATCTTGCCTCCGGCATG

GTGGTGGGCGCGCAGGCGCCTGTTCTCATGACCGGGACGGGCAAG

AGCGACACCCACCTGCTGCTGGTGTGCACCGGCGAGCGCGGCCTG

TGCGGCGCCTTCAACTCGTCCATCGTGCGCTTCGCCCGCGAGCGG

GCGCAGCTGCTGCTGGCCGAGGGCAAGAAGGTGAAAATCCTGTGC

GTGGGCCGCAAGGGCCACGAGCAGCTGCGCCGCATCTACCCGGAC

AACATCATCGACGTGGTGGACCTGCGCGCGGTGCGCAACATCGGC

TTCAAGGAGGCCGACGCCATCGCCCGCAAGGTGCTGGCCCTGCTC

GATGAAGGCGCATTCGACGTCTGCACGCTCTTCTACTCCCACTTC

AGGAGCGTGATCGCCCAGGTGCCGACGGCCCAGCAGCTCATTCCG

GCCACCTTCGACGAGCGGCCGGCCGTCGCCGATGCGCCGGTCTAT

GAATATGAGCCGGAGGAGGAGGAGATCCTCGCCGAGCTGCTGCCG

CGCAACGTGGCGGTGCAGATCTTCAAGGCCCTCCTCGAGAACCAG

GCTTCTTTCTATGGCTCCCAGATGAGCGCCATGGACAACGCCACG

CGCAATGCGGGCGAGATGATCAAGAAGCAGACGCTCACCTACAAC

CGTACCCGCCAGGCCATGATCACGAAGGAACTCATCGAGATCATC

TCCGGCGCCGAGGCCGTCTGA

SEQ ID NO: 35:
Amino acid sequence of ATP synthase gamma
chain atpG_2
MASLKDLRNRIASVKATQKITKAMQMVAAAKLRRAQAAAEAARPY

AERMETVLGNLASGMVVGAQAPVLMTGTGKSDTHLLLVCTGERGL

CGAFNSSIVRFARERAQLLLAEGKKVKILCVGRKGHEQLRRIYPD

NIIDVVDLRAVRNIGFKEADAIARKVLALLDEGAFDVCTLFYSHF

RSVIAQVPTAQQLIPATFDERPAVADAPVYEYEPEEEEILAELLP

RNVAVQIFKALLENQASFYGSQMSAMDNATRNAGEMIKKQTLTYN

RTRQAMITKELIEIISGAEAV

SEQ ID NO: 36:
Nucleotide sequence of ATP synthase subunit
alpha atpA_2
ATGGACATTCGAGCCGCTGAAATCTCTGCCATCCTGAAAGAGCAG

ATCCAGAATTTCGGCCAGGAGGCGGAAGTCTCCGAGGTGGGTCAG

GTTCTGTCCGTGGGTGACGGCATCGCGCGCGTCTACGGCCTCGAC

AACGTCCAGGCGGGCGAGATGGTCGAGTTCGAGAACGGCACGCGC

GGCATGGCGCTGAACCTCGAGCTCGACAATGTCGGCATCGTGATC

TTCGGTTCCGACCGCGAGATCAAGGAAGGCCAGACCGTCAAGCGG

ACCGGCGCCATCGTGGACGCCCCCGTCGGCAAGGGCCTGCTCGGC

CGCGTCGTGGACGCTCTCGGCAACCCGATCGACGGCAAGGGCCCG

ATCATGTTCACCGAGCGTCGCCGGGTCGACGTGAAGGCGCCGGGC

ATCATCCCGCGCAAGTCGGTGCACGAGCCCATGCAGACCGGCCTG

AAGGGCCATCGATGCGCTCATCCCCATCGGCCGCGGCCAGCGCGAG

CTCATCATCGGCGACCGCCAGACCGGCAAGACCGCCGTGGCGCTC

GACTCGATCCTGAACCAGAAGCCCATCAACCAGGGCGACGACGAG

AAGGCCAAGCTCTACTGCGTCTATGTCGCGGTGGGCCAGAAGCGT

TCCACTGTCGCGCAGTTCGTGAAGGTGCTCGAGGAGCACGGCGCG

CTGGAATATTCCATCGTCGTCGCCGCCACCGCCTCGGACGCGGCC

CCCATGCAGTTCCTGGCGCCGTTCACCGGCACCGCCATGGGCGAG

TATTTCCGCGACAACGGCATGCACGCCCTCATCATCCATGATGAC

CTGTCCAAGCAGGCCGTGGCCTACCGCCAGATGTCGCTGCTGCTG

CGCCGCCCGCCGGGCCGCGAGGCCTATCCCGGCGATGTGTTCTAC

CTGCACTCCCGCCTCTTGGAGCGCGCCGCCAAGCTCAATGACGAG

CACGGCGCCGGCTCGCTGACCGCCCTGCCGGTGATCGAGACCCAG

GCCAACGACGTGTCGGCCTACATCCCGACCAACGTGATCTCCATC

ACCGACGGTCAGATCTTCCTTGAATCCGATCTGTTCTACCAGGGC

ATCCGCCCGGCGGTGAACGTGGGCCTGTCGGTGTCGCGCGTGGGC

TCTTCGGCCCAGATCAAGGCGATGAAGCAGGTGGCCGGCAAGATC

AAGGGCGAGCTCGCCCAGTATCGCGAGCTGGCCGGCCTTCGCCCAG

TTCGGTTCGGACCTGGACGCGGCCCACCCAGAAGCTGCTGAACCGC

GGCGCCCGCCTCACCGAGCTGCTGAAGCAGAGCCAGTTCTCGCCC

CTCAAGGTGGAGGAGCAGGTGGCCGGTGATCTATGCCGGCACCAAT

GGCTATCTCGATCCGCTGCCCGGTCTCCAAGGTGCGCGAGTTCGAG

CAGGGTCTGCTCCTGTCGCTGCGCTCGCAGCATCCGGAGATCCTG

GACGCCATCCGCACGTCCAAGGAGCTTTCCAAGGACACCGCCGAG

AAGCTGACGAAGGCCATCGACGCCTTCGCCAAGAGCTTCTCCTGA

SEQ ID NO: 37:
Amino acid sequence of ATP synthase subunit
alpha atpA_2
MDIRAAEISAILKEQIQNFGQEAEVSEVGQVLSVGDGIARVYGLD

NVQAGEMVEFENGTRGMALNLELDNVGIVIFGSDREIKEGQTVKR

TGAIVDAPVGKGLLGRVVDALGNPIDGKGPIMFTERRRVDVKAPG

IIPRKSVHEPMQTGLKAIDALIPIGRGQRELIIGDRQTGKTAVAL

DSILNQKPINQGDDEKAKLYCVYVAVGQKRSTVAQFVKVLEEHGA

LEYSIVVAATASDAAPMQFLAPFTGTAMGEYFRDNGMHALIIHDD

LSKQAVAYRQMSLLLRRPPGREAYPGDVFYLHSRLLERAAKLNDE

HGAGSLTALPVIETQANDVSAYIPTNVISITDGQIFLESDLFYQG

IRPAVNVGLSVSRVGSSAQIKAMKQVAGKIKGELAQYRELAAFAQ

FGSDLDAATQKLLNRGARLTELLKQSQFSPLKVEEQVAVIYAGTN

GYLDPLPVSKVREFEQGLLLSLRSQHPEILDAIRTSKELSKDTAE

KLTKAIDAFAKSFS

SEQ ID NO: 38:
Nucleotide sequence of ATP synthase subunit
delta atpH

GTGGCGGAAACGATCGTGTCAGGCATGGCGGGACGCTATGCGACC

GCGCTGTTCGAGCTGGCGGACGAAGCCGGTGCCATCGATTCCGTC

CAGGCGGATCTTGATCGCCTGTCCGGCCTTCTGGCCGAGAGCGCG

GATCTGGCGCGGCTGGTCAAGAGCCCGGTCTTCACCGCCGAGCAG

CAGCTCGGCGCGATGGCGGCCATTCTCGATCAAGCAGGCATTTCC

GGCCTTGCGGGCAAATTCGTGAAGCTGGTGGCGCAGAACCGCCGC

CTGTTCGCACTGCCGCGCATGATTGCCGAATACGCCGTCCTGGTG

GCCCGGAAGAAGGGCGAGACCTCGGCGAGCGTGACCGTTGCCACC

CCCCTGAGCGATGAGCATCTGGCCACGCTCAAGGCGGCCCTGGCT

GAAAAGACCGGCAAGGACGTGAAGCTCGACGTCACCGTCGATCCG

TCCATCCTCGGTGGTCTCATCGTGAAGCTCGGCTCGCGCATGGTC

GATGCTTCCCTGAAGACCAAACTCAATTCTATCCGGCATGCGATG

AAAGAGGTCCGCTGA

SEQ ID NO: 39:
Amino acid sequence of ATP synthase subunit
delta atpH
MAETIVSGMAGRYATALFELADEAGAIDSVQADLDRLSGLLAESA

DLARLVKSPVFTAEQQLGAMAAILDQAGISGLAGKFVKLVAQNRR

LFALPRMIAEYAVLVARKKGETSASVTVATPLSDEHLATLKAALA

EKTGKDVKLDVTVDPSILGGLIVKLGSRMVDASLKTKLNSIRHAM

KEVR

SEQ ID NO: 40:
Nucleotide sequence of ATP synthase subunit
b atpF_2
ATGACCGAAATGGAACTGGCTGAGCTCTGGGTCGCCATCGCCTTC

CTGGTTTTCGTAGGCCTCCTGATCTATGCGGGCGCCCACCGCGCC

ATCGTCTCCGCCCTGGATTCCCGCGGCTCGCGCATCGCCTCGGAA

CTGGAGGAGGCCCGTCGGCTCAAGGAAGAGGCCCAGAAGCTGGTG

GCCGAATTCAAGCGCAAGCAGCGCGAGGCCGAGGCCGAGGCCGAA

TCCATCGTCACCGGCGCCAAGGCCGAGGCCGAGCGCCTCGCCGCC

GAGGCCAAGGCGAAGATCGAGGATTTCGTCACCCGCCGCACCAAG

ATGGCCGAGGACAAGATCGCCCAGGCCGAGCATCAGGCTCTGGCG

GACGTGAAGTCCATCGCCGCCGAGGCGGCGGCCAAGGCGGCCGAG

GTGATCCTCGGCGCCCAGGCCACCGGCGCGGTGGCGGAGCGTCTG

CTGTCGGGCGCCATCTCCGAGGTCAAGACCAAGCTCAACTGA

SEQ ID NO: 41:
Amino acid sequence of ATP synthase subunit
b atpF_2
MTEMELAELWVAIAFLVFVGLLIYAGAHRAIVSALDSRGSRIASE

LEEARRLKEEAQKLVAEFKRKQREAEAEAESIVTGAKAEAERLAA

EAKAKIEDFVTRRTKMAEDKIAQAEHQALADVKSIAAEAAAKAAE

VILGAQATGAVAERLLSGAISEVKTKLN

SEQ ID NO: 42:
Nucleotide sequence of ATP synthase subunit
b' atpG_3
ATGATGATTGCATGGAAGCGGACCTTCGCAGTCGTGACCTTCGGG

GCCGCCCTGATGGCCATGCCCGTCGCGGGCGTGGTCGCAGCTGAG

ACTTCTCCCGCTCCGGCGGCAGTGGCGCAGGCCGATCATGCGGTG

CCCACCGAGGCGGCCGGCCAGGGCACCGCCGATGCGGCCCATGCC

GCCGCGCCGGGCGAGGCCGCCCATGGTGGCGCGGCCAAGCACGAA

ACCCATTTCCCGCCCTTCGACGGCACCACCTTCGCCTCCCAGTTG

CTGTGGCTCGCCGTCACCTTCGGCCTGCTTTACTACCTCATGAGC

AAGGTCACGCTGCCGCGCATCGGCCGCATCCTGGAAGAGCGCCAC

GACCGCATCGCCGATGATCTGGAGGAAGCCTCCAAGCATCGCGCC

GAGAGCGAGGCCGCCCAGCGGGCCTATGAGAAGGCGCTGAGCGAG

GCCCGCGCGAAGGCCCATTCCATCGCCGCGGAAACCCGCGACCGC

CTTGCCGCCCACGCCGACACCAACCGCAAGGCGCTGGAGAGCGAG

CTCACCGCCAAGCTGCAGGCGGCCGAGGAGCGCATCGCCACCACC

AAGAGCGAAGCCCTCACCCATGTGCGCGGCATCGCGGTGGACGCC

ACCCAATCCATCGTCTCCACCCTCATCGGTGTCGCGCCCGCGGCG

GCCGACGTGGAAAAAGCGGTGGACGGCGCCCTGTCCCAGCACGGC

CAGGCCTGA

SEQ ID NO: 43:
Amino acid sequence of ATP synthase subunit
b' atpG_3
MMIAWKRTFAVVTFGAALMAMPVAGVVAAETSPAPAAVAQADHAV

PTEAAGQGTADAAHAAAPGEAAHGGAAKHETHFPPFDGTTFASQL

LWLAVTFGLLYYLMSKVTLPRIGRILEERHDRIADDLEEASKHRA

ESEAAQRAYEKALSEARAKAHSIAAETRDRLAAHADTNRKALESE

LTAKLQAAEERIATTKSEALTHVRGIAVDATQSIVSTLIGVAPAA

ADVEKAVDGALSQHGQA

SEQ ID NO: 44:
Nucleotide sequence of ATP synthase subunit
c atpE_2
ATGGAAGCGGAAGCTGGAAAGTTCATCGGTGCCGGCCTCGCCTGC

CTCGGCATGGGTCTCGCTGGCGTCGGCGTCGGTAACATCTTCGGT

AACTTCCTCTCCGGCGCCCTGCGCAACCCGTCCGCTGCCGACGGC

CAGTTCGCCCGCGCCTTCATCGGCGCCGCCCTCGCGGAAGGTCTC

GGCATCTTCTCGCTGGTCGTTGCGCTCGTCCTGCTGTTCGTGGCC

TGA

SEQ ID NO: 45:
Amino acid sequence of ATP synthase subunit
c atpE_2
MEAEAGKFIGAGLACLGMGLAGVGVGNIFGNFLSGALRNPSAADG

QFARAFIGAALAEGLGIFSLVVALVLLFVA

SEQ ID NO: 46:
Nucleotide sequence of ATP synthase subunit
a atpB_2
ATGACCGTCGATCCGATCCACCAGTTCGAGATCAAGCGCTACGTG

GATCTGCTGAACGTCGGCGGTGTCCAGTTCTCCTTCACCAACGCA

ACGGTGTTCATGATTGGCATCGTCCTGGTGATTTTCTTCTTCCTG

ACTTTCGCGACACGCGGTCGCACCCTTGTGCCGGGCCGGATGCAG

TCGGCGGCGGAGCTGAGCTACGAGTTCATCGCCAAGATGGTGCGC

```
-continued
GACGCGGCCGGCAGCGAGGGAATGGTGTTCTTTCCCTTCGTCTTC

TCGCTCTTCATGTTCGTGCTGGTGGCGAACGTATTGGGGCTCATC

CCCTACACCTTCACGGTGACCGCCCACCTCATCGTCACCGCCGCC

CTGGCGGCGACGGTGATCCTCACCGTCATCATCTACGGCTTCGTG

CGGCACGGCACCCACTTCCTGCACCTGTTCGTGCCGTCGGGCGTG

CCGGGCTTCCTCCTGCCCTTCCTCGTGGTGATCGAGGTGGTGTCG

TTCCTGTCGCGGCCCATCAGCCTCTCGCTGCGTCTGTTCGCCAAC

ATGCTGGCGGGCCACATCGCCCTCAAGGTGTTCGCCTTCTTCGTC

GTGGGACTGGCCTCGGCCGGCGCGATCGGCTGGTTCGGCGCCACC

CTGCCCTTCTTCATGATCGTGGCGCTCACCGCGCTGGAGCTGCTG

GTGGCGGTGCTGCAGGCCTACGTGTTCGCGGTGCTGACCTCGATC

TACCTCAACGACGCCATCCATCCCGGCCACTGA

SEQ ID NO: 47:
Amino acid sequence of ATP synthase subunit
a atpB_2
MTVDPIHQFEIKRYVDLLNVGGVQFSFTNATVFMIGIVLVIFFFL

TFATRGRTLVPGRMQSAAELSYEFIAKMVRDAAGSEGMVFFPFVF

SLFMFVLVANVLGLIPYTFTVTAHLIVTAALAATVILTVIIYGFV

RHGTHFLHLFVPSGVPGFLLPFLVVIEVVSFLSRPISLSLRLFAN

MLAGHIALKVFAFFVVGLASAGAIGWFGATLPFFMIVALTALELL

VAVLQAYVFAVLTSIYLNDAIHPGH

SEQ ID NO: 48:
Nucleotide sequence of ATP synthase protein
I atpI
ATGTCCGAGCCGAATGATCCATCCCGCAGGGACGGTGCGAAGGCG

AAAGACGAGACGCAGGACTCCCGGCCCGGTGAGGCGGATCTTGCT

CGGCGCCTCGATGCGCTCGGCACCTCCATCGGTCAGGTCAAGTCC

AGAAGCGGGGAGCCCGCGGCGACGCCGCGCAAGGACACCTCCTCG

GCCTCCGGCGCGGCCCTGGCGTTTCGGCTGGGCGCCGAGTTTGTT

TCAGGCGTGCTGGTGGGCTCGCTCATCGGCTACGGGTTGGATTAT

GCGTTTGCGATTTCGCCCTGGGGGCTGATCGCCTTCACGCTGATC

GGCTTTGCCGCCGGCGTCCTGAACATGCTGCGCGTGGCGAACAGC

GATGCCAAGCGCCACAGCGCGGACAGGTGA

SEQ ID NO: 49:
Amino acid sequence of ATP synthase protein
I atpI
MSEPNDPSRRDGAKAKDETQDSRPGEADLARRLDALGTSIGQVKS

RSGEPAATPRKDTSSASGAALAFRLGAEFVSGVLVGSLIGYGLDY

AFAISPWGLIAFTLIGFAAGVLNMLRVANSDAKRHSADR
```

In another embodiment, the bacterial strain used in the process of the invention comprises a gene encoding a nitrogenase molybdenum-iron protein alpha chain nifD_1 having the sequence set forth in SEQ ID NO:51 or a sequence having more than 60% identity, e.g. more than 70% identity, such as more than 92% identity, such as more than 95% identity, e.g. more than 96% identity, such as more than 97% identity, e.g. more than 98%, such as more than 99% sequence identity to the sequence set forth in SEQ ID NO:51.

In another embodiment, the bacterial strain used in the process of the invention comprises a gene encoding nitrogenase molybdenum-iron protein alpha chain nifD_2 having the sequence set forth in SEQ ID NO:53 or a sequence having more than 60% identity, e.g. more than 98%, such as more than 99% sequence identity to the sequence set forth in SEQ ID NO:53.

In another embodiment, the bacterial strain used in the process of the invention comprises a gene encoding a nitrogenase molybdenum-iron protein beta chain nifK_1 having the sequence set forth in SEQ ID NO:55 or a sequence having more than 87% identity, e.g. more than 90% identity, such as more than 95% identity, e.g. more than 96% identity, such as more than 97% identity, e.g. more than 98%, such as more than 99% sequence identity to the sequence set forth in SEQ ID NO:55.

In another embodiment, the bacterial strain used in the process of the invention comprises a gene encoding a nitrogenase molybdenum-iron protein beta chain nifK_2 having the sequence set forth in SEQ ID NO:57 or a sequence having more than 95% identity, e.g. more than 96% identity, such as more than 97% identity, e.g. more than 98%, such as more than 99% sequence identity to the sequence set forth in SEQ ID NO:57.

In another embodiment, the bacterial strain used in the process of the invention comprises a gene encoding a nitrogenase iron protein nifH having the sequence set forth in SEQ ID NO:59 or a sequence having more than 98.5% sequence identity to the sequence set forth in SEQ ID NO:59.

```
SEQ ID NO: 50:
Nucleotide sequence of Nitrogenase
molybdenum-iron protein alpha chain nifD_1
ATGAGTTCGCTCTCCGCCACTATTCAACAGGTCTTCAACGAGCCG

GGCTGCGCGAAGAACCAGAATAAGTCCGAGGCGGAGAAGAAGAAG

GGCTGCACCAAGCAGCTGCAACCCGGCGGAGCGGCCGGCGGCTGC

GCGTTCGACGGCGCGAAGATCGCGCTCCAGCCCTTGACCGACGTC

GCCCACCTGGTGCACGGCCCCATCGCCTGCGAAGGCAATTCCTGG

GACAATCGTGGCGCCAAGTCCTCCGGCTCGAACATCTGGCGCACC

GGCTTCACCACGGACATCAACGAAACCGACGTGGTGTTCGGCGGC

GAGAAGCGTCTGTTCAAGTCCATCAAGGAAATCATCGAGAAGTAC

GACCCGCCGGCCGTCTTCGTCTATCAGACCTGCGTCCCCGCCATG

ATCGGCGACGACATCGACGCGGTGTGCAAGGCGGCCAGGGAGAAG

TTCGGAAAGCCGGTGATCCCGATCAATTCCCCCGGCTTCGTGGGG

CCGAAGAATCTCGGCAACAAGCTCGCCGGCGAGGCGCTCCTCGAC

CATGTGATCGGCACCGAGGAGCCCGATTACACGACGGCCTACGAC

ATCAACATCATCGGCGAATACAATCTCTCCGGCGAGTTGTGGCAG

GTGAAGCCGCTGCTGGACGAGCTGGGCATCCGCATCCTCGCCTGC

ATCTCCGGCGACGGGAAGTACAAGGATGTGGCGTCCTCCCACCGC

GCCAAGGCGGCGATGATGGTGTGCTCCAAGGCCATGATCAACGTG

GCCCGCAAGATGGAGGAGCGCTACGACATCCCCTTCTTCGAAGGC

TCCTTCTACGGCATCGAGGATAGCTCCGATTCCCTGCGCGAGATT

GCGCGCATGCTCATCGAGAAGGGCGCCGATCCGGAGCTGATGGAC
```

-continued

```
CGCACCGAGGCGCTGATTGAGCGGGAAGAGAAGAAGGCGTGGGAC

GCCATCGCCGCCTACAAGCCCCGCTTCAAGGACAAGAAGGTGCTG

CTCATCACCGGCGGCGTGAAATCCTGGTCGGTGGTGGCAGCGCTC

CAGGAAGCCGGCCTCGAACTGGTGGGCACCTCGGTGAAGAAGTCC

ACCAAGGAGGACAAGGAGCGCATCAAGGAACTGATGGGCCAGGAC

GCCCACATGATCGACGACATGACGCCCCGCGAAATGTACAAGATG

CTGAAGGACGCCAAGGCGGACATCATGCTCTCGGGCGGGCGCTCG

CAATTCATCGCGCTCAAGGCCGCCATGCCCTGGCTCGACATCAAC

CAGGAGCGCCACCACGCCTATATGGGCTATGTGGGCATGGTGAAG

CTGGTCGAGGAGATCGACAAGGCGCTCTACAATCCCGTGTGGGAA

CAGGTGCGCAAGCCCGCCCCGTGGGAAAATCCGGAAGACACCTGG

CAGGCCCGTGCGCTCGCCGAAATGGAGGCGGAGGCCGCCGCGCTC

GCCGCCGATCCGGTGCGCGCGGAAGAGGTGCGCCGGTCCAAGAAG

ATCTGCAATTGCAAGAGCGTCGACCTCGGAACCATTGAGGACGCC

ATCAAGGCTCACGCGCTGACCACCGTGGAGGGTGTGCGAGAGCAC

ACCAATGCCTCGGGAGGCTGCGGAGCCTGCAGCGGGCGGATCGAG

GAGATCTTCGAGGCCGTGGGCGTTGTCGCCGCCCCGCCTCCCGCG

GAGGCCGCCCCGTCTCCGCAGGAGATCGCGCCCGATCCGCTCGCT

GCGGAGGAAAAGCGCCGCGCCAAGAAGGCCTGCGGCTGCAAGGAG

GTAGCGGTCGGCACCATTGAGGATGCCATCCGCGCGCCAAGGGTCTG

CGAAACATCGCGGAGGTGCGTGCGGCCACCGATGCCAACACCGGC

TGCGGCAATTGCCAGGAGCGGGTGGAGGGCATCCTCGACCGGGTT

CTCGCCGAGGCGGCCTCAGAACTCCAGGCGGCGGAATAG
```

SEQ ID NO: 51:
Amino acid sequence of Nitrogenase
molybdenum-iron protein alpha chain nifD_1
MSSLSATIQQVFNEPGCAKNQNKSEAEKKKGCTKQLQPGGAAGGC

AFDGAKIALQPLTDVAHLVHGPIACEGNSWDNRGAKSSGSNIWRT

GFTTDINETDVVFGGEKRLFKSIKEIIEKYDPPAVFVYQTCVPAM

IGDDIDAVCKAAREKFGKPVIPINSPGFVGPKNLGNKLAGEALLD

HVIGTEEPDYTTAYDINIIGEYNLSGELWQVKPLLDELGIRILAC

ISGDGKYKDVASSHRAKAAMMVCSKAMINVARKMEERYDIPFFEG

SFYGIEDSSDSLREIARMLIEKGADPELMDRTEALIEREEKKAWD

AIAAYKPRFKDKKVLLITGGVKSWSVVAALQEAGLELVGTSVKKS

TKEDKERIKELMGQDAHMIDDMTPREMYKMLKDAKADIMLSGGRS

QFIALKAAMPWLDINQERHHAYMGYVGMVKLVEEIDKALYNPVWE

QVRKPAPWENPEDTWQARALAEMEAEAAALAADPVRAEEVRRSKK

ICNCKSVDLGTIEDAIKAHALTTVEGVREHTNASGGCGACSGRIE

EIFEAVGVVAAPPPAEAAPSPQEIAPDPLAAEEKRRAKKACGCKE

VAVGTIEDAIRAKGLRNIAEVRAATDANTGCGNCQERVEGILDRV

LAEAASELQAAE

-continued

SEQ ID NO: 52:
Nucleotide sequence of Nitrogenase
molybdenum-iron protein alpha chain nifD_2

```
ATGAGTGTCGCACAGTCCCAGAGCGTCGCCGAGATCAAGGCGCGC

AACAAGGAACTCATCGAAGAGGTCCTCAAGGTCTATCCCGAGAAG

ACCGCCAAGCGCCGCGCCAAGCACCTGAACGTCCACGAAGCCGGC

AAGTCCGACTGCGGCGTGAAGTCCAACATCAAGTCCATCCCGGGC

GTGATGACCATCCGCGGTTGCGCTTATGCCGGCTCCAAGGGTGTG

GTGTGGGGTCCCATCAAGGACATGATCCACATCTCCCACGGCCCG

GTGGGCTGCGGCCAGTATAGCTGGGCCGCCCGCCGCAACTACTAT

ATCGGCACGACCGGCATCGACACCTTCGTGACGATGCAGTTCACC

TCCGACTTCCAGGAGAAGGACATCGTCTTCGGCGGCGACAAGAAG

CTCGCCAAGATCATGGACGAGATCCAGGAGCTGTTCCCGCTGAAC

AACGGCATCACCGTTCAGTCCGAGTGCCCCATCGGCCTCATCGGC

GACGACATCGAGGCCGTCTCCAAGCAGAAGTCCAAGGAGTATGAG

GGCAAGACCATCGTGCCGGTGCGCTGCGAGGGCTTCCGCGGCGTG

TCCCAGTCCCTGGGCCACCACATCGCCAACGACGCCATCCGCGAT

TGGGTGTTCGACAAGATCGCGCCCGACGCCGAGCCGCGCTTTGAG

CCGACCCCGTACGACGTCGCCATCATCGGCGACTACAATATCGGT

GGTGACGCCTGGTCGTCCCGTATCCTCCTGGAGGAGATGGGCCTG

CGCGTGATCGCCCAGTGGTCCGGCGACGGTTCGCTCGCTGAGCTG

GAGGCCACCCCGAAGGCCAAGCTCAACGTGCTGCACTGCTACCGC

TCCATGAACTACATCTCGCGCCACATGGAAGAGAAGTACGGTATC

CCGTGGTGCGAGTACAACTTCTTCGGTCCTTCCAAGATCGCCGAG

TCCCTGCGCAAGATCGCCAGCTACTTCGACGACAAGATCAAGGAA

GGCGCGGAGCGCGTCATCGCCAAGTATCAGCCGCTCATGGATGCG

GTGATCGCGAAGTATCGTCCCCGCCTCGAGGGCAAGACCGTGATG

CTGTACGTGGGCGGCCTGCGTCCCCGTCACGTCATCGGCGCCTAC

GAGGACCTGGGCATGGAAGTGGTCGGCACGGGCTACGAGTTCGCC

CATAACGACGACTACCAGCGCACCGCCCAGCACTACGTCAAGGAT

GGCACCATCATCTATGACGACGTGACCGGCTACGAGTTCGAGAAG

TTCGTCGAGAAGATCCAGCCGGACCTGGTCGGTTCGGGCATCAAG

GAAAAGTACGTCTTCCAGAAGATGGGCGTGCCGTTCCGCCAGATG

CACTCCTGGGACTACTCGGGCCCGTACCACGGCTATGACGGCTTC

GCGATCTTCGCGCGCGACATGGACATGGCCATCAACAGCCCCGTG

TGGAAGATGACCCAGGCTCCGTGGAAGAGCGTCCCCAAGCCGACG

ATGCTCGCGGCTGAATGA
```

SEQ ID NO: 53:
Amino acid sequence of Nitrogenase
molybdenum-iron protein alpha chain nifD_2
MSVAQSQSVAEIKARNKELIEEVLKVYPEKTAKRRAKHLNVHEAG

KSDCGVKSNIKSIPGVMTIRGCAYAGSKGVVWGPIKDMIHISHGP

VGCGQYSWAARRNYYIGTTGIDTFVTMQFTSDFQEKDIVFGGDKK

-continued

LAKIMDEIQELFPLNNGITVQSECPIGLIGDDIEAVSKQKSKEYE

GKTIVPVRCEGFRGVSQSLGHHIANDAIRDWVFDKIAPDAEPRFE

PTPYDVAIIGDYNIGGDAWSSRILLEEMGLRVIAQWSGDGSLAEL

EATPKAKLNVLHCYRSMNYISRHMEEKYGIPWCEYNFFGPSKIAE

SLRKIASYFDDKIKEGAERVIAKYQPLMDAVIAKYRPRLEGKTVM

LYVGGLRPRHVIGAYEDLGMEVVGTGYEFAHNDDYQRTAQHYVKD

GTIIYDDVTGYEFEKFVEKIQPDLVGSGIKEKYVFQKMGVPFRQM

HSWDYSGPYHGYDGFAIFARDMDMAINSPVWKMTQAPWKSVPKPT

MLAAE

SEQ ID NO: 54:
Nucleotide sequence of Nitrogenase
molybdenum-iron protein beta chain nifK_1
ATGGCCACCGTTTCCGTCTCCAAGAAGGCCTGCGCGGTCAACCCC

CTCAAGATGAGCCAGCCGGTGGGCGGCGCGCTCGCCTTCATGGGC

GTGCGCAAGGCCATGCCGCTGCTGCACGGCTCGCAGGGCTGCACC

TCCTTCGGCCTGGTGCTGTTCGTGCGCCACTTCAAGGAAGCCATC

CCCATGCAGACCACCGCCATGAGCGAGGTGGCGACGGTTCTGGGC

GGCCTTGAGAATGTGGAGCAGGCCATTCTCAACATCTACAATCGC

ACCAAGCCGGAGATCATCGGCATCTGCTCCACCGGCGTCACCGAG

ACCAAGGGCGATGATGTCGACGGCTACATCAAGCTGATCCGGGAC

AAGTATCCCCAGCTGGCCGACTTCCCGCTGGTCTATGTCTCCACC

CCCGATTTCAAGGACGCCTTCCAGGACGGTTGGGAGAAGACCGTG

GCGAAGATGGTGGAGGCGCTGGTGAAGCCCGCCGCCGACAAGCAG

AAGGACAAGACCCGCGTCAACGTCCTGCCCGGCTGCCACCTCACG

CCCGGCGATCTGGATGAGATGCGGACCATCTTCGAGGATTTCGGG

CTCACACCCTATTTCCTGCCGGATCTGGCCGGCTCGCTGGATGGG

CATATCCCCGAGGACTTCTCGCCCACCACCATCGGCGGCATCGGC

ATCGATGAGATCGCCACCATGGGCGAGGCGGCCCACACCATCTGC

ATCGGCGCGCAGATGCGCCGGGCGGGCGAGGCCATGGAGAAGAAG

ACCGGCATTCCCTTCAAGCTGTTCGAGCGCCTGTGCGGCCTGGAG

GCGAACGACGCCTTCATCATGCACCTGTCGCAGATCTCCGGCCGG

CCGGTGCCGGTGAAGTATCGCCGGCAGCGGGGCCAGCTGGTGGAT

GCCATGCTGGACGGCCACTTCCATCTGGGCGGTCGCAAGGTGGCC

ATGGGGGGGGAGCCGGACCTGCTCTACGACGTGGGCTCCTTCCTG

CACGAGATGGGCGCCCACATCCTTTCCGCGGTCACCACCACCCAG

TCGCCGGTGCTGGCGCGCCTGCCTGCCGAGGAGGTGCTTATCGGC

GACCTGGAGGATCTGGAGACCCAGGCGAAGGCGCGCGGATGCGAT

CTCCTGCTCACCCATTCCCATGGGCGCCAGGCGGCGGAGCGCCTC

CACATCCCCTTCTACCGGATCGGCATTCCCATGTTTGACCGGCTG

GGGGCGGGGCATCTGTTGTCGGTGGGCTATCGCGGCACCCGCGAC

CTCATCTTCCATCTCGCCAACCTTGTGATCGCCGACCACGAGGAA

-continued

AATCACGAGCCGACGCCCGACACCTGGGCCACCGGCCATGGCGAG

CATGCCGCCGCCCCCACTTCCCATTGA

SEQ ID NO: 55:
Amino acid sequence of Nitrogenase
molybdenum-iron protein beta chain nifK_1
MATVSVSKKACAVNPLKMSQPVGGALAFMGVRKAMPLLHGSQGCT

SFGLVLFVRHFKEAIPMQTTAMSEVATVLGGLENVEQAILNIYNR

TKPEIIGICSTGVTETKGDDVDGYIKLIRDKYPQLADFPLVYVST

PDFKDAFQDGWEKTVAKMVEALVKPAADKQKDKTRVNVLPGCHLT

PGDLDEMRTIFEDFGLTPYFLPDLAGSLDGHIPEDFSPTTIGGIG

IDEIATMGEAAHTICIGAQMRRAGEAMEKKTGIPFKLFERLCGLE

ANDAFIMHLSQISGRPVPVKYRRQRGQLVDAMLDGHFHLGGRKVA

MGAEPDLLYDVGSFLHEMGAHILSAVTTTQSPVLARLPAEEVLIG

DLEDLETQAKARGCDLLLTHSHGRQAAERLHIPFYRIGIPMFDRL

GAGHLLSVGYRGTRDLIFHLANLVIADHEENHEPTPDTWATGHGE

HAAAPTS H

SEQ ID NO: 56:
Nucleotide sequence of Nitrogenase
molybdenum-iron protein beta chain nifK_2
ATGCCACAAAATGCTGACAATGTGCTCGATCACTTCGAGCTCTTC

CGTGGTCCCGAATACCAGCAGATGCTGGCCAATAAGAAAAAGATG

TTCGAGAACCCCCGCGATCCGGCCGAAGTCGAGCGCGTGCGGGAA

TGGGCGAAGACTCCTGAATACAAGGAGCTGAACTTCGCCCGCGAG

GCGCTCACCGTGAATCCGGCCAAGGCTTGTCAGCCGCTGGGCGCG

GTGTTCGTCGCCGTCGGCTTCGAGAGCACGATCCCCTTCGTGCAC

GGCTCGCAGGGTTGCGTCGCGTATTACCGCTCGCACCTCTCCCGC

CACTTCAAGGAGCCGTCCTCCTGCGTCTCCTCGTCCATGACCGAG

GATGCGGCGGTGTTCGGCGGCCTCAACAACATGATTGACGGCCTC

GCCAACACCTACAACATGTACAAGCCGAAGATGATCGCCGTCTCC

ACCACCTGCATGGCGGAAGTCATCGGCGACGATCTGAACGCCTTC

ATCAAGACCGCGAAGGAAAAGGGCTCGGTTCCGGCCGAATACGAC

GTGCCCTTCGCCCACACCCCGGCCGTTCGTCGGCAGCCATGTCACC

GGCTACGACAATGCGCTCAAGGGCATCCTCGAGCACTTCTGGGAC

GGCAAGGCCGGCACCGCGCCGAAGCTGGAGCGCGTTCCCAACGAG

AAGATCAACTTCATCGGCGGCTTCGACGGCTACACCGTCGGCAAC

ACTCGCGAAGTGAAGCGCATCTTCGAGGCGTTCGGCGCCGATTAC

ACCATCCTCGCCGACAATTCCGAAGTGTTCGACACCCCGACCGAC

GGCGAGTTCCGCATGTATGACGGCGGCACGACCCTGGAGGACGCG

GCGAACGCGGTGCACGCCAAGGCCACCATCTCCATGCAGGAATAC

TGCACGGAGAAGACCCTGCCCATGATCGCCGGTCATGGCCAGGAC

GTGGTCGCCCTCAACCACCCCGTGGGCGTGGGCGGCACCGACAAG

TTCCTCATGGAGATCGCCCGCCTCACCGGCAAGGAGATCCCCGAG

GAGCTGACCCGCGAGCGCGGCCGTCTCGTGGACGCTATCGCGGAC

TCTTCCGCGCACATCCACGGCAAGAAGTTCGCCATCTACGGCGAT

-continued

CCGGATCTGTGCCTGGGCCTCGCCGCGTTCCTGCTGGAGCTGGGC

GCCGAGCCGACCCATGTGCTGGCCACCAACGGCACCAAGAAGTGG

GCCGAGAAGGTTCAGGAACTGTTCGACTCTTCGCCGTTCGGCGCC

AACTGCAAGGTCTATCCCGGCAAGGACCTGTGGCACATGCGCTCG

CTCCTGTTCGTGGAGCCGGTGGATTTCATCATCGGCAACACCTAC

GGCAAGTATCTCGAGCGCGACACGGGCACCCCGCTGATCCGTATC

GGCTTCCCGGTGTTCGACCGTCACCACCACCACCGCCGTCCGGTG

TGGGGCTATCAGGGCGGCATGAACGTCCTGATCACGATCCTCGAC

AAGATCTTTGACGAGATCGACCGCAACACCAACGTGCCGGCCAAG

ACCGACTACTCGTTCGACATCATTCGTTGA

SEQ ID NO: 57:
Amino acid sequence of Nitrogenase
molybdenum-iron protein beta chain nifK_2
MPQNADNVLDHFELFRGPEYQQMLANKKKMFENPRDPAEVERVRE

WAKTPEYKELNFAREALTVNPAKACQPLGAVFVAVGFESTIPFVH

GSQGCVAYYRSHLSRHFKEPSSCVSSSMTEDAAVFGGLNNMIDGL

ANTYNMYKPKMIAVSTTCMAEVIGDDLNAFIKTAKEKGSVPAEYD

VPFAHTPAFVGSHVTGYDNALKGILEHFWDGKAGTAPKLERVPNE

KINFIGGFDGYTVGNTREVKRIFEAFGADYTILADNSEVFDTPTD

GEFRMYDGGTTLEDAANAVHAKATISMQEYCTEKTLPMIAGHGQD

VVALNHPVGVGGTDKFLMEIARLTGKEIPEELTRERGRLVDAIAD

SSAHIHGKKFAIYGDPDLCLGLAAFLLELGAEPTHVLATNGTKKW

AEKVQELFDSSPFGANCKVYPGKDLWHMRSLLFVEPVDFIIGNTY

GKYLERDTGTPLIRIGFPVFDRHHHHRRPVWGYQGGMNVLITILD

KIFDEIDRNTNVPAKTDYSFDIIR

SEQ ID NO: 58:
Nucleotide sequence of Nitrogenase
iron protein nifH
GTGGAGTCCGGTGGTCCTGAGCCGGGCGTGGGCTGCGCCGGCCGC

GGCGTGATCACCTCCATCAACTTCCTGGAGGAGAACGGCGCCTAC

GAGGACATCGACTATGTGTCCTACGACGTGCTGGGCGACGTGGTG

TGCGGCGGCTTCGCCATGCCCATCCGCGAGAACAAGGCGCAGGAA

ATCTACATCGTGATGTCCGGCGAGATGATGGCCATGTATGCGGCC

AACAACATCTCCAAGGGCATCCTGAAGTATGCCAATTCCGGCGGC

GTGCGCCTGGGCGGGCTGGTCTGCAACGAGCGCCAGACCGACAAG

GAGCTGGAGCTGGCGGAGGCTCTGGCGAAGAAGCTCGGCACCGAG

CTGATCTACTTCGTGCCGCGCGACAACATCGTGCAGCATGCCGAG

CTGCGCCGCATGACAGTGATCGAGTATGCGCCCGATTCCGCCCAG

GCCCAGCACTACCGGAACCTGGCCGAGAAGGTGCACGCCAACAAG

GGCAACGGCATCATCCCGACCCCGATCACCATGGACGAGCTGGAA

GACATGCTCATGGAGCACGGCATCATGAAGGCCGTGGACGAGAGC

CAGATCGGCAAGACCGCCGCCGAGCTCGCCGTCTGA

SEQ ID NO: 59:
Amino acid sequence of Nitrogenase

-continued
iron protein nifH
MESGGPEPGVGCAGRGVITSINFLEENGAYEDIDYVSYDVLGDVV

CGGFAMPIRENKAQEIYIVMSGEMMAMYAANNISKGILKYANSGG

VRLGGLVCNERQTDKELELAEALAKKLGTELIYFVPRDNIVQHAE

LRRMTVIEYAPDSAQAQHYRNLAEKVHANKGNGIIPTPITMDELE

DMLMEHGIMKAVDESQIGKTAAELAV

Downstream Processing

In one embodiment, the process of the invention comprises the further step of harvesting biomass produced during the culture. Biomass can e.g. be harvested by sedimentation (settling based on gravity), filtration, centrifugation or flocculation. Flocculation may require the addition of a flocculation agent. Centrifugation may e.g. be carried out using a continuous flow centrifuge.

In one embodiment, the harvested biomass is subsequently dried. Drying can e.g. be performed using well known methods, including centrifugation, drum drying, evaporation, freeze drying, heating, spray drying, vacuum drying and/or vacuum filtration. The dried biomass may subsequently be used in a product, e.g. a food or feed product or feed or food ingredient.

In another embodiment, the cells of the harvested biomass are lysed. The lysate may in some embodiments be separated into insoluble and soluble fractions, either or both of which may subsequently be concentrated or dried, and subsequently be used in a product, e.g. a food or a feed product.

In one embodiment, biomass is harvested and proteins are isolated from said biomass, resulting in a protein fraction and a fraction comprising non-protein components. Thus, in one embodiment, the process is for the production of protein and comprises a step of culturing strain VTT-E-193585 or a derivative thereof, followed by a step of harvesting biomass and a further step of isolating proteins from said biomass. In another embodiment, the process is for the production of protein and comprises culturing a bacterial strain of the genus *Xanthobacter* in continuous culture with hydrogen as energy source and an inorganic carbon source, wherein the inorganic carbon source comprises carbon dioxide, followed by a step of harvesting biomass and a further step of isolating proteins from said biomass. Depending on the method of protein isolation, the resulting fractions may be more pure or less pure. Thus, the term "protein fraction" means a fraction enriched in proteins. The protein fraction may still comprise significant amounts of other components and also significant amounts of protein may end up in the "fraction comprising non-protein components".

Isolation of proteins may be performed using any suitable method. For example, in one embodiment, proteins are isolated by breaking cells mechanically and separating protein from cell debris through one or more filtration steps, e.g. successive filtration through multiple filters with decreasing pore size. Mechanical breaking may be carried out using any suitable method, e.g. ball milling, sonication, homogenization, high pressure homogenization, mechanical shearing, etc. The resulting filtered protein fraction will be enriched in proteins, but also still contain other smaller components. Protein may optionally be further purified from this fraction using any suitable method.

In another embodiment, a protein fraction is isolated by performing ethanol extraction followed by one or more filtration steps. Such methods are e.g. known from the preparation of soy bean proteins (see e.g. Chapter 5 "Soybean Protein Concentrates" in "Technology of production of edible flours and protein products from soybeans" by Berk FAO Agricultural Services Bulletin No. 97 (1992). The resulting protein fraction will be enriched in proteins, but also still contain other components. Protein may optionally be further purified from this fraction using any suitable method.

In one embodiment, the process of the invention comprises the further step of hydrolysing the protein fraction obtained from the process of the invention to obtain amino acids and small peptides.

In one embodiment of the process of the invention, the process comprises the further step of producing a food or feed product from said biomass, from said protein fraction or from said fraction comprising non-protein components. Said further step may simply comprise incorporating said biomass, protein fraction or fraction comprising non-protein components in a food or feed product, by adding it during the production of the food or feed product. In other embodiments, further purification or modification of the biomass or fraction thereof is performed during the course of its incorporation into a food or feed product.

In a further aspect, the invention relates to a product, such as biomass, protein, or non-protein components, obtained or obtainable by the process according to the invention.

In one embodiment, the product obtained from the process of the invention comprises more than 40% protein, such as between 40% and 99% protein, e.g. between 40% and 90% protein, such as between 40% and 60% protein. In a particular embodiment, the product comprises between 25% and 75% protein, between 0% and 20% lipid and between 5% and 40% carbohydrates. In a further embodiment, the product comprises between 40% and 60% protein, between 0% and 15% lipid and between 10% and 25% carbohydrate. In an even further embodiment, the product obtained from the process of the invention comprises between 45% and 55% protein, between 5% and 10% lipid and between 10% and 20% carbohydrates.

As described above, the invention in a further aspect relates to a food or feed product obtained or obtainable by the process according to the invention. When used herein, the terms "food" and "feed" are intended to include not only conventional food and feed products, such as processed foods, but also related products, such as food and feed supplements, e.g. protein bars, powders or shakes, meat replacements, food ingredients, probiotics, prebiotics, nutraceuticals and the like. In certain embodiments, said biomass, said protein fraction or said fraction comprising non-protein components is utilized in the production of a vegetarian or vegan food product.

The invention is further illustrated with the following, non-limiting, examples:

EXAMPLES

Example 1. Isolation of Bacterial Strain Capable of Chemoautotrophic Growth

A sample of 50 mL containing soil and seawater was collected in a sterile falcon tube from the seashore of the Baltic sea in Naantali in Finland. Part of soil sample was mixed with 10 mL of mineral medium in a sterile Erlenmeyer flask. The medium consisted of 1 g/L $NH_4OH$, 0.23 g/L $KH_2PO_4$, 0.29 g/L $Na_2HPO_4$·2 $H_2O$, 0.005 g/L $NaVO_3$·$H_2O$, 0.2 g/L $FeSO_4$·7 $H_2O$, 0.5 g/L $MgSO_4$·7 $H_2O$, 0.01 g/L $CaSO_4$, 0.00015 g/L $Na_2MoO_4$·2 $H_2O$, 0.005 g/L $MnSO_4$, 0.0005 g/L $ZnSO_4$·7 $H_2O$, 0.0015 g/L $H_3BO_3$, 0.001 g/L $CoSO_4$, 0.00005 g/L $CuSO_4$ and 0.0001 g/L $NiSO_4$ prepared in tap water. The suspension of soil and medium was incubated in a shaking incubator in +30° C. temperature in a sealed steel box that was flushed continuously with a gas mixture: 150 mL/min of $N_2$, 18 mL/min of $H_2$, 3 mL/min of $O_2$ and 6 mL/min of $CO_2$. The cultivation was refreshed in seven-day intervals by taking 1 mL of suspension, which was added in sterile conditions to 9 mL of medium in Erlenmeyer flask, and then placed back into the incubation box. After the fourth dilution, there was no noticeable soil left in the suspension. The volume of the cell suspension was increased to 100 mL in order to grow biomass for bioreactor cultivation. The optical density ($OD_{600}$) of the suspension was 1.53 when it was inoculated to 190 mL of mineral medium in 15-vessel 200-mL parallel bioreactor system (Medicel Explorer, Medicel Oy, Finland). The cultivation conditions were 800 rpm agitation, +30° C. temperature and the pH was set to 6.8, controlling it with 1 M NaOH. Gas was fed through a sparger with a gas mixture consisting of 14 mL/min $H_2$, 3 mL/min $O_2$ and 6 mL/min $CO_2$. The head space of the reactor was flushed with 300 mL/min air. Continuous cultivation was fed with mineral medium 6 mL/h and cell suspension was drawn from the reactor via capillary keeping the volume constant at 200 mL. Cell suspension drawn from the reactor was stored at +4° C. A sample was taken from the bioreactor automatically every day, and absorbance at 600 nm was measured to monitor the growth. After 498 hours of bioreactor cultivation, samples were drawn aseptically and suspension was diluted and plated to agar mineral medium plates containing the above minerals and 2% bacteriological agar. Plates were incubated in same conditions as described above for the Erlenmeyer flasks. Colonies were then picked from agar plates and streaked to new agar plates in order to isolate one organism in one colony. This was repeated twice. Single colonies were picked and suspended into 200 µL of medium in a 96-well microtiter plate. The suspension was incubated at +30° C. temperature and shaken 625 rpm in an EnzyScreen gas tight box that was flushed continuously with 150 mL/min of $N_2$, 18 mL/min of $H_2$, 3 mL/min of $O_2$ and 6 mL/min of $CO_2$. The suspension from one well was transferred to an Erlenmeyer flask and supplemented with fresh medium. Volume was increased until there was enough biomass to perform a bioreactor cultivation. The organism was deposited in the VTT culture collection as VTT-E-193585.

16S rRNA sequencing of a sample demonstrated that the sample contained only one organism. The same sample was used for Illumina NextSeq sequencing providing 1×150 bp metagenomic shotgun sequences. Using Unicycler (Wick et al, 2017 PLoS computational biology 13:e1005595), the de novo assembly was made for metagenomic sequences consisting of 101 contigs. The total genome length was 4,846,739 bp and the GC content was 67.9%. Gene predictions and functional annotations were performed using Prokka (Seemann, 2014 Bioinformatics 30:2068). The genome annotation produced 4,429 genes. Roary pan genomic alignment (Page et al, 2015 Bioinformatics 31:3691) grouped VTT-E-193585 among *Xanthobacter* species. The strain was therefore identified as a *Xanthobacter* sp., the closest genome being *Xanthobacter tagetidis*. Alignment-based calculation of average nucleotide identity that takes into account only orthologous fragments (OrthoANI) (Lee et al, 2016 Int J Syst Evol Microbiol 66:1100) gave the best match of 80.4% to *Xanthobacter tagetidis* (ATCC 700314; GCF_003667445.1), whereas the proposed species boundary cut-off is 95-96% (see e.g., Chun et al., 2018 Int J Syst Evol Microbiol, 68: 461-466). *Xanthobacter autotrophicus* Py2 gave a match of 79.6%, while the match for *Xantho-*

*bacter* sp. 91 was 79.0%. It could thus be concluded that the isolated bacterial strain deposited as VTT-E-193585 belongs to the Phylum: Proteobacteria; to the Class: Alpha Proteobacteria; and to the Order: Rhizobiales. The most probable Family is Xanthobacteraceae, and the Genus *Xanthobacter*. The VTT-E-193585 bacterial strain could not be assigned unequivocally to any known species.

A search for putative antimicrobial resistance genes was performed. The ABRicate (https://github.com/tseemann/abricate) tool was used to search the genome against the Arg-Annot, NCBI, ResFinder, the ecOH, Megares and VFDB databases using blastn or blastp. A threshold of 50% was set for both identity and coverage, both on nucleotide and protein level. Only two putative antimicrobial resistance genes were identified. These two genes did not contain amino-acid changes linked to antibiotics resistance and thus a resistant phenotype is not expected.

Example 2. Pilot Cultivation and Analysis of Isolated Bacterial Strain

The isolated bacterial strain deposited as VTT-E-193585 was cultivated in a conventional 200-liter stirred tank bioreactor (MPF-U, Marubishi Ltd, Japan). Mixing was performed with Rushton-type impellers rotating at 400 rpm. Temperature in the cultivation was maintained at +30° C. pH was maintained at 6.8±0.2 by adding 8 M NaOH or 3.6 M $H_3PO_4$ by software control. Cultivation medium contained 1 g/L $NH_4OH$, 0.23 g/L $KH_2PO_4$, 0.29 g/L $Na_2HPO_4 \cdot 2 H_2O$, 0.005 g/L $NaVO_3 \cdot H_2O$, 0.2 g/L $FeSO_4 \cdot 7 H_2O$, 0.5 g/L $MgSO_4 \cdot 7 H_2O$, 0.01 g/L $CaSO_4$, 0.00015 g/L $Na_2MoO_4 \cdot 2 H_2O$, 0.005 g/L $MnSO_4$, 0.0005 g/L $ZnSO_4 \cdot 7 H_2O$, 0.0015 g/L $H_3BO_3$, 0.001 g/L $CoSO_4$, 0.00005 g/L $CuSO_4$ and 0.0001 g/L $NiSO_4$ prepared in tap water. A mixture containing 1.8-10.5 L/min hydrogen gas, 0.6-2.5 L/min oxygen gas and 1.8-5 L/min carbon dioxide gas was supplied constantly as the main source of energy and carbon. Dissolved oxygen level was maintained at 7.2±0.5% by adjusting the gas mixture composition. The inoculum for the cultivation was prepared as described in Example 1. Growth was monitored by taking samples manually and analysing the cell density as optical density by measuring absorbance at 600 nm (Ultrospec 2100 pro UV/visible spectrophotometer, Biochrom Ltd., England) and by measuring cell dry weight (CDW) by drying in oven overnight at 105° C. Optical density was also monitored by using an in situ absorbance probe (Trucell 2, Finesse Ltd, USA). A growth curve of the cultivation is presented in FIG. 1. The maximum growth rate in batch phase was 0.06 $h^{-1}$. The maximum cell density was 4.5 g_CDW/L at 92 h. After 92 h of cultivation, feed of fresh cultivation medium as described above was started at a dilution rate of 0.01 $h^{-1}$. During the continued feed, the cell density was on average 2.9 g_CDW/L. Cultivation liquid was constantly collected to a cooled (+10° C.) tank from which it was fed in 300-liter batches to a continuous centrifugal separator (BTPX-205, Alfa-Laval AB, Sweden). The cell-containing slurry collected from the separator was fed into an atmospheric double drum dryer (Buflovak 6×8 ADDD, Hebeler process solutions Llc., USA), heated with 4 bar steam and drums rotating at 3.5 rpm. This resulted in dried cell powder with approximately 96/dry matter content. Analysis results of the dried cell powder are presented in Table 1 for the proximate composition, in Table 2 for the amino acid composition, in Table 3 for the fatty acid composition, and in Table 4 for the vitamin content. Analyses demonstrate that the dried cell powder has high protein content with all the essential amino acids. It also contains more unsaturated than saturated fatty acids and a lot of B-group vitamins. Peptidoglycan content was only 0.002 mg/g_CDW and lipopolysaccharide content was 0.01 mg/g_CDW. It would be beneficial that these concentrations would be as small as possible. In comparison, in a commercial lactic acid bacteria preparation analysed at the same time, the peptidoglycan content was 0.244 mg/g_DW and the lipopolysaccharide content was 0.015 mg/g_DW. Cytotoxicity and genotoxicity assays were performed using the supernatant samples of cultivation. No cytotoxicity against HepG2 or HeLa229 human cell lines was observed. No genotoxicity against *Escherichia coli* WP2 trp- or CM871 uvrA recA lexA strains was observed.

TABLE 1

Analysis results of dried cell powder of isolated bacterial strain deposited as VTT-E-193585.

| Parameter | Method | Unit | Value |
|---|---|---|---|
| Moisture | Drying at 103° C. | g/100 g | 3.3 |
| Protein | Kjeldahl (N × 6.25) | g/100 g | 72.2 |
| Fat | Weibull-Stoldt | g/100 g | 6.0 |
| Saturated fatty acids | Calculation based on Table 3 | g/100 g | 1.8 |
| Mono-unsaturated fatty acids | Calculation based on Table 3 | g/100 g | 3.8 |
| Polyunsaturated fatty acids | Calculation based on Table 3 | g/100 g | 0.4 |
| Omega 3 fatty acids | Calculation based on Table 3 | g/100 g | <0.01 |
| Omega 6 fatty acids | Calculation based on Table 3 | g/100 g | 0.4 |
| Dietary fibres | Gravimetric | g/100 g | 10.5 |
| Ash | Ashing at 550° C. | g/100 g | 5.8 |
| Glucose | HPLC-ELSD | g/100 g | <0.15 |
| Fructose | HPLC-ELSD | g/100 g | <0.1 |
| Sucrose | HPLC-ELSD | g/100 g | <0.1 |
| Lactose | HPLC-ELSD | g/100 g | <0.25 |
| Maltose | HPLC-ELSD | g/100 g | <0.2 |
| Total sugars | Calculation | g/100 g | <0.8 |
| Carbohydrates | Calculation | g/100 g | 2.2 |
| Energy | Calculation | kJ/100 g | 1572 |
| Energy | Calculation | kcal/100 g | 373 |

US 12,600,940 B2

41

TABLE 2

Amino acid composition of dried cell powder of isolated
bacterial strain deposited as VTT-E-193585.

| Parameter | Method | Unit | Value |
|---|---|---|---|
| Lysine | Ion chromatography | % | 3.95 |
| Methionine | Ion chromatography | % | 1.60 |
| Cystine | Ion chromatography | % | 0.39 |
| Aspartic | Ion chromatography | % | 6.82 |
| Threonine | Ion chromatography | % | 3.47 |
| Serine | Ion chromatography | % | 2.75 |
| Glutamic | Ion chromatography | % | 8.84 |
| Proline | Ion chromatography | % | 3.14 |
| Glycine | Ion chromatography | % | 4.40 |
| Alanine | Ion chromatography | % | 6.94 |
| Valine | Ion chromatography | % | 4.96 |
| Isoleucine | Ion chromatography | % | 3.34 |
| Leucine | Ion chromatography | % | 6.08 |
| Tyrosine | Ion chromatography | % | 2.99 |
| Phenylalanine | Ion chromatography | % | 4.58 |
| Histidine | Ion chromatography | % | 1.66 |
| Arginine | Ion chromatography | % | 4.96 |
| Tryptophan | HPLC | % | 1.34 |

TABLE 3

Fatty acid composition of dried cell powder of isolated
bacterial strain deposited as VTT-E-193585.

| Parameter | Method | Unit | Value |
|---|---|---|---|
| C16:0 (Palmitic acid) | GC-MS | % | 24.8 |
| C16:1 (Palmitoleic acid) | GC-MS | % | 3.0 |
| C18:0 (Stearic acid) | GC-MS | % | 4.4 |
| C18:1n9 (Oleic acid) | GC-MS | % | 59.9 |
| C18:2n6 (Linoleic acid) | GC-MS | % | 6.1 |
| C18:3n3 (alpha-Linolenic acid) | GC-MS | % | 0.4 |

TABLE 4

Vitamin content of dried cell powder of isolated
bacterial strain deposited as VTT-E-193585.

| Parameter | Method | Unit | Value |
|---|---|---|---|
| Vitamin A (RE) | HPLC | IU/100 g | <100 |
| Vitamin E (TE) | HPLC | mg/100 g | 0.33 |
| Vitamin D3 | HPLC | IU/100 g | <10 |
| Vitamin D2 | HPLC | IU/100 g | 21.6 |
| Vitamin C | HPLC | mg/100 g | <1 |
| Thiamine chloride Hydrochloride | LC-MS/MS | mg/100 g | 0.9 |
| Vitamin B1 (Thiamine) | Calculation | mg/100 g | 0.708 |
| Vitamin B2 (Riboflavin) | HPLC | mg/100 g | 6.27 |
| Pyridoxine hydrochloride | HPLC | mg/100 g | 3.39 |
| Vitamin B6 (Pyridoxine) | Calculation | mg/100 g | 2.79 |
| Vitamin B12 | LC-MS/MS | µg/100 g | 224 |
| Choline chloride | LC-MS/MS | mg/100 g | 14.3 |
| Biotin | LC-MS/MS | µg/100 g | 15.6 |
| Folic acid | Microbiological | µg/100 g | 1270 |
| Niacin (Vitamin B3) | Microbiological | mg/100 g | 23.2 |
| Pantothenic acid | Microbiological | mg/100 g | 6.53 |

Example 3. Cultivation of Isolated Bacterial Strain on Different Nitrogen Sources The isolated bacterial strain deposited as VTT-E-193585 was cultivated in a 15-vessel parallel bioreactor system at 200 mL volume (Medicel Explorer, Medicel Oy, Finland). Mixing was performed with Rushton-type impellers rotating at 800 rpm. The temperature in the cultivation was maintained at +30° C. pH was maintained at 6.8 by adding 1 M NaOH. The cultivation medium contained 0.23 g/L

42

Figure 2:
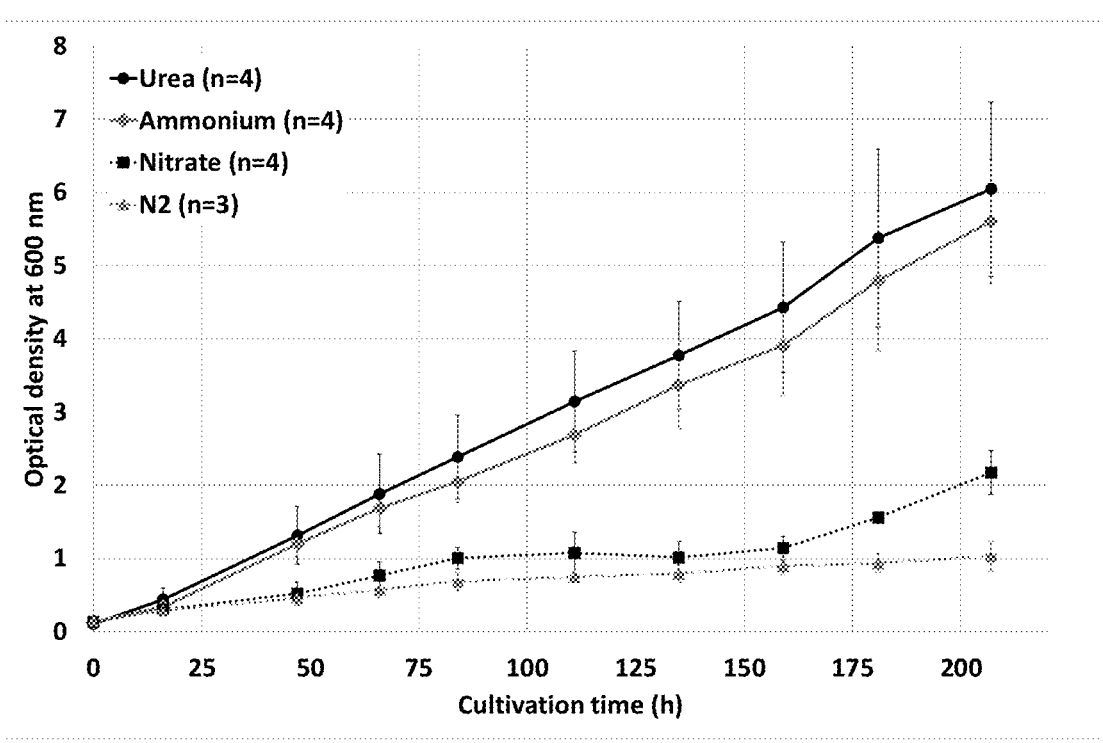
FIG. 2. Optical density measured at 600 nm during parallel chemoautotrophic 200-mL cultivations of isolated bacterial strain deposited as VTT-E-193585 on different nitrogen sources.

$KH_2PO_4$, 0.29 g/L $Na_2HPO_4 \cdot 2 H_2O$, 0.005 g/L $NaVO_3 \cdot H_2O$, 0.2 g/L $FeSO_4 \cdot 7 H_2O$, 0.5 g/L $MgSO_4 \cdot 7 H_2O$, 0.01 g/L $CaSO_4$, 0.00015 g/L $Na_2MoO_4 \cdot 2 H_2O$, 0.005 g/L $MnSO_4$, 0.0005 g/L $ZnSO_4 \cdot 7 H_2O$, 0.0015 g/L $H_3BO_3$, 0.001 g/L $COSO_4$, 0.00005 g/L $CUSO_4$ and 0.0001 g/L $NiSO_4$ prepared in tap water. Furthermore, the nitrogen source was varied in the cultivations so that four cultivations contained 18.7 mM $NH_4OH$, four cultivations contained 9.34 mM urea $(OC(NH_2)_2)$, four cultivations contained 18.7 mM potassium nitrate ($KNO_3$), and three cultivations were left without nitrogen source in the medium. A mixture containing 22 mL/min hydrogen gas, 3.2 mL/min air and 6.4 mL/min carbon dioxide gas was supplied constantly as the main source of energy and carbon. Thus, with air, all cultivations were also supplied with nitrogen gas. Growth was monitored by taking samples automatically and analysing the cell density as optical density by measuring absorbance at 600 nm (Ultrospec 2100 pro UV/visible spectrophotometer, Biochrom Ltd., England). Growth curves of the cultivations are presented in FIG. 2. Growth on ammonia and urea were comparable. Growth on nitrate or nitrogen gas was clearly slower than on ammonia or urea. Towards the end of the cultivation, the growth on nitrate was better than growth on nitrogen gas as the only source of nitrogen. There was nonetheless growth also in the cultivations in which nitrogen gas was the only source of nitrogen demonstrating that isolated bacterial strain deposited as VTT-E-193585 is capable of nitrogen fixation.

Example 4. Characterization of Antibiotic Susceptibility

Antibiotic susceptibility of gentamicin, kanamycin, streptomycin, tetracycline, ampicillin, ciprofloxacin, colistin and fosfomycin for the isolated bacterial strain deposited as VTT-E-193585 was analysed according to CLSI M07-A111 standard (Clinical and laboratory standards institute. Methods for dilution antimicrobial susceptibility tests for bacteria that grow aerobically, 11th ed. CLSI standard M07, 2018) with hand-made microdilution plate for ampicillin, ciprofloxacin and colistin, with VetMIC Lact-1 plate (SVA National Veterinary Institute, Uppsala, Sweden) for gentamicin, kanamycin, streptomycin and tetracycline using broth microdilution method and for fosfomycin using agar dilution method in aerobic conditions at +35±2° C. for 48±1 hours using cation-adjusted Mueller Hinton Broth-medium (LabM, LAB114, cations $Mg^{2+}$ and $Ca^{2+}$ added separately). *Escherichia coli* ATCC 25922 was used as quality control strain and it was incubated in aerobic conditions, at +35±2° C. for 18±2 hours. Results of antibiotic susceptibility of strains are presented in Table 5. The isolation bacterial strain was found to be generally sensitive to antibiotics. For gentamicin, kanamycin, streptomycin and tetracycline minimum inhibitory concentration (MIC) values for VTT-E-193585 were lower or comparable to *E. coli* ATCC 25922, while for ampicillin, ciprofloxacin, colistin and fosfomycin the MIC values were higher in VTT-E-193585.

TABLE 5

Minimum Inhibitory Concentration (MIC, µg/ml) -values of antibiotics
for VTT-E-193585 strain and *Escherichia coli* ATCC 25922

| | VTT-E-193585 48 h ± 1 h | *E. coli* ATCC 25922 18 h ± 2 h |
|---|---|---|
| Gentamicin | 0.5 | 0.5 |
| Kanamycin | 2 | 4 |
| Streptomycin | 0.5 | 4 |

TABLE 5-continued

Minimum Inhibitory Concentration (MIC, μg/ml) -values of antibiotics
for VTT-E-193585 strain and *Escherichia coli* ATCC 25922

|  | VTT-E-193585 48 h ± 1 h | *E. coli* ATCC 25922 18 h ± 2 h |
|---|---|---|
| Tetracycline | 0.25 | 1 |
| Ampicillin | 16 | 8 |
| Ciprofloxacin | 0.06 | 0.008 |

TABLE 5-continued

Minimum Inhibitory Concentration (MIC, μg/ml) -values of antibiotics
for VTT-E-193585 strain and *Escherichia coli* ATCC 25922

|  | VTT-E-193585 48 h ± 1 h | *E. coli* ATCC 25922 18 h ± 2 h |
|---|---|---|
| Colistin | 4 | 2 |
| Fosfomycin | 32 | 0.5 |

The invention claimed is:

1. A process for the production of biomass, said process comprising culturing an isolated bacterial strain VTT-E-193585 or a derivative thereof, wherein said derivative preferably has retained the ability to grow using hydrogen gas as energy source and carbon dioxide as the only carbon source.

2. The process according to claim 1, comprising culturing the bacterial strain in continuous culture with hydrogen as energy source and an inorganic carbon source, wherein the inorganic carbon source comprises carbon dioxide.

3. The process according to claim 2, wherein the bacterial strain comprises:

i) a gene encoding ribulose-1,5-bisphosphate carboxylase/oxygenase (rubisco) large chain having the sequence set forth in SEQ ID NO:3 or a sequence having more than 93% sequence identity to the sequence set forth in SEQ ID NO:3, and/or ii) a gene encoding a ribulose-1,5-bisphosphate carboxylase/oxygenase (rubisco) small chain having the sequence set forth in SEQ ID NO:5 or a sequence having more than 83% sequence identity to the sequence set forth in SEQ ID NO:5, and/or iii) a gene encoding a Nicotinamide Adenine Dinucleotide (NAD$^+$)-reducing hydrogenase HoxS subunit alpha having the sequence set forth in SEQ ID NO:7 or a sequence having more than 70% sequence identity to the sequence set forth in SEQ ID NO: 7, and/or iv) a gene encoding a NAD$^+$-reducing hydrogenase HoxS subunit beta having the sequence set forth in SEQ ID NO:9 or a sequence having more than 77% sequence identity to the sequence set forth in SEQ ID NO:9, and/or v) a gene encoding a NAD$^+$-reducing hydrogenase HoxS subunit gamma having the sequence set forth in SEQ ID NO:11 or a sequence having more than 70% sequence identity to the sequence set forth in SEQ ID NO:11, and/or vi) a gene encoding a NAD$^+$-reducing hydrogenase HoxS subunit delta having the sequence set forth in SEQ ID NO:13 or a sequence having more than 79% sequence identity to the sequence set forth in SEQ ID NO:13, and/or vii) a gene encoding a Nickel-Iron-Selenium (NiFeSe) hydrogenase large subunit having the sequence set forth in SEQ ID NO:15 or a sequence having more than 84% sequence identity to the sequence set forth in SEQ ID NO:15, and/or viii) a gene encoding a NiFeSe hydrogenase small subunit having the sequence set forth in SEQ ID NO:17 or a sequence having more than 90% sequence identity to the sequence set forth in SEQ ID NO:17, and/or ix) a gene encoding an Adenosine Triphosphate (ATP) synthase gamma chain atpG_1 having the sequence set forth in SEQ ID NO:19 or a sequence having more than 70% sequence identity to the sequence set forth in SEQ ID NO:19, and/or x) a gene encoding an ATP synthase subunit alpha atpA_1 having the sequence set forth in SEQ ID NO:21 or a sequence having more than 78% sequence identity to the sequence set forth in SEQ ID NO:21, and/or xi) a gene encoding an ATP synthase subunit b atpF_1 having the sequence set forth in SEQ ID NO:23 or a sequence having more than 62% sequence identity to the sequence set forth in SEQ ID NO:23, and/or xii) a gene encoding an ATP synthase subunit c, sodium ion specific atpE_1 having the sequence set forth in SEQ ID NO:25 or a sequence having more than 90% sequence identity to the sequence set forth in SEQ ID NO:25, and/or xiii) a gene encoding an ATP synthase subunit a atpB_1 having the sequence set forth in SEQ ID NO:27 or a sequence having more than 80% sequence identity to the sequence set forth in SEQ ID NO:27, and/or xiv) a gene encoding an ATP synthase epsilon chain atpC_1 having the sequence set forth in SEQ ID NO:29 or a sequence having more than 71% sequence identity to the sequence set forth in SEQ ID NO:29, and/or xv) a gene encoding an ATP synthase subunit beta atpD_1 having the sequence set forth in SEQ ID NO:31 or a sequence having more than 84% sequence identity to the sequence set forth in SEQ ID NO:31, and/or xvi) a gene encoding an ATP synthase subunit beta atpD_2 having the sequence set forth in SEQ ID NO:33 or a sequence having more than 97% sequence identity to the sequence set forth in SEQ ID NO:33, and/or xvii) a gene encoding an ATP synthase gamma chain atpG_2 having the sequence set forth in SEQ ID NO:35 or a sequence having more than 86% sequence identity to the sequence set forth in SEQ ID NO:35, and/or xviii) a gene encoding an ATP synthase subunit alpha atpA_2 having the sequence set forth in SEQ ID NO:37 or a sequence having more than 98% sequence identity to the sequence set forth in SEQ ID NO:37, and/or xix) a gene encoding an ATP synthase subunit delta atpH having the sequence set forth in SEQ ID NO:39 or a sequence having more than 85% sequence identity to the sequence set forth in SEQ ID NO:39, and/or xx) a gene encoding an ATP synthase subunit b atpF_2 having the sequence set forth in SEQ ID NO:41 or a sequence having more than 87% sequence identity to the sequence set forth in SEQ ID NO:41, and/or xxi) a gene encoding an ATP synthase subunit b'atpG_3 having the sequence set forth in SEQ ID NO:43 or a sequence having more than 81% sequence identity to the sequence set forth in SEQ ID NO:43, and/or xxii) a gene encoding ATP synthase subunit c atpE_2 having the sequence set forth in SEQ ID NO:45 or a sequence having more than 98% sequence identity to the sequence set forth in SEQ ID NO:45, and/or xxiii) a gene encoding an ATP synthase subunit a atpB_2 having the sequence set forth in SEQ ID NO:47 or a sequence having more than 92% sequence identity to the sequence set forth in SEQ ID NO:47, and/or xiv) a gene encoding an ATP synthase protein I atpI having the sequence set forth in SEQ ID NO:49 or a sequence having more than 60% sequence identity to the sequence set forth in SEQ ID NO:49, and/or xv) a gene encoding a nitrogenase molybdenum-iron protein alpha chain nifD_1 having the sequence set forth in SEQ ID NO:51 or a sequence having more than 60% sequence identity to the sequence set forth in SEQ ID NO:51, and/or xvi) a gene encoding nitrogenase molybdenum-iron protein alpha chain nifD_2 having the sequence set forth in SEQ ID NO:53 or a sequence having more than 60% sequence identity to the sequence set forth in SEQ ID NO:53, and/or xvii) a gene encoding a nitrogenase molybdenum-iron protein beta chain nifK_1 having the sequence set forth in SEQ ID NO:55 or a sequence having more than 87% sequence identity to the sequence set forth in SEQ ID NO:55, and/or xviii) a gene encoding a nitrogenase molybdenum-iron protein beta chain nifK_2 having the sequence set forth in SEQ ID NO:57 or a sequence having more than 95% sequence identity to the sequence set forth in SEQ ID NO:57, and/or xxix) a gene encoding a nitrogenase iron protein nifH having the sequence set forth in SEQ ID NO:59 or a sequence having more than 98.5% sequence identity to the sequence set forth in SEQ ID NO:59, wherein the strain preferably comprises:

the genes described in iii), iv), v) and vi), the genes described in vii) and viii), or the genes described in iii), iv), v), vi), vii) and viii).

\* \* \* \* \*

SEQUENCE LISTING

```
<160> NUMBER OF SEQ ID NOS: 59

<210> SEQ ID NO 1
<211> LENGTH: 1482
<212> TYPE: DNA
<213> ORGANISM: Unknown
<220> FEATURE:
<223> OTHER INFORMATION: Novel strain

<400> SEQUENCE: 1
cttgagagtt tgatcctggc tcagagcgaa cgctggcggc aggcctaaca catgcaagtc      60
gagcgcccag caatgggagc ggcagacggg tgagtaacgc gtggggatgt gcccaatggt     120
acggaataac ccagggaaac ttggactaat accgtatgag cccttcgggg gaaagattta     180
tcgccattgg atcaacccgc gtctgattag ctagttggtg gggtaacggc ccaccaaggc     240
gacgatcagt agctggtctg agaggatgat cagccacact gggactgaga cacggcccag     300
actcctacgg gaggcagcag tggggaatat tggacaatgg gcgcaagcct gatccagcca     360
tgccgcgtgt gtgatgaagg ccttagggtt gtaaagcact ttcgccggtg aagataatga     420
cggtaaccgg agaagaagcc ccggctaact tcgtgccagc agccgcggta atacgaaggg     480
ggctagcgtt gctcggaatc actgggcgta aagcgcacgt aggcggatcg ttaagtcagg     540
ggtgaaatcc tggagctcaa ctccagaact gcccttgata ctggcgacct tgagttcgag     600
agaggttggt ggaactgcga gtgtagaggt gaaattcgta gatattcgca agaacaccag     660
tggcgaaggc ggccaactgg ctcgatactg acgctgaggt gcgaaagcgt ggggagcaaa     720
caggattaga taccctggta gtccacgccg taaacgatgg atgctagccg ttgggcagct     780
tgctgttcag tggcgcagct aacgcattaa gcatcccgcc tggggagtac ggtcgcaaga     840
ttaaaactca aaggaattga cgggggcccg cacaagcggt ggagcatgtg gtttaattcg     900
aagcaacgcg cagaacctta ccagcctttg acatggcagg acgatttcca gagatggatc     960
tcttccagca atggacctgc acacaggtgc tgcatggctg tcgtcagctc gtgtcgtgag    1020
atgttgggtt aagtcccgca acgagcgcaa ccctcgcctc tagttgccag cattcagttg    1080
ggcactctag agggactgcc ggtgataagc cgagaggaag gtggggatga cgtcaagtcc    1140
tcatggccct tacgggctgg gctacacacg tgctacaatg gtggtgacag tgggatgcga    1200
aagggcgacc tctagcaaat ctccaaaagc catctcagtt cggattgtac tctgcaactc    1260
gagtgcatga agttggaatc gctagtaatc gtggatcagc atgccacggt gaatacgttc    1320
ccgggccttg tacacaccgc ccgtcacacc atgggagttg gctttacccg aaggcgctgc    1380
gctaacccgc aagggaggca ggcgaccacg gtagggtcag cgactggggt gaagtcgtaa    1440
caaggtagcc gtaggggaac ctgcggctgg atcacctcct tt                       1482

<210> SEQ ID NO 2
<211> LENGTH: 1467
```

<212> TYPE: DNA
<213> ORGANISM: Unknown
<220> FEATURE:
<223> OTHER INFORMATION: novel strain

<400> SEQUENCE: 2

```
atgggtgccg aagcaaccgt cgggcagatc acggacgcca agaagagata cgccgccggc      60
gtgctgaagt acgcccagat gggctactgg aacggcgact acgttcccaa ggacaccgac     120
ctcctggcgt tgttccgcat cacccccag gcgggcgtgg acccggtgga agccgccgcg     180
gcggtcgccg gcgaaagctc caccgctacc tggaccgtgg tgtggaccga ccggctcacc     240
gccgccgacg tctaccgcgc caaggcctac aaggtggagc cggtgccggg ccaggaaggc     300
cagtatttct gctacatcgc ctatgatctc gatttgttcg aggaaggctc catcgccaac     360
ctcacggcgt cgatcatcgg caacgtcttc tccttcaagc cgctgaaggc ggcgcggctg     420
gaggacatgc ggcttcccgt cgcctatgtg aagaccttcc gcggcccgcc caccggcatc     480
gtggtcgagc gcgagcgcct ggacaagttc ggccgccccc ttctgggcgc caccaccaag     540
ccgaagcttg gcctctcggg caagaattac ggccgcgtgg tctatgaggc cctcaagggc     600
ggcctcgact tcgtgaagga cgacgagaac atcaactcgc agcccttcat gcactggcgc     660
gatcgcttcc tctattgcat ggaggccgtc aacaaggccc aggccgagac cggcgaggtg     720
aaggggcact atctcaacat caccgccggg accatggagg agatgtaccg ccgcgccgag     780
ttcgccaagg aactgggctc cgtggtggtg atggtggatc tcatcatcgg ctggaccgcc     840
atccagtcca tgtccaactg cgtgccgcgag aacgacatga tcctgcacat gcaccgtgcg     900
ggccatggca cctacacgcg ccagaagagc cacggcgtct ccttccgcgt catcgccaag     960
tggctgcggc tcgccggcgt cgaccacctg cacaccggca ccgccgtggg caagctggaa    1020
ggcgacccca tgaccgtgca gggcttctac aatgtctgcc gcgagacgac gacgcagcag    1080
gacctcaccc gcggcctgtt cttcgagcag gactgggggcg gcatccgcaa ggtgatgccg    1140
gtggcctccg gcggcatcca tgcgggccag atgcaccagc tcatcgacct gttcggcgag    1200
gacgtggtgc tccagttcgg cggcggcacc atcggccacc cggacggcat ccaggccggc    1260
gccaccgcca accgcgtggc gctggaaacc atgatcctcg cccgcaacga gggccgcgac    1320
atcaggaacg agggcccgga aatcctggtg gaagccgcca atggtgccg tccgctgcgc     1380 gcggcgctcg atacctgggg cgaggtgacc ttcaactacg cctccaccga cacgtccgat    1440
tacgtgccca ccgcgtccgt cgcctga                                        1467
```

<210> SEQ ID NO 3
<211> LENGTH: 488
<212> TYPE: PRT
<213> ORGANISM: Unknown
<220> FEATURE:
<223> OTHER INFORMATION: novel strain

<400> SEQUENCE: 3

```
Met Gly Ala Glu Ala Thr Val Gly Gln Ile Thr Asp Ala Lys Lys Arg
1               5                   10                  15

Tyr Ala Ala Gly Val Leu Lys Tyr Ala Gln Met Gly Tyr Trp Asn Gly
                20                  25                  30

Asp Tyr Val Pro Lys Asp Thr Asp Leu Leu Ala Val Phe Arg Ile Thr
            35                  40                  45

Pro Gln Ala Gly Val Asp Pro Val Glu Ala Ala Ala Val Ala Gly
        50                  55                  60
```

```
Glu Ser Ser Thr Ala Thr Trp Thr Val Val Trp Thr Asp Arg Leu Thr
65              70              75              80

Ala Ala Asp Val Tyr Arg Ala Lys Ala Tyr Lys Val Glu Pro Val Pro
                85              90              95

Gly Gln Glu Gly Gln Tyr Phe Cys Tyr Ile Ala Tyr Asp Leu Asp Leu
            100             105             110

Phe Glu Glu Gly Ser Ile Ala Asn Leu Thr Ala Ser Ile Ile Gly Asn
        115             120             125

Val Phe Ser Phe Lys Pro Leu Lys Ala Ala Arg Leu Glu Asp Met Arg
    130             135             140

Leu Pro Val Ala Tyr Val Lys Thr Phe Arg Gly Pro Pro Thr Gly Ile
145             150             155             160

Val Val Glu Arg Glu Arg Leu Asp Lys Phe Gly Arg Pro Leu Leu Gly
            165             170             175

Ala Thr Thr Lys Pro Lys Leu Gly Leu Ser Gly Lys Asn Tyr Gly Arg
            180             185             190

Val Val Tyr Glu Ala Leu Lys Gly Gly Leu Asp Phe Val Lys Asp Asp
            195             200             205

Glu Asn Ile Asn Ser Gln Pro Phe Met His Trp Arg Asp Arg Phe Leu
    210             215             220

Tyr Cys Met Glu Ala Val Asn Lys Ala Gln Ala Glu Thr Gly Glu Val
225             230             235             240

Lys Gly His Tyr Leu Asn Ile Thr Ala Gly Thr Met Glu Glu Met Tyr
            245             250             255

Arg Arg Ala Glu Phe Ala Lys Glu Leu Gly Ser Val Val Val Met Val
            260             265             270

Asp Leu Ile Ile Gly Trp Thr Ala Ile Gln Ser Met Ser Asn Trp Cys
        275             280             285

Arg Glu Asn Asp Met Ile Leu His Met His Arg Ala Gly His Gly Thr
    290             295             300

Tyr Thr Arg Gln Lys Ser His Gly Val Ser Phe Arg Val Ile Ala Lys
305             310             315             320

Trp Leu Arg Leu Ala Gly Val Asp His Leu His Thr Gly Thr Ala Val
            325             330             335

Gly Lys Leu Glu Gly Asp Pro Met Thr Val Gln Gly Phe Tyr Asn Val
            340             345             350

Cys Arg Glu Thr Thr Thr Gln Gln Asp Leu Thr Arg Gly Leu Phe Phe
            355             360             365

Glu Gln Asp Trp Gly Gly Ile Arg Lys Val Met Pro Val Ala Ser Gly
    370             375             380

Gly Ile His Ala Gly Gln Met His Gln Leu Ile Asp Leu Phe Gly Glu
385             390             395             400

Asp Val Val Leu Gln Phe Gly Gly Gly Thr Ile Gly His Pro Asp Gly
            405             410             415

Ile Gln Ala Gly Ala Thr Ala Asn Arg Val Ala Leu Glu Thr Met Ile
            420             425             430

Leu Ala Arg Asn Glu Gly Arg Asp Ile Arg Asn Glu Gly Pro Glu Ile
            435             440             445

Leu Val Glu Ala Ala Lys Trp Cys Arg Pro Leu Arg Ala Ala Leu Asp
    450             455             460

Thr Trp Gly Glu Val Thr Phe Asn Tyr Ala Ser Thr Asp Thr Ser Asp
465             470             475             480

Tyr Val Pro Thr Ala Ser Val Ala
```

-continued

485

<210> SEQ ID NO 4
<211> LENGTH: 405
<212> TYPE: DNA
<213> ORGANISM: Unknown
<220> FEATURE:
<223> OTHER INFORMATION: novel strain

<400> SEQUENCE: 4
atgcgcatca cccaaggctc cttctccttc ctgccggacc tcaccgacac gcagatcaag       60
gcccaggtgc aatattgcct ggaccagggc tgggcggtct cggtggagca caccgacgat      120
ccccacccgc gcaacaccta ttgggagatg tggggcccgc ccatgttcga tctgcgcgac      180
gcggccggcg tcttcggcga gatcgaagcc tgccgggccg ccaatcccga gcattatgtg      240
cgggtgaacg ccttcgattc cagccgcgga tgggagacga tccgcctgtc cttcatcgtt      300
cagcggccca ccgtggaaga gggcttccgc ctcgaccgca ccgaaggcaa gggccgcaac      360
cagagctacg ccatgcgcta ccgggcgcag ttcgcgccgc gctga                      405

<210> SEQ ID NO 5
<211> LENGTH: 134
<212> TYPE: PRT
<213> ORGANISM: Unknown
<220> FEATURE:
<223> OTHER INFORMATION: novel strain

<400> SEQUENCE: 5

Met Arg Ile Thr Gln Gly Ser Phe Ser Phe Leu Pro Asp Leu Thr Asp
1               5                   10                  15

Thr Gln Ile Lys Ala Gln Val Gln Tyr Cys Leu Asp Gln Gly Trp Ala
            20                  25                  30

Val Ser Val Glu His Thr Asp Asp Pro His Pro Arg Asn Thr Tyr Trp
        35                  40                  45

Glu Met Trp Gly Pro Pro Met Phe Asp Leu Arg Asp Ala Ala Gly Val
    50                  55                  60

Phe Gly Glu Ile Glu Ala Cys Arg Ala Ala Asn Pro Glu His Tyr Val
65                  70                  75                  80

Arg Val Asn Ala Phe Asp Ser Ser Arg Gly Trp Glu Thr Ile Arg Leu
                85                  90                  95

Ser Phe Ile Val Gln Arg Pro Thr Val Glu Glu Gly Phe Arg Leu Asp
            100                 105                 110

Arg Thr Glu Gly Lys Gly Arg Asn Gln Ser Tyr Ala Met Arg Tyr Arg
        115                 120                 125

Ala Gln Phe Ala Pro Arg
    130

<210> SEQ ID NO 6
<211> LENGTH: 1896
<212> TYPE: DNA
<213> ORGANISM: Unknown
<220> FEATURE:
<223> OTHER INFORMATION: novel strain

<400> SEQUENCE: 6
atgatgccat ctgagccgca cggcgcgggc atgccgcccc cacgggaagc ggccgcggtt       60
cccacccccc aggaggtgag cgcggtggtg gccgaggtgg tcgcggatgc cgtggcatcg      120
gtgggcggcg cacgcacccg gctcatggac atcgtccagc tggcccagca gcgtctcggc      180

-continued

```
catctctccg aagagaccat ggcggccatt gccgcgcggc tcgccattcc gccggtggaa      240
gtggcggaca tggtgtcctt ctacgccttc ctgaaccgcg cgcccaaggg ccgctaccac      300
atccgcctgt cgcgcagccc catctcgctg atgaagggcg ccgaggcggt ggctgccgcc      360
ttctgccaga tcctcggcat cgccatgggc gagacctcgc aggatggcga cttcaccctg      420
gaatggacca acgacatcgg catggccgac caggagccgg ccgccctcgt caacggcacg      480
gtgatgacgc agctcgcgcc cggcgatgcg gccatcatcg tcggccggct gcgggcccat      540
cacgcgccca atgccctgcc gctgttccct ggagccggcg tggccggctc cggcctgccc      600
catgcccgga tccgcccag cctggtgatg ccgggacagc ttctgttccg cgaggaccac      660
acgacgccgg gcgccggcat caaggcggca ctcgccctca ccccggacga agtggtgcag      720
aaggtctccg ccgcgcgcct gcgcgggcgg ggtggcgccg gctttcccac cggtctcaaa      780
tggaagctct gccgccagtc gcccgccacc acccgccatg tgatctgcaa tgcggacgag      840
ggcgagcccg gcaccttcaa ggatcgcgtg ctgctcacgc aggcgccgca cctcatgttc      900
gacggcatga ccatcgccgg ctacgccttg ggggcgcggg agggcgtggt ctatctgcgc      960
ggcgagtacg cctatctgtg ggagcctctg catgcggtcc tgcgcgagcg ctatgggctc     1020
gggctcgccg gcgcgaacat cctgggacac gcgggcttcg acttcgacat ccgcatccag     1080
ctgggcgccg gcgcctatat ctgcggcgag gaatccgcgc tggtggaatc gctggaaggc     1140
aagcgcggct cgcccgcga ccgcccccccc ttcccaccg tgcgcggcca tctccagcag     1200
cccaccgccg tggacaatgt ggagaccttc gcctgcgccg cccgcatcct ggaggatggc     1260
gtggaggcgt cgcgcgggcat cggcacgccc gaatccgccg gcacgaagct cctctcggtg     1320
tcgggcgatt gcccgcgccc cggcgtgtat gaggtgccct tcggcctcac ggtgaacgcg     1380
ctgctcgacc ttgtcggcgc gccggacgcc gccttcgtgc agatgggtgg gccgtccggc     1440
caatgcgtgg cgccgaagga ttacggccgc cgcatcgcct tcgaggacct gcccaccggc     1500
ggctcggtga tggtgttcgg cccgggggcgc gacgtgctcg ccatggtgcg cgagttcgcg     1560
gatttcttcg ccggcgaatc ctgcggctgg tgcacgccct gccgggtggg caccaccttg     1620
ctcaaggaag agctggacaa gctcctcgcc aaccgcgcca ccctcgccga catccgcgcg     1680
ctggagaccc tggccacgac cgtctcccgc accagccgct gcggcctcgg ccagacggcg     1740
cccaacccca tcctttccac catgcgcaac ctgccggaag cctatgaggc gaggctgagg     1800
cccgaagact tcctgccctg ggcctcgctc gacgaggcgc tgaagcccgc catcgtcatc     1860
cagggccgcg cgcccgtgcc ggaggaagag gcatga                                1896
```

<210> SEQ ID NO 7
<211> LENGTH: 631
<212> TYPE: PRT
<213> ORGANISM: Unknown
<220> FEATURE:
<223> OTHER INFORMATION: novel strain

<400> SEQUENCE: 7

```
Met Met Pro Ser Glu Pro His Gly Ala Gly Met Pro Pro Pro Arg Glu
1               5                   10                  15

Ala Ala Ala Val Pro Thr Pro Gln Glu Val Ser Ala Val Val Ala Glu
            20                  25                  30

Val Val Ala Asp Ala Val Ala Ser Val Gly Gly Ala Arg Thr Arg Leu
        35                  40                  45

Met Asp Ile Val Gln Leu Ala Gln Gln Arg Leu Gly His Leu Ser Glu
    50                  55                  60
```

-continued

```
Glu Thr Met Ala Ala Ile Ala Ala Arg Leu Ala Ile Pro Pro Val Glu
65              70                  75                  80

Val Ala Asp Met Val Ser Phe Tyr Ala Phe Leu Asn Arg Ala Pro Lys
                85                  90                  95

Gly Arg Tyr His Ile Arg Leu Ser Arg Ser Pro Ile Ser Leu Met Lys
            100                 105                 110

Gly Ala Glu Ala Val Ala Ala Phe Cys Gln Ile Leu Gly Ile Ala
            115                 120                 125

Met Gly Glu Thr Ser Gln Asp Gly Asp Phe Thr Leu Glu Trp Thr Asn
    130                 135                 140

Asp Ile Gly Met Ala Asp Gln Glu Pro Ala Ala Leu Val Asn Gly Thr
145                 150                 155                 160

Val Met Thr Gln Leu Ala Pro Gly Asp Ala Ala Ile Ile Val Gly Arg
                165                 170                 175

Leu Arg Ala His His Ala Pro Asn Ala Leu Pro Leu Phe Pro Gly Ala
            180                 185                 190

Gly Val Ala Gly Ser Gly Leu Pro His Ala Arg Ile Arg Pro Ser Leu
            195                 200                 205

Val Met Pro Gly Gln Leu Leu Phe Arg Glu Asp His Thr Thr Pro Gly
    210                 215                 220

Ala Gly Ile Lys Ala Ala Leu Ala Leu Thr Pro Asp Glu Val Val Gln
225                 230                 235                 240

Lys Val Ser Ala Ala Arg Leu Arg Gly Arg Gly Gly Ala Gly Phe Pro
                245                 250                 255

Thr Gly Leu Lys Trp Lys Leu Cys Arg Gln Ser Pro Ala Thr Thr Arg
            260                 265                 270

His Val Ile Cys Asn Ala Asp Glu Gly Glu Pro Gly Thr Phe Lys Asp
            275                 280                 285

Arg Val Leu Leu Thr Gln Ala Pro His Leu Met Phe Asp Gly Met Thr
    290                 295                 300

Ile Ala Gly Tyr Ala Leu Gly Ala Arg Glu Gly Val Val Tyr Leu Arg
305                 310                 315                 320

Gly Glu Tyr Ala Tyr Leu Trp Glu Pro Leu His Ala Val Leu Arg Glu
                325                 330                 335

Arg Tyr Gly Leu Gly Leu Ala Gly Ala Asn Ile Leu Gly His Ala Gly
            340                 345                 350

Phe Asp Phe Asp Ile Arg Ile Gln Leu Gly Ala Gly Ala Tyr Ile Cys
            355                 360                 365

Gly Glu Glu Ser Ala Leu Val Glu Ser Leu Glu Gly Lys Arg Gly Ser
    370                 375                 380

Pro Arg Asp Arg Pro Pro Phe Pro Thr Val Arg Gly His Leu Gln Gln
385                 390                 395                 400

Pro Thr Ala Val Asp Asn Val Glu Thr Phe Ala Cys Ala Ala Arg Ile
                405                 410                 415

Leu Glu Asp Gly Val Glu Ala Phe Ala Gly Ile Gly Thr Pro Glu Ser
            420                 425                 430

Ala Gly Thr Lys Leu Leu Ser Val Ser Gly Asp Cys Pro Arg Pro Gly
            435                 440                 445

Val Tyr Glu Val Pro Phe Gly Leu Thr Val Asn Ala Leu Leu Asp Leu
    450                 455                 460

Val Gly Ala Pro Asp Ala Ala Phe Val Gln Met Gly Gly Pro Ser Gly
465                 470                 475                 480
```

-continued

```
Gln Cys Val Ala Pro Lys Asp Tyr Gly Arg Arg Ile Ala Phe Glu Asp
                485                 490                 495

Leu Pro Thr Gly Gly Ser Val Met Val Phe Gly Pro Gly Arg Asp Val
            500                 505                 510

Leu Ala Met Val Arg Glu Phe Ala Asp Phe Phe Ala Gly Glu Ser Cys
            515                 520                 525

Gly Trp Cys Thr Pro Cys Arg Val Gly Thr Thr Leu Leu Lys Glu Glu
        530                 535                 540

Leu Asp Lys Leu Leu Ala Asn Arg Ala Thr Leu Ala Asp Ile Arg Ala
545                 550                 555                 560

Leu Glu Thr Leu Ala Thr Thr Val Ser Arg Thr Ser Arg Cys Gly Leu
            565                 570                 575

Gly Gln Thr Ala Pro Asn Pro Ile Leu Ser Thr Met Arg Asn Leu Pro
            580                 585                 590

Glu Ala Tyr Glu Ala Arg Leu Arg Pro Glu Asp Phe Leu Pro Trp Ala
            595                 600                 605

Ser Leu Asp Glu Ala Leu Lys Pro Ala Ile Val Ile Gln Gly Arg Ala
    610                 615                 620

Pro Val Pro Glu Glu Glu Ala
625                 630

<210> SEQ ID NO 8
<211> LENGTH: 1491
<212> TYPE: DNA
<213> ORGANISM: Unknown
<220> FEATURE:
<223> OTHER INFORMATION: novel strain

<400> SEQUENCE: 8
atgagccggg gatcccccga tgccgggaaa gaccgcacca tgagcgccac cgacggcacc      60 accgccccc gcaagatcgt catcgatccg gtgacccgcg tggagggcca cggcaaggtc     120 accatccgc tggatgaagc cggcgcggtg gaggatgcgc gtttccacat cgtggagttc     180
cgcggcttcg agcggttcat ccagggccgg atgtactggg aagtgcccct tatcatccag     240
cggctgtgcg gcatctgccc ggtgagccac catctggcgg cggcgaaagc catggaccag     300
gtggcgggcg tggaccgcgt accgcccacc gccgagaaac tgcgccggct gatgcattat     360
gggcaggtgc tgcaatccaa cgctttgcac atcttccacc tcgcctcgcc cgacctcctg     420
ttcggcttcg acgcgccggc cgagcagcgc aacatcatcg ccgtgctcca gcgttatccg     480
gagatcggca aatgggcgat cttcatcagg aagttcggcc aggaggtcat caaggccacc     540
ggcgggcgca agatccatcc caccagcgcc attcccggcg gggtcaacca gaacctcgcc     600
gtggaggacc gcgacgccct gcgcgccaag gtgggcgaga tcatcagctg gtgcatggcg     660
gcgctggacc atcacaaggc ctatgtggcg gaaaaccggg cgctgcatga cagcttcgcc     720 gccttccccct ccgccttcat gagcctcgtg gggccggatg gcggcatgga cctttatgac     780
ggcaccctgc gggtgatcga tgccgagggc gccccccctca tcgaaggcgc gccgcccgcc     840
tcctaccgcg accacctcat cgaggaggtg cggccctgga gctatctgaa attcccccat     900
ctgcgcgcct cggccgcga cgatggctgg tatcgggtcg cccccctcgc ccaggtcaat     960
tgcgccgcgt ccatcgacac gccccgcgcc gaggcggccc ggcgggactt catggccgag    1020
ggcggcggca agccggtgca tgccaccctc gcttatcact gggcgcggct catcgtgctg    1080
gtccattgcg cggagaagat cgaacagctg ctgttcgacg acgacctgca aggctgcgat    1140
ctgcgtgcgg agggcacccg cgcgcggggaa ggcgtcgcct ggatcgaggc gccgcgcggc    1200
```

-continued

```
accctcatcc accattacga ggtggacgag aacgaccagg tgcgccgcgc caacctcatc    1260
gtctccacca cccacaataa cgaggccatg aaccgcgccg tgcggcaggt ggcgaagacg    1320
gacctttccg gtcgcgagat caccgaaggg ctgctgaacc atatcgaggt ggccatccgc    1380
gccttcgacc cctgcctgtc ctgcgccacc catgcgctgg gccagatgcc gctgatcgtg    1440
acgcttgaag atgcctccgg cgcagagatc gcccgcggag tgaaggaatg a            1491
```

```
<210> SEQ ID NO 9
<211> LENGTH: 496
<212> TYPE: PRT
<213> ORGANISM: Unknown
<220> FEATURE:
<223> OTHER INFORMATION: novel strain

<400> SEQUENCE: 9

Met Ser Arg Gly Ser Pro Asp Ala Gly Lys Asp Arg Thr Met Ser Ala
1               5                   10                  15

Thr Asp Gly Thr Thr Ala Pro Arg Lys Ile Val Ile Asp Pro Val Thr
            20                  25                  30

Arg Val Glu Gly His Gly Lys Val Thr Ile Arg Leu Asp Glu Ala Gly
        35                  40                  45

Ala Val Glu Asp Ala Arg Phe His Ile Val Glu Phe Arg Gly Phe Glu
    50                  55                  60

Arg Phe Ile Gln Gly Arg Met Tyr Trp Glu Val Pro Leu Ile Ile Gln
65                  70                  75                  80

Arg Leu Cys Gly Ile Cys Pro Val Ser His His Leu Ala Ala Ala Lys
                85                  90                  95

Ala Met Asp Gln Val Ala Gly Val Asp Arg Val Pro Pro Thr Ala Glu
            100                 105                 110

Lys Leu Arg Arg Leu Met His Tyr Gly Gln Val Leu Gln Ser Asn Ala
        115                 120                 125

Leu His Ile Phe His Leu Ala Ser Pro Asp Leu Leu Phe Gly Phe Asp
    130                 135                 140

Ala Pro Ala Glu Gln Arg Asn Ile Ile Ala Val Leu Gln Arg Tyr Pro
145                 150                 155                 160

Glu Ile Gly Lys Trp Ala Ile Phe Ile Arg Lys Phe Gly Gln Glu Val
                165                 170                 175

Ile Lys Ala Thr Gly Gly Arg Lys Ile His Pro Thr Ser Ala Ile Pro
            180                 185                 190

Gly Gly Val Asn Gln Asn Leu Ala Val Glu Asp Arg Asp Ala Leu Arg
        195                 200                 205

Ala Lys Val Gly Glu Ile Ile Ser Trp Cys Met Ala Ala Leu Asp His
    210                 215                 220

His Lys Ala Tyr Val Ala Glu Asn Arg Ala Leu His Asp Ser Phe Ala
225                 230                 235                 240

Ala Phe Pro Ser Ala Phe Met Ser Leu Val Gly Pro Asp Gly Gly Met
                245                 250                 255

Asp Leu Tyr Asp Gly Thr Leu Arg Val Ile Asp Ala Glu Gly Ala Pro
            260                 265                 270

Leu Ile Glu Gly Ala Pro Pro Ala Ser Tyr Arg Asp His Leu Ile Glu
        275                 280                 285

Glu Val Arg Pro Trp Ser Tyr Leu Lys Phe Pro His Leu Arg Ala Phe
    290                 295                 300

Gly Arg Asp Asp Gly Trp Tyr Arg Val Gly Pro Leu Ala Gln Val Asn
```

-continued

```
305                310                315                320

Cys Ala Ala Ser Ile Asp Thr Pro Arg Ala Glu Ala Ala Arg Arg Asp
                325                330                335

Phe Met Ala Glu Gly Gly Gly Lys Pro Val His Ala Thr Leu Ala Tyr
            340                345                350

His Trp Ala Arg Leu Ile Val Leu Val His Cys Ala Glu Lys Ile Glu
            355                360                365

Gln Leu Leu Phe Asp Asp Asp Leu Gln Gly Cys Asp Leu Arg Ala Glu
        370                375                380

Gly Thr Arg Arg Gly Glu Gly Val Ala Trp Ile Glu Ala Pro Arg Gly
385                390                395                400

Thr Leu Ile His His Tyr Glu Val Asp Glu Asn Asp Gln Val Arg Arg
                405                410                415

Ala Asn Leu Ile Val Ser Thr Thr His Asn Asn Glu Ala Met Asn Arg
            420                425                430

Ala Val Arg Gln Val Ala Lys Thr Asp Leu Ser Gly Arg Glu Ile Thr
            435                440                445

Glu Gly Leu Leu Asn His Ile Glu Val Ala Ile Arg Ala Phe Asp Pro
        450                455                460

Cys Leu Ser Cys Ala Thr His Ala Leu Gly Gln Met Pro Leu Ile Val
465                470                475                480

Thr Leu Glu Asp Ala Ser Gly Ala Glu Ile Ala Arg Gly Val Lys Glu
                485                490                495
```

```
<210> SEQ ID NO 10
<211> LENGTH: 720
<212> TYPE: DNA
<213> ORGANISM: Unknown
<220> FEATURE:
<223> OTHER INFORMATION: novel strain

<400> SEQUENCE: 10
atgagcgaga cccccttcac ctttaccgtg gacggcatcg cggtcccggc caccccggc       60 cagagcgtca tcgaggcgtg cgatgcggcg ggcatctata tcccgcgcct gtgccaccac      120
ccggacctgc cgccggcggg ccattgccgg gtgtgcacct gcatcatcga cgggcggccg      180
gccagcgcct gcaccatgcc cgccgccagg ggcatggtgg tggagaacga gacgcccgct      240
ttgctggcgg agcggcgcac gctgatcgag atgctgttcg cggaaggcaa ccatttctgc      300
cagttctgcg aggcgagcgg cgattgcgaa ttgcaggcgc tgggctacct gttcggcatg      360
gtggccccgc ccttcccca tctgtggccg aagcggccgg tggatgccag ccatccggat       420
atctatatcg accacaatcg ctgcatcctg tgctcgcgct gcgtgcgcgc ctcgcgcacc      480
ctggacggca agtccgtgtt cggcttcgag gggcgcggca tcgagatgca tctggcggtg      540
accggcgggc acctggacga cagcgccatc gccgccgccg acagggcggt tgagatgtgc      600
ccggtgggct gcatcgtcct caagcgcacc ggctaccgca cgccctatgg ccggcggcgc      660
tacgacgccg cgcccatcgg ctccgacatc accgcccggc gcggcggcgc gaaggactga      720
```

```
<210> SEQ ID NO 11
<211> LENGTH: 239
<212> TYPE: PRT
<213> ORGANISM: Unknown
<220> FEATURE:
<223> OTHER INFORMATION: novel strain

<400> SEQUENCE: 11
```

-continued

```
Met Ser Glu Thr Pro Phe Thr Phe Thr Val Asp Gly Ile Ala Val Pro
1               5                   10                  15

Ala Thr Pro Gly Gln Ser Val Ile Glu Ala Cys Asp Ala Ala Gly Ile
            20                  25                  30

Tyr Ile Pro Arg Leu Cys His His Pro Asp Leu Pro Pro Ala Gly His
        35                  40                  45

Cys Arg Val Cys Thr Cys Ile Ile Asp Gly Arg Pro Ala Ser Ala Cys
    50                  55                  60

Thr Met Pro Ala Ala Arg Gly Met Val Val Glu Asn Glu Thr Pro Ala
65                  70                  75                  80

Leu Leu Ala Glu Arg Arg Thr Leu Ile Glu Met Leu Phe Ala Glu Gly
                85                  90                  95

Asn His Phe Cys Gln Phe Cys Glu Ala Ser Gly Asp Cys Glu Leu Gln
            100                 105                 110

Ala Leu Gly Tyr Leu Phe Gly Met Val Ala Pro Pro Phe Pro His Leu
        115                 120                 125

Trp Pro Lys Arg Pro Val Asp Ala Ser His Pro Asp Ile Tyr Ile Asp
    130                 135                 140

His Asn Arg Cys Ile Leu Cys Ser Arg Cys Val Arg Ala Ser Arg Thr
145                 150                 155                 160

Leu Asp Gly Lys Ser Val Phe Gly Phe Glu Gly Arg Gly Ile Glu Met
                165                 170                 175

His Leu Ala Val Thr Gly Gly His Leu Asp Asp Ser Ala Ile Ala Ala
            180                 185                 190

Ala Asp Arg Ala Val Glu Met Cys Pro Val Gly Cys Ile Val Leu Lys
        195                 200                 205

Arg Thr Gly Tyr Arg Thr Pro Tyr Gly Arg Arg Tyr Asp Ala Ala
    210                 215                 220

Pro Ile Gly Ser Asp Ile Thr Ala Arg Arg Gly Gly Ala Lys Asp
225                 230                 235
```

```
<210> SEQ ID NO 12
<211> LENGTH: 543
<212> TYPE: DNA
<213> ORGANISM: Unknown
<220> FEATURE:
<223> OTHER INFORMATION: novel strain

<400> SEQUENCE: 12
atggccaagc ccaaactcgc cacctgcgcg ctggccggct gcttcggctg ccacatgtcc      60
ttcctggaca tggacgagcg catcgtcgag ctcatcgacc tggtggacct cgacgtctcg     120
cccctcgacg acaagaaaaa cttcaccggc atggtggaaa tcggcctggt ggaaggcggc     180
tgcgccgacg agcgccatgt gaaggtgctg cgcgagttcc gcgagaaatc cgcatcctg     240 gtggcggtgg gcgcctgcgc catcaccggc ggcatcccgg cattgcgcaa cctcgccggc     300
ctcgacgaat gcctgaggga agcctacctc accggcccca cggtggaagg cggcgggctc     360
attcccaacg acccggagct gccgctgctg ctggacaagg tctatccggt gcaggacttc     420
gtgaagatcg accatttcct gcccggctgc ccgccctcgg ccgacgccat ctgggcggct     480
ctgaaggcgc tgctgaccgg caccgagccg catctgccct accgcttt caagtacgaa     540 tga                                                                   543
```

```
<210> SEQ ID NO 13
<211> LENGTH: 180
<212> TYPE: PRT
```

<213> ORGANISM: Unknown
<220> FEATURE:
<223> OTHER INFORMATION: novel strain

<400> SEQUENCE: 13

Met Ala Lys Pro Lys Leu Ala Thr Cys Ala Leu Ala Gly Cys Phe Gly
1               5                   10                  15

Cys His Met Ser Phe Leu Asp Met Asp Glu Arg Ile Val Glu Leu Ile
                20                  25                  30

Asp Leu Val Asp Leu Asp Val Ser Pro Leu Asp Asp Lys Lys Asn Phe
            35                  40                  45

Thr Gly Met Val Glu Ile Gly Leu Val Glu Gly Gly Cys Ala Asp Glu
        50                  55                  60

Arg His Val Lys Val Leu Arg Glu Phe Arg Glu Lys Ser Arg Ile Leu
65                  70                  75                  80

Val Ala Val Gly Ala Cys Ala Ile Thr Gly Gly Ile Pro Ala Leu Arg
                85                  90                  95

Asn Leu Ala Gly Leu Asp Glu Cys Leu Arg Glu Ala Tyr Leu Thr Gly
            100                 105                 110

Pro Thr Val Glu Gly Gly Gly Leu Ile Pro Asn Asp Pro Glu Leu Pro
        115                 120                 125

Leu Leu Leu Asp Lys Val Tyr Pro Val Gln Asp Phe Val Lys Ile Asp
    130                 135                 140

His Phe Leu Pro Gly Cys Pro Pro Ser Ala Asp Ala Ile Trp Ala Ala
145                 150                 155                 160

Leu Lys Ala Leu Leu Thr Gly Thr Glu Pro His Leu Pro Tyr Pro Leu
                165                 170                 175

Phe Lys Tyr Glu
            180

<210> SEQ ID NO 14
<211> LENGTH: 1013
<212> TYPE: DNA
<213> ORGANISM: Unknown
<220> FEATURE:
<223> OTHER INFORMATION: novel strain

<400> SEQUENCE: 14
tccagacccg ggcaacattg ctccatgtgc tgggcaccct ggccggccgc tggccccata        60
ccctcgcgct ccagcccggc ggggtgaccc gaagcgccga ccagcacgac cgcatgcgcc       120
tgctcgcgac gctgaaggcg gtgcgggcgg cgctggaaga gaccttgttc ggcgcgcctt       180
tggaagaggt ggcggccctg gacggcgccg ccgccgtgga ggcctggcgc gccaacggcc       240
cggaagggga tttccgcctg ttcctggaga tcgccgccga cctggagctg gaccggctcg       300
gccgcgcgca cgaccgcttt ctctccttcg gcgcctacgc ccaggacgag gggcgccttt       360
atggcgccgg caccttcgag gccgggacgg cgggagggct cgatcccaac gccatcaccg       420
aggaccacgc cttcgcccgc atggaggacc gcgcggcgcc ccatgcgccc tttgacggct       480
ccaccttccc cgatgccgac gacaccgagg gctacacctg gtgcaaggcg ccgcgccttg       540
ccggcctgcc cttcgagacc ggcgccttcg cccggcaggt ggtggcgggc catccgctcg       600
cccgggacct cgtgacgcgg gaaggcggca ctgtgcgcag ccgcgtggtc ggccggctgc       660
tggaaaccgc gcgcaccctg atcgccatgg agggctgggt gaaggaactg cggcccgaag       720
ggccctggtg cgcccagggc cacctgcccc aggaaggccg cgccttcggc ctcaccgagg       780
cggcgcgcgg ggcgctcggc cactggatgg tggtggagaa gggccgcatt gcccgctacc       840

-continued

```
agatcatcgc ccccaccacc tggaacttct ccccccgcga cggcgcgggc ctgcccggcc      900
cgctggagac ggccctggtg ggcgcgcccg tgcggcaggg agagacgacg cccgtgagcg      960
tgcagcacat cgtgcgctcc ttcgacccgt gcatggtctg cactgtgcat tga           1013
```

```
<210> SEQ ID NO 15
<211> LENGTH: 485
<212> TYPE: PRT
<213> ORGANISM: Unknown
<220> FEATURE:
<223> OTHER INFORMATION: novel strain

<400> SEQUENCE: 15

Met Ser Ala Glu Thr Arg Arg Leu Val Val Gly Pro Phe Asn Arg Val
1               5                   10                  15

Glu Gly Asp Leu Glu Val Arg Leu Asp Val Gln Asp Gly Arg Val Gln
                20                  25                  30

Gln Ala Phe Val Ser Ser Pro Leu Phe Arg Gly Phe Glu Arg Ile Leu
            35                  40                  45

Glu Gly Arg Asp Pro Arg Asp Ala Leu Val Ile Ala Pro Arg Ile Cys
        50                  55                  60

Gly Ile Cys Ser Val Ser Gln Ser His Ala Ala Ala Leu Ala Leu Ala
65                  70                  75                  80

Gly Leu Gln Gly Ile Ala Pro Thr His Asp Gly Arg Ile Ala Thr Asn
                85                  90                  95

Leu Ile Val Ala Ala Glu Asn Val Ala Asp His Leu Thr His Phe His
                100                 105                 110

Val Phe Phe Met Pro Asp Phe Ala Arg Ala Val Tyr Glu Asp Arg Pro
            115                 120                 125

Trp Phe Ala Gln Ala Ala Arg Arg Phe Lys Ala Asn Gln Gly Val Ser
        130                 135                 140

Val Arg Arg Ala Leu Gln Thr Arg Ala Thr Leu Leu His Val Leu Gly
145                 150                 155                 160

Thr Leu Ala Gly Arg Trp Pro His Thr Leu Ala Leu Gln Pro Gly Gly
                165                 170                 175

Val Thr Arg Ser Ala Asp Gln His Asp Arg Met Arg Leu Leu Ala Thr
                180                 185                 190

Leu Lys Ala Val Arg Ala Ala Leu Glu Glu Thr Leu Phe Gly Ala Pro
            195                 200                 205

Leu Glu Glu Val Ala Ala Leu Asp Gly Ala Ala Ala Val Glu Ala Trp
        210                 215                 220

Arg Ala Asn Gly Pro Glu Gly Asp Phe Arg Leu Phe Leu Glu Ile Ala
225                 230                 235                 240

Ala Asp Leu Glu Leu Asp Arg Leu Gly Arg Ala His Asp Arg Phe Leu
                245                 250                 255

Ser Phe Gly Ala Tyr Ala Gln Asp Glu Gly Arg Leu Tyr Gly Ala Gly
            260                 265                 270

Thr Phe Glu Ala Gly Thr Ala Gly Gly Leu Asp Pro Asn Ala Ile Thr
            275                 280                 285

Glu Asp His Ala Phe Ala Arg Met Glu Asp Arg Ala Ala Pro His Ala
        290                 295                 300

Pro Phe Asp Gly Ser Thr Phe Pro Asp Ala Asp Asp Thr Glu Gly Tyr
305                 310                 315                 320

Thr Trp Cys Lys Ala Pro Arg Leu Ala Gly Leu Pro Phe Glu Thr Gly
                325                 330                 335
```

```
Ala Phe Ala Arg Gln Val Val Ala Gly His Pro Leu Ala Arg Asp Leu
            340                 345                 350

Val Thr Arg Glu Gly Gly Thr Val Arg Ser Arg Val Val Gly Arg Leu
            355                 360                 365

Leu Glu Thr Ala Arg Thr Leu Ile Ala Met Glu Gly Trp Val Lys Glu
    370                 375                 380

Leu Arg Pro Glu Gly Pro Trp Cys Ala Gln Gly His Leu Pro Gln Glu
385                 390                 395                 400

Gly Arg Ala Phe Gly Leu Thr Glu Ala Ala Arg Gly Ala Leu Gly His
                405                 410                 415

Trp Met Val Val Glu Lys Gly Arg Ile Ala Arg Tyr Gln Ile Ile Ala
            420                 425                 430

Pro Thr Thr Trp Asn Phe Ser Pro Arg Asp Gly Ala Gly Leu Pro Gly
            435                 440                 445

Pro Leu Glu Thr Ala Leu Val Gly Ala Pro Val Arg Gln Gly Glu Thr
    450                 455                 460

Thr Pro Val Ser Val Gln His Ile Val Arg Ser Phe Asp Pro Cys Met
465                 470                 475                 480

Val Cys Thr Val His
                485
```

```
<210> SEQ ID NO 16
<211> LENGTH: 858
<212> TYPE: DNA
<213> ORGANISM: Unknown
<220> FEATURE:
<223> OTHER INFORMATION: novel strain

<400> SEQUENCE: 16 acggggagg aagcccgcgc catcttcgac gccatccttg ccggcgttat cgtcctcgac        60
gccctgtgcg tggaaggcgc gctgctgcgc gggccgaacg gcaccgggcg cttccatgtg       120
ctggcgggca cggacacccc caccatcgac tgggcgcggc agctcgccgg catggcgcgc       180
cacgtggtgg cggtgggcac ctgcgccgcc tatggggggcg tgacggcggc gggcatcaac      240
cccaccgatg cctgcggcct ccagttcgac ggacgccgga agggtggggc gctggggcg        300 gacttccgct cccgctcggg gcttccggtc atcaatgtgg ccggctgccc cacccatccc       360
aactgggtga cggaaaccct gatgctgctc gcctgcggcc tgctgggcga ggccgacctc       420
gacgtctatg ccgcccgcg cttctatgcg gacctgctgg tgcatcacgg ctgcccgcgc        480
aacgaatact atgaatacaa ggcgagcgcc gagaagatga gcgacctcgg ctgcatgatg       540
gagcatctgg gctgcctcgg cacccaggcc cacgccgact gcaacacgcg cctttggaat       600
ggcgagggct cgtgcacccg cggcggctat gcctgcatca actgcacggc gccggaattc       660
gaggagccgg gccacgcctt cctggagacg cccaagatcg gcggcatccc catcggcctg       720
cccaccgaca tgcccaaggc ctggttcatc gccttgtcct ccctcgccaa ggcggcgacg       780
ccggagcggc tgcgcaagaa cgcggtgtcc gaccatgtgg tcacgccgcc cgccgtcaag       840
gacatcaagc ggcgatga                                                     858
```

```
<210> SEQ ID NO 17
<211> LENGTH: 335
<212> TYPE: PRT
<213> ORGANISM: Unknown
<220> FEATURE:
<223> OTHER INFORMATION: novel strain
```

```
<400> SEQUENCE: 17

Met Ser Thr Pro Phe Ser Val Leu Trp Leu Gln Ser Gly Gly Cys Gly
1               5                   10                  15

Gly Cys Thr Met Ser Leu Leu Cys Ala Glu Ala Pro Asp Leu Ala Thr
                20                  25                  30

Thr Leu Asp Ala Ala Gly Ile Gly Phe Leu Trp His Pro Ala Leu Ser
            35                  40                  45

Glu Glu Thr Gly Glu Glu Ala Arg Ala Ile Phe Asp Ala Ile Leu Ala
        50                  55                  60

Gly Val Ile Val Leu Asp Ala Leu Cys Val Glu Gly Ala Leu Leu Arg
65                  70                  75                  80

Gly Pro Asn Gly Thr Gly Arg Phe His Val Leu Ala Gly Thr Asp Thr
                85                  90                  95

Pro Thr Ile Asp Trp Ala Arg Gln Leu Ala Gly Met Ala Arg His Val
                100                 105                 110

Val Ala Val Gly Thr Cys Ala Ala Tyr Gly Gly Val Thr Ala Ala Gly
            115                 120                 125

Ile Asn Pro Thr Asp Ala Cys Gly Leu Gln Phe Asp Gly Arg Arg Lys
            130                 135                 140

Gly Gly Ala Leu Gly Ala Asp Phe Arg Ser Arg Ser Gly Leu Pro Val
145                 150                 155                 160

Ile Asn Val Ala Gly Cys Pro Thr His Pro Asn Trp Val Thr Glu Thr
                165                 170                 175

Leu Met Leu Leu Ala Cys Gly Leu Leu Gly Glu Ala Asp Leu Asp Val
                180                 185                 190

Tyr Gly Arg Pro Arg Phe Tyr Ala Asp Leu Leu Val His His Gly Cys
            195                 200                 205

Pro Arg Asn Glu Tyr Tyr Glu Tyr Lys Ala Ser Ala Glu Lys Met Ser
            210                 215                 220

Asp Leu Gly Cys Met Met Glu His Leu Gly Cys Leu Gly Thr Gln Ala
225                 230                 235                 240

His Ala Asp Cys Asn Thr Arg Leu Trp Asn Gly Glu Gly Ser Cys Thr
                245                 250                 255

Arg Gly Gly Tyr Ala Cys Ile Asn Cys Thr Ala Pro Glu Phe Glu Glu
                260                 265                 270

Pro Gly His Ala Phe Leu Glu Thr Pro Lys Ile Gly Gly Ile Pro Ile
            275                 280                 285

Gly Leu Pro Thr Asp Met Pro Lys Ala Trp Phe Ile Ala Leu Ser Ser
        290                 295                 300

Leu Ala Lys Ala Ala Thr Pro Glu Arg Leu Arg Lys Asn Ala Val Ser
305                 310                 315                 320

Asp His Val Val Thr Pro Pro Ala Val Lys Asp Ile Lys Arg Arg
                325                 330                 335

<210> SEQ ID NO 18
<211> LENGTH: 870
<212> TYPE: DNA
<213> ORGANISM: Unknown
<220> FEATURE:
<223> OTHER INFORMATION: novel strain

<400> SEQUENCE: 18
gtgaccgagc gcctgtccga cgtcaacgcc cgcatcgcct cggtgcggca gctctcatcg      60
gtcatcacgg ccatgcgggg cattgcggcg gcgcgggcgc gggaggcgcg gggtcggctc     120
```

-continued

```
gacggcatcc gcgcctatgc gcagaccatc gccgaggcca tcggccatgt gctcgccgtg          180
ctgcccgagg aggcccgcgc ccggtcctcc gggcaccggc atcggggcca tgcggtcatc          240
gccctgtgcg cggagcaggg ctttgccggc gtcttcaacg agcgggtgct ggacgaggcc          300
gcccggctgc tgaccggcgg ggcggggccg gccgagctgc tgctggtggg cgaccggggc          360
ctgatggtgg cccgcgagcg ggggctcgat gtctcctggt cggtgcccat ggtggcccat          420
gcgggccagg cctcggcgct ggcggaccgc atcagcgagg agctctaccg gcggatcgat          480
gcgggacggg tgacgcgggt gtcggtggtg cacgccgagc ccgccgcgtc cgccgccatc          540
gagacggtgg tgaaagtgct ggtgccgttc gacttcgccc gcttccccct ggcgcgggtg          600
gcatccgccc cgctcatgac catgccgccg ccgcggctgc tggcccagct gtcggaggaa          660
tatgtgttcg ccgagctgtg cgaggcgctc accttgtcct tcgcggcgga gaacgaggcc          720
cgcatgcggg ccatgatcgc cgcccgcgcc aatgtggccg ataccctgga gggcctcgtc          780
ggccgcgccc ggcagatgcg ccaggaggag atcaccaacg agatcatcga gctggaaggc          840
ggcgccggca gcgcccggca tgcggattga                                          870
```

```
<210> SEQ ID NO 19
<211> LENGTH: 289
<212> TYPE: PRT
<213> ORGANISM: Unknown
<220> FEATURE:
<223> OTHER INFORMATION: novel strain

<400> SEQUENCE: 19

Met Thr Glu Arg Leu Ser Asp Val Asn Ala Arg Ile Ala Ser Val Arg
1               5                   10                  15

Gln Leu Ser Ser Val Ile Thr Ala Met Arg Gly Ile Ala Ala Ala Arg
            20                  25                  30

Ala Arg Glu Ala Arg Gly Arg Leu Asp Gly Ile Arg Ala Tyr Ala Gln
        35                  40                  45

Thr Ile Ala Glu Ala Ile Gly His Val Leu Ala Val Leu Pro Glu Glu
    50                  55                  60

Ala Arg Ala Arg Ser Ser Gly His Arg His Arg Gly His Ala Val Ile
65                  70                  75                  80

Ala Leu Cys Ala Glu Gln Gly Phe Ala Gly Val Phe Asn Glu Arg Val
                85                  90                  95

Leu Asp Glu Ala Ala Arg Leu Leu Thr Gly Gly Ala Gly Pro Ala Glu
            100                 105                 110

Leu Leu Leu Val Gly Asp Arg Gly Leu Met Val Ala Arg Glu Arg Gly
        115                 120                 125

Leu Asp Val Ser Trp Ser Val Pro Met Val Ala His Ala Gly Gln Ala
    130                 135                 140

Ser Ala Leu Ala Asp Arg Ile Ser Glu Glu Leu Tyr Arg Arg Ile Asp
145                 150                 155                 160

Ala Gly Arg Val Thr Arg Val Ser Val Val His Ala Glu Pro Ala Ala
                165                 170                 175

Ser Ala Ala Ile Glu Thr Val Val Lys Val Leu Val Pro Phe Asp Phe
            180                 185                 190

Ala Arg Phe Pro Leu Ala Arg Val Ala Ser Ala Pro Leu Met Thr Met
        195                 200                 205

Pro Pro Pro Arg Leu Leu Ala Gln Leu Ser Glu Glu Tyr Val Phe Ala
    210                 215                 220

Glu Leu Cys Glu Ala Leu Thr Leu Ser Phe Ala Ala Glu Asn Glu Ala
```

```
225                 230                 235                 240

Arg Met Arg Ala Met Ile Ala Ala Arg Ala Asn Val Ala Asp Thr Leu
            245                 250                 255

Glu Gly Leu Val Gly Arg Ala Arg Gln Met Arg Gln Glu Glu Ile Thr
            260                 265                 270

Asn Glu Ile Ile Glu Leu Glu Gly Gly Ala Gly Ser Ala Arg His Ala
            275                 280                 285

Asp

<210> SEQ ID NO 20
<211> LENGTH: 1536
<212> TYPE: DNA
<213> ORGANISM: Unknown
<220> FEATURE:
<223> OTHER INFORMATION: novel strain

<400> SEQUENCE: 20
atgagcacgg gcgcgcaagc gagcgaggat tggctcaccc ggagccgggc ggccctggcc       60
gggacgcgcc tttcccagca atcccaatcg gtgggccggg tggaggagat ggccgacggc      120
atcgcccgcg tctccggcct gccggatgtg cggctcgacg agcttctcac cttcgagggc      180
ggccagaccg gctatgccct caccctcgat cgcaccgaga tcgccgtggt gctgctggat      240
gacgcctccg gcgtggaggc gggcgcccgg gtgttcggca ccggcgaggt ggtgaaggtg      300
ccggtggggc cggggctgct gggccgcatc gtcgaccccc tcggccggcc catggaccgc      360
tccgagccgg tggtggcgca ggcgcaccat cccatcgagc ggccggcgcc ggccatcatc      420
gcccgcgacc tggtctcgca gccggttcag accggcacgc tggtggtgga tgcgctgttc      480
tccctcggcc ggggccagcg cgagctcatc atcggcgacc gggctaccgg caagaccgcc      540
atcgcggtgg acaccatcat cagccagaag cattcggaca tcgtgtgcat ctacgtggcg      600
gtgggccagc gcgccgccgc cgtggagcgg gtggtggagg cggtgcgcgc ccacggggcg      660
atcgagcgct gcatcttcgt ggtcgcctcg gccgccgcct cgccagggct gcaatggatc      720
gcgccgttcg ccggcatgac catggcggaa tatttccgcg acaacggcca gcatgcgctc      780
atcatcatcg atgatctcac caagcatgcg gccacccatc gcgagctggc gctgctcacc      840
cacgagccgc cgggccgcga ggcctatccc ggcgacatct ctatgtgca cgcccgcctt      900 ctggagcggg ccgccaagct ctccgccgag ctgggcggtg gctcgctcac ggccctgccc      960
atcgcggaga cggacgcggg aaacctctcc gcctatatcc ccaccaacct catctccatc     1020
accgatgggc agatcgtgct ggattcgcgg ctgttcgcgg ccaaccagcg cccggcggtg     1080
gatgtgggcc tctccgtgag ccgggtgggc ggcaaggcgc agcatcccgc gcttcgggcc     1140
gtgtccgggc gcatccggct cgattattcc cagttcctgg agctggaaat gttcacccgc     1200
ttcggcggca tcaccgatac ccgcgtgaag gcgcagatca cccggggcga gcgcatccgc     1260
gcgctgctca cccagccgcg cttttccacc ctgcgcctcc aggacgaggt ggcgctgctg     1320
gccgcgctgg cggaggggt gttcgacact ttggccccgg ggctgatggg cgccgtgcgt     1380 gccgcattc cggcccagct ggatgcgcag gtgaaggacg tggcctcggc cctcgccgag     1440
ggcaaggtgc tggaggaggg cttgcacgcc cgtctcgtgg cggccgtgcg ggccgtcgcg     1500
gcggacgtgg ccgcgaccgc gaaggccggg ccgtga                               1536

<210> SEQ ID NO 21
<211> LENGTH: 511
<212> TYPE: PRT
```

<213> ORGANISM: Unknown
<220> FEATURE:
<223> OTHER INFORMATION: novel strain

<400> SEQUENCE: 21

Met Ser Thr Gly Ala Gln Ala Ser Glu Asp Trp Leu Thr Arg Ser Arg
1               5                   10                  15

Ala Ala Leu Ala Gly Thr Arg Leu Ser Gln Gln Ser Gln Ser Val Gly
            20                  25                  30

Arg Val Glu Glu Met Ala Asp Gly Ile Ala Arg Val Ser Gly Leu Pro
        35                  40                  45

Asp Val Arg Leu Asp Glu Leu Leu Thr Phe Glu Gly Gly Gln Thr Gly
    50                  55                  60

Tyr Ala Leu Thr Leu Asp Arg Thr Glu Ile Ala Val Val Leu Leu Asp
65                  70                  75                  80

Asp Ala Ser Gly Val Glu Ala Gly Ala Arg Val Phe Gly Thr Gly Glu
                85                  90                  95

Val Val Lys Val Pro Val Gly Pro Gly Leu Leu Gly Arg Ile Val Asp
            100                 105                 110

Pro Leu Gly Arg Pro Met Asp Arg Ser Glu Pro Val Val Ala Gln Ala
        115                 120                 125

His His Pro Ile Glu Arg Pro Ala Pro Ala Ile Ile Ala Arg Asp Leu
    130                 135                 140

Val Ser Gln Pro Val Gln Thr Gly Thr Leu Val Val Asp Ala Leu Phe
145                 150                 155                 160

Ser Leu Gly Arg Gly Gln Arg Glu Leu Ile Ile Gly Asp Arg Ala Thr
                165                 170                 175

Gly Lys Thr Ala Ile Ala Val Asp Thr Ile Ile Ser Gln Lys His Ser
            180                 185                 190

Asp Ile Val Cys Ile Tyr Val Ala Val Gly Gln Arg Ala Ala Ala Val
        195                 200                 205

Glu Arg Val Val Glu Ala Val Arg Ala His Gly Ala Ile Glu Arg Cys
    210                 215                 220

Ile Phe Val Val Ala Ser Ala Ala Ala Ser Pro Gly Leu Gln Trp Ile
225                 230                 235                 240

Ala Pro Phe Ala Gly Met Thr Met Ala Glu Tyr Phe Arg Asp Asn Gly
                245                 250                 255

Gln His Ala Leu Ile Ile Ile Asp Asp Leu Thr Lys His Ala Ala Thr
            260                 265                 270

His Arg Glu Leu Ala Leu Leu Thr His Glu Pro Pro Gly Arg Glu Ala
        275                 280                 285

Tyr Pro Gly Asp Ile Phe Tyr Val His Ala Arg Leu Leu Glu Arg Ala
    290                 295                 300

Ala Lys Leu Ser Ala Glu Leu Gly Gly Gly Ser Leu Thr Ala Leu Pro
305                 310                 315                 320

Ile Ala Glu Thr Asp Ala Gly Asn Leu Ser Ala Tyr Ile Pro Thr Asn
                325                 330                 335

Leu Ile Ser Ile Thr Asp Gly Gln Ile Val Leu Asp Ser Arg Leu Phe
            340                 345                 350

Ala Ala Asn Gln Arg Pro Ala Val Asp Val Gly Leu Ser Val Ser Arg
        355                 360                 365

Val Gly Gly Lys Ala Gln His Pro Ala Leu Arg Ala Val Ser Gly Arg
    370                 375                 380

Ile Arg Leu Asp Tyr Ser Gln Phe Leu Glu Leu Glu Met Phe Thr Arg

-continued

```
385              390              395              400

Phe Gly Gly Ile Thr Asp Thr Arg Val Lys Ala Gln Ile Thr Arg Gly
             405              410              415

Glu Arg Ile Arg Ala Leu Leu Thr Gln Pro Arg Phe Ser Thr Leu Arg
             420              425              430

Leu Gln Asp Glu Val Ala Leu Leu Ala Ala Leu Ala Glu Gly Val Phe
             435              440              445

Asp Thr Leu Ala Pro Gly Leu Met Gly Ala Val Arg Ala Arg Ile Pro
         450              455              460

Ala Gln Leu Asp Ala Gln Val Lys Asp Val Ala Ser Ala Leu Ala Glu
465              470              475              480

Gly Lys Val Leu Glu Glu Gly Leu His Ala Arg Leu Val Ala Ala Val
             485              490              495

Arg Ala Val Ala Ala Asp Val Ala Ala Thr Ala Lys Ala Gly Pro
             500              505              510
```

```
<210> SEQ ID NO 22
<211> LENGTH: 741
<212> TYPE: DNA
<213> ORGANISM: Unknown
<220> FEATURE:
<223> OTHER INFORMATION: novel strain

<400> SEQUENCE: 22
atgcagatcg actggtggac gctgggcctg cagacggtca acgtcctcgt tctcatctgg      60
ctcctgagcc gcttcctgtt caagccggtg gcgcaggtca tcgcgcagcg ccgtgccgag     120
atcgagaagc tggtggagga tgcgcgcgcc gccaaggccg ccgccgaggc cgagcgggac     180
acggcgaagg cggaggaggc gcgccttgcc gccgagcgcg cgccccgcat ggcggcggtc     240
gccaaggagg cggaggcgca gaaggcggca ttgctggccg ccgccaagac cgaggccgag     300
gccctgcacg cggccgcgga agcggccatc gtccgggcgc gggcgagcga ggaggaagcc     360
gccgccgacc gcgccagccg ccttgccgtg gacatcgccg ccaagctgct ggaccggctg     420
cccgacgacg cccgggtcgc gggcttcatc gatggcctcg ccgaggggct tgaagccctg     480
cccgaggcga gccgggcggt gatcggcgtc gacggcgcgc cagtgcgcgt gacggccgcg     540
cgcgccctta tgccggcgga ggaggaggcc tgccgcacgc ggctctccca ggcgctgggc     600
cgtccggtga cgctggccgt gaccatcgac cccgccctca tcgccggcct ggagatggag     660
acgccccacg cggtggtgcg caattccttc aaggccgatc tcgaccgcgt caccgcggcg     720
ctcacccatc atgggacctg a                                                741
```

```
<210> SEQ ID NO 23
<211> LENGTH: 246
<212> TYPE: PRT
<213> ORGANISM: Unknown
<220> FEATURE:
<223> OTHER INFORMATION: novel strain

<400> SEQUENCE: 23

Met Gln Ile Asp Trp Trp Thr Leu Gly Leu Gln Thr Val Asn Val Leu
1               5                10               15

Val Leu Ile Trp Leu Leu Ser Arg Phe Leu Phe Lys Pro Val Ala Gln
             20               25               30

Val Ile Ala Gln Arg Arg Ala Glu Ile Glu Lys Leu Val Glu Asp Ala
         35               40               45

Arg Ala Ala Lys Ala Ala Ala Glu Ala Glu Arg Asp Thr Ala Lys Ala
```

-continued

```
        50              55              60

Glu Glu Ala Arg Leu Ala Ala Glu Arg Gly Ala Arg Met Ala Ala Val
65              70              75              80

Ala Lys Glu Ala Glu Ala Gln Lys Ala Ala Leu Leu Ala Ala Ala Lys
                85              90              95

Thr Glu Ala Glu Ala Leu His Ala Ala Ala Glu Ala Ala Ile Val Arg
                100             105             110

Ala Arg Ala Ser Glu Glu Glu Ala Ala Ala Asp Arg Ala Ser Arg Leu
            115             120             125

Ala Val Asp Ile Ala Ala Lys Leu Leu Asp Arg Leu Pro Asp Asp Ala
        130             135             140

Arg Val Ala Gly Phe Ile Asp Gly Leu Ala Glu Gly Leu Glu Ala Leu
145             150             155             160

Pro Glu Ala Ser Arg Ala Val Ile Gly Val Asp Gly Ala Pro Val Arg
                165             170             175

Val Thr Ala Ala Arg Ala Leu Met Pro Ala Glu Glu Glu Ala Cys Arg
                180             185             190

Thr Arg Leu Ser Gln Ala Leu Gly Arg Pro Val Thr Leu Ala Val Thr
                195             200             205

Ile Asp Pro Ala Leu Ile Ala Gly Leu Glu Met Glu Thr Pro His Ala
        210             215             220

Val Val Arg Asn Ser Phe Lys Ala Asp Leu Asp Arg Val Thr Ala Ala
225             230             235             240

Leu Thr His His Gly Thr
                245
```

```
<210> SEQ ID NO 24
<211> LENGTH: 243
<212> TYPE: DNA
<213> ORGANISM: Unknown
<220> FEATURE:
<223> OTHER INFORMATION: novel strain

<400> SEQUENCE: 24
atgactgtcg agatggtcag catcttcgcg gcggcgctcg ccgtctcctt cggcgccatc      60
gggccggccc tgggcgaggg ccgggcggtg ccgcggccca tggacgccat cgcccgccag     120
ccggaggcgg ccggaacctt gtcgcgcacg ctcttcgtcg gcctcgccat gatcgagacc     180
atggcgatct actgcctggt gatcgcgtc ctggtgctct cgccaatcc gttcgtgaag     240 tga                                                                  243
```

```
<210> SEQ ID NO 25
<211> LENGTH: 80
<212> TYPE: PRT
<213> ORGANISM: Unknown
<220> FEATURE:
<223> OTHER INFORMATION: novel strain

<400> SEQUENCE: 25

Met Thr Val Glu Met Val Ser Ile Phe Ala Ala Ala Leu Ala Val Ser
1               5               10              15

Phe Gly Ala Ile Gly Pro Ala Leu Gly Glu Gly Arg Ala Val Ala Ala
                20              25              30

Ala Met Asp Ala Ile Ala Arg Gln Pro Glu Ala Ala Gly Thr Leu Ser
        35              40              45

Arg Thr Leu Phe Val Gly Leu Ala Met Ile Glu Thr Met Ala Ile Tyr
    50              55              60
```

```
Cys Leu Val Ile Ala Leu Leu Val Leu Phe Ala Asn Pro Phe Val Lys
65                  70                  75                  80

<210> SEQ ID NO 26
<211> LENGTH: 699
<212> TYPE: DNA
<213> ORGANISM: Unknown
<220> FEATURE:
<223> OTHER INFORMATION: novel strain

<400> SEQUENCE: 26
atgggctcgc cgctgatcct cgaacccctg ttccatatcg ggcccgtgcc catcaccgcg        60
ccggtggtgg tcacctggct catcatggcc gccttcattg ggctggcgcg gctcatcacc       120
cggaagcttt ccaccgatcc cacccggacc caggcggcgg tggaaacggt gctgaccgcc       180
atcgattccc agatcgccga caccatgcag gccgatcccg cgccttatcg cgcgctcatc       240
ggcaccatct tcctttatgt gctggtggcc aactggtcct cgctcatccc gggcatcgag       300
ccgcccacgg cgcatatcga gaccgatgcg gcgctcgctt tcatcgtgtt cgccgccacc       360
atcgggttcg ggttgaagac aaggggtgtg aagggctatc tcgccacctt cgccgaaccc       420
tcctgggtga tgatcccgct caatgtggtg gagcagatca cccggacctt ctcgctcatc       480
gtgcgcctgt tcggcaacat catgagcggg gtgttcgtgg tcggcatcat cctgtccctc       540
gccgggctgc tggtgcccat cccccctcatg gcgctcgatc tcctgaccgg cgccgtgcag       600
gcctacatct tcgcggtgct ggcctgcgtg ttcatcggcg cggccattgg cgaggcgccg       660
gcaaagcccc aatcgaagga gccagggaaa acatcatga                               699

<210> SEQ ID NO 27
<211> LENGTH: 232
<212> TYPE: PRT
<213> ORGANISM: Unknown
<220> FEATURE:
<223> OTHER INFORMATION: novel strain

<400> SEQUENCE: 27

Met Gly Ser Pro Leu Ile Leu Glu Pro Leu Phe His Ile Gly Pro Val
1               5                   10                  15

Pro Ile Thr Ala Pro Val Val Val Thr Trp Leu Ile Met Ala Ala Phe
                20                  25                  30

Ile Gly Leu Ala Arg Leu Ile Thr Arg Lys Leu Ser Thr Asp Pro Thr
            35                  40                  45

Arg Thr Gln Ala Ala Val Glu Thr Val Leu Thr Ala Ile Asp Ser Gln
        50                  55                  60

Ile Ala Asp Thr Met Gln Ala Asp Pro Ala Pro Tyr Arg Ala Leu Ile
65                  70                  75                  80

Gly Thr Ile Phe Leu Tyr Val Leu Val Ala Asn Trp Ser Ser Leu Ile
                85                  90                  95

Pro Gly Ile Glu Pro Pro Thr Ala His Ile Glu Thr Asp Ala Ala Leu
            100                 105                 110

Ala Phe Ile Val Phe Ala Ala Thr Ile Gly Phe Gly Leu Lys Thr Arg
        115                 120                 125

Gly Val Lys Gly Tyr Leu Ala Thr Phe Ala Glu Pro Ser Trp Val Met
    130                 135                 140

Ile Pro Leu Asn Val Val Glu Gln Ile Thr Arg Thr Phe Ser Leu Ile
145                 150                 155                 160

Val Arg Leu Phe Gly Asn Ile Met Ser Gly Val Phe Val Val Gly Ile
```

-continued

```
                165                 170                 175
Ile Leu Ser Leu Ala Gly Leu Leu Val Pro Ile Pro Leu Met Ala Leu
            180                 185                 190

Asp Leu Leu Thr Gly Ala Val Gln Ala Tyr Ile Phe Ala Val Leu Ala
        195                 200                 205

Cys Val Phe Ile Gly Ala Ala Ile Gly Glu Ala Pro Ala Lys Pro Gln
    210                 215                 220

Ser Lys Glu Pro Gly Lys Thr Ser
225                 230
```

<210> SEQ ID NO 28
<211> LENGTH: 456
<212> TYPE: DNA
<213> ORGANISM: Unknown
<220> FEATURE:
<223> OTHER INFORMATION: novel strain

<400> SEQUENCE: 28

```
gtgagcgcgc cgctgcacct caccatcacc acgccggccg ccgttctggt ggaccgtgcc        60
gacatcgtgg ccctgcgtgc cgaggacgag agcggcagct tcggcatcct gcccggccat       120
gcggatttcc tgaccgttct ggaggcctgc gtggtgcgct tcaaggatgg ggccgacggc       180
gtgcattatt gtgctctcag tggtggcgtg ctgtcggtcg aggagggccg gcgcatcgcc       240
atcgcctgcc gtcagggcac ggtgagcgac gacctggtcg ccctggaagg ggcggtggac       300
gccatgcgtt cggcggagag cgatgccgac aagcgggccc gggtggagca gatgcgcctt       360
catgcccacg ccgtgcgcca gctcctgcac tatctgcggc ccggccgggc cggcggcgtg       420
gcgccggccg ccgcgccgga ggaggggccg tcatga                                 456
```

<210> SEQ ID NO 29
<211> LENGTH: 151
<212> TYPE: PRT
<213> ORGANISM: Unknown
<220> FEATURE:
<223> OTHER INFORMATION: novel strain

<400> SEQUENCE: 29

```
Met Ser Ala Pro Leu His Leu Thr Ile Thr Thr Pro Ala Ala Val Leu
1               5                   10                  15

Val Asp Arg Ala Asp Ile Val Ala Leu Arg Ala Glu Asp Glu Ser Gly
            20                  25                  30

Ser Phe Gly Ile Leu Pro Gly His Ala Asp Phe Leu Thr Val Leu Glu
        35                  40                  45

Ala Cys Val Val Arg Phe Lys Asp Gly Ala Asp Gly Val His Tyr Cys
    50                  55                  60

Ala Leu Ser Gly Gly Val Leu Ser Val Glu Glu Gly Arg Arg Ile Ala
65                  70                  75                  80

Ile Ala Cys Arg Gln Gly Thr Val Ser Asp Asp Leu Val Ala Leu Glu
            85                  90                  95

Gly Ala Val Asp Ala Met Arg Ser Ala Glu Ser Asp Ala Asp Lys Arg
            100                 105                 110

Ala Arg Val Glu Gln Met Arg Leu His Ala His Ala Val Arg Gln Leu
        115                 120                 125

Leu His Tyr Leu Arg Pro Gly Arg Ala Gly Gly Val Ala Pro Ala Ala
    130                 135                 140

Ala Pro Glu Glu Gly Pro Ser
145                 150
```

-continued

```
<210> SEQ ID NO 30
<211> LENGTH: 1494
<212> TYPE: DNA
<213> ORGANISM: Unknown
<220> FEATURE:
<223> OTHER INFORMATION: novel strain

<400> SEQUENCE: 30
atggcagcgg cagatgagga ggcgcaatcg gccgccggcc ccgcctcggg ccgggtggtg       60
gccgtgcgcg gcgcggtgat cgacatcgcc tttgcccagc ctccgctgcc gccgctggac      120
gacgcccttc tcatcaccga cggccggggc ggcacggtgc tggtggaggt gcagagccat      180
atggatcggc acacggtgcg cgccatcgcc cttcaggcca ccaccggcct cagccggggg      240
ctggaggcgg cgcgggtggg cgggccggtg aaggtgccgg tgggagacca tgtgctcggc      300
cgcctcctgg atgtcaccgg cgccatcggc gacaagggcg ggccgctgcc ggccgacgtg      360
cccacgcggc cgatccacca cgcgccgcca tccttcgccg cgcagggcgg cacgtccgat      420
ctgtttcgca ccggcatcaa ggtcatcgac ctcctggcgc ccctcgccca gggcggcaag      480
gcggccatgt tcggcggggc cggcgtgggc aagaccgtgc tggtgatgga gctgatccac      540
gccatggtgg cgagctacaa gggcatctcg gtgtttgccg gcgtggggga cgctcccgc       600 gagggccacg agatgctgct ggacatgacc gattccggcg tgctcgaccg caccgttctg      660
gtctatggcc agatgaacga gccccccggg gcccgctggc gggtgcccat gacggcgctg      720
accatcgccg aatatttccg cgacgagaag caccagaacg tcctgctgct gatggacaac      780
atcttccgct tcgtccaggc ggggcggag gtctccggcc tttgggccg tccgccctcc        840 cgggtgggat accagccgac gctggcgagc gaggtggcgg cgctccagga acgcatcacc      900
tccgtgggcg aggcctcggt gaccgccatc gaggcggtct acgtgccggc ggatgacttc      960
accgatcccg ccgtgaccac catcgccgcc cacgtggatt ccatggtggt gctctcccgc     1020
gccatggcgg cggagggcat gtatccggcg gtggacccca tctcctcctc gtcggtgctg     1080
ctcgacccgc tcatcgtggg ggacgagcat gcgcgcgtcg ccaacgaggt gcgccggacc     1140
atcgagcatt atcgcgagct tcaggatgtg atctcgctgc tgggcatgga ggaattgggc     1200
accgaggatc gccgcatcgt ggagcgggcg cgccggctcc agcgcttcct cacccagccc     1260
ttcacggtca ccgaggcctt caccggcgtg cccggccgct cggtggccat cgccgacacc     1320
atcgccggct gcaggatgat cctgtccggc gcctgcgacg actggcagga aagcgccctc     1380
tacatggtgg gcaccatcga cgaggcccgc cagaaggagg aggccgctcg cgccaaggcg     1440
gggcagggcg ccccggccgg gacggcagcc gagacggcgg aggccgcccc gtga            1494

<210> SEQ ID NO 31
<211> LENGTH: 497
<212> TYPE: PRT
<213> ORGANISM: Unknown
<220> FEATURE:
<223> OTHER INFORMATION: novel strain

<400> SEQUENCE: 31

Met Ala Ala Ala Asp Glu Glu Ala Gln Ser Ala Ala Gly Pro Ala Ser
1               5                   10                  15

Gly Arg Val Val Ala Val Arg Gly Ala Val Ile Asp Ile Ala Phe Ala
                20                  25                  30

Gln Pro Pro Leu Pro Pro Leu Asp Asp Ala Leu Leu Ile Thr Asp Gly
            35                  40                  45
```

```
Arg Gly Gly Thr Val Leu Val Glu Val Gln Ser His Met Asp Arg His
    50                  55                  60

Thr Val Arg Ala Ile Ala Leu Gln Ala Thr Thr Gly Leu Ser Arg Gly
65              70                  75                  80

Leu Glu Ala Ala Arg Val Gly Gly Pro Val Lys Val Pro Val Gly Asp
                85                  90                  95

His Val Leu Gly Arg Leu Leu Asp Val Thr Gly Ala Ile Gly Asp Lys
            100                 105                 110

Gly Gly Pro Leu Pro Ala Asp Val Pro Thr Arg Pro Ile His His Ala
            115                 120                 125

Pro Pro Ser Phe Ala Ala Gln Gly Gly Thr Ser Asp Leu Phe Arg Thr
    130                 135                 140

Gly Ile Lys Val Ile Asp Leu Leu Ala Pro Leu Ala Gln Gly Gly Lys
145                 150                 155                 160

Ala Ala Met Phe Gly Gly Ala Gly Val Gly Lys Thr Val Leu Val Met
                165                 170                 175

Glu Leu Ile His Ala Met Val Ala Ser Tyr Lys Gly Ile Ser Val Phe
            180                 185                 190

Ala Gly Val Gly Glu Arg Ser Arg Glu Gly His Glu Met Leu Leu Asp
            195                 200                 205

Met Thr Asp Ser Gly Val Leu Asp Arg Thr Val Leu Val Tyr Gly Gln
    210                 215                 220

Met Asn Glu Pro Pro Gly Ala Arg Trp Arg Val Pro Met Thr Ala Leu
225                 230                 235                 240

Thr Ile Ala Glu Tyr Phe Arg Asp Glu Lys His Gln Asn Val Leu Leu
                245                 250                 255

Leu Met Asp Asn Ile Phe Arg Phe Val Gln Ala Gly Ala Glu Val Ser
            260                 265                 270

Gly Leu Leu Gly Arg Pro Pro Ser Arg Val Gly Tyr Gln Pro Thr Leu
            275                 280                 285

Ala Ser Glu Val Ala Ala Leu Gln Glu Arg Ile Thr Ser Val Gly Glu
    290                 295                 300

Ala Ser Val Thr Ala Ile Glu Ala Val Tyr Val Pro Ala Asp Asp Phe
305                 310                 315                 320

Thr Asp Pro Ala Val Thr Thr Ile Ala Ala His Val Asp Ser Met Val
                325                 330                 335

Val Leu Ser Arg Ala Met Ala Ala Glu Gly Met Tyr Pro Ala Val Asp
            340                 345                 350

Pro Ile Ser Ser Ser Ser Val Leu Leu Asp Pro Leu Ile Val Gly Asp
            355                 360                 365

Glu His Ala Arg Val Ala Asn Glu Val Arg Arg Thr Ile Glu His Tyr
    370                 375                 380

Arg Glu Leu Gln Asp Val Ile Ser Leu Leu Gly Met Glu Glu Leu Gly
385                 390                 395                 400

Thr Glu Asp Arg Arg Ile Val Glu Arg Ala Arg Arg Leu Gln Arg Phe
                405                 410                 415

Leu Thr Gln Pro Phe Thr Val Thr Glu Ala Phe Thr Gly Val Pro Gly
            420                 425                 430

Arg Ser Val Ala Ile Ala Asp Thr Ile Ala Gly Cys Arg Met Ile Leu
            435                 440                 445

Ser Gly Ala Cys Asp Asp Trp Gln Glu Ser Ala Leu Tyr Met Val Gly
    450                 455                 460
```

-continued

```
Thr Ile Asp Glu Ala Arg Gln Lys Glu Glu Ala Ala Arg Ala Lys Ala
465             470             475             480

Gly Gln Gly Ala Pro Ala Gly Thr Ala Ala Glu Thr Ala Glu Ala Ala
            485             490             495

Pro

<210> SEQ ID NO 32
<211> LENGTH: 1437
<212> TYPE: DNA
<213> ORGANISM: Unknown
<220> FEATURE:
<223> OTHER INFORMATION: novel strain

<400> SEQUENCE: 32
atggcgaaca aggtcggacg catcacccag atcatcggcg ccgtcgtcga cgtgcagttc       60
gacgggcatc tgccggcgat tctcaacgcg atcgagacca ccaaccaggg caaccggctg      120
gtgctcgaag tggctcagca tctcggcgag aacaccgtgc gctgcatcgc catggatgcc      180
actgaaggcc tggtgcgtgg ccaggaggtg gccgacaccg atgcgcccat ccaggtgccc      240
gtgggcgccg ccaccctcgg ccgcatcatg aacgtgatcg gcgagccggt ggacgagctg      300
ggccccatcg agggcgaagc gctgcgcggc atccatcagc cggccccctc ctatgcggag      360
caggccacgg aagctgagat cctcgtcacc ggcatcaagg tggtggatct gctggcgccc      420
tattccaagg gcgcaaggt gggcctgttc ggcggcgccg gcgtgggcaa gaccgtgctc      480
atcatggagc tgatcaacaa cgtggccaag gcgcacggcg gctattccgt gttcgccggc      540
gtgggtgagc gcaccgcga gggcaacgac ctctaccacg agatgatcga gtccaacgtg      600
aacaaggacc cgcacgagaa caatggctcg gcggccggtt ccaagtgcgc cctggtctat      660
ggccagatga cgagccgcc cggcgcccgc gcccgcgtgg ccctcaccgg cctcaccgtc      720
gccgagcatt tccgcgacca gggccaggac gtgctgttct tcgtggacaa catcttccgc      780
ttcacccagg cgggctccga ggtgtcggcg cttctcggcc gcatccccctc ggcggtgggc      840 taccagccga cgctggccac cgacatgggc cagctgcagg agcgcatcac caccaccacc      900
aagggctcca tcacctcggt gcaggccatc tacgtgccgg cggacgatct gaccgatccg      960
gcgccggccg cctccttcgc ccatctggac gccaccacgg tgctgtcgcg ctccatcgcg     1020
gagaagggca tctacccggc ggtggatccg ctggactcca cctcgcgcat gctgtctccc     1080
gccatcctcg gcgacgagca ctacaacacc gcgcgccagg tgcagcagac cctgcagcgc     1140
tacaaggcgc tccaggacat catcgccatc ctgggcatgg acgaactctc cgaagaggac     1200
aagctcaccg tggcccgcgc ccgcaagatc gagcgcttcc tctcccagcc cttccacgtg     1260
gccgaggtgt tcaccggttc gcccggcaag ctggtcgacc tcgccgacac catcaagggc     1320
ttcaagggcc tggtggacgg caagtacgac tacctgcccg agcaggcctt ctacatggtg     1380
ggcaccatcg aagaagccat cgagaagggc aagaagctgg cggccgaggc ggcctga      1437

<210> SEQ ID NO 33
<211> LENGTH: 478
<212> TYPE: PRT
<213> ORGANISM: Unknown
<220> FEATURE:
<223> OTHER INFORMATION: novel strain

<400> SEQUENCE: 33

Met Ala Asn Lys Val Gly Arg Ile Thr Gln Ile Ile Gly Ala Val Val
1               5               10              15
```

-continued

Asp Val Gln Phe Asp Gly His Leu Pro Ala Ile Leu Asn Ala Ile Glu
                20                      25                      30

Thr Thr Asn Gln Gly Asn Arg Leu Val Leu Glu Val Ala Gln His Leu
            35                      40                      45

Gly Glu Asn Thr Val Arg Cys Ile Ala Met Asp Ala Thr Glu Gly Leu
        50                      55                      60

Val Arg Gly Gln Glu Val Ala Asp Thr Asp Ala Pro Ile Gln Val Pro
65                      70                      75                      80

Val Gly Ala Ala Thr Leu Gly Arg Ile Met Asn Val Ile Gly Glu Pro
                85                      90                      95

Val Asp Glu Leu Gly Pro Ile Glu Gly Glu Ala Leu Arg Gly Ile His
            100                     105                     110

Gln Pro Ala Pro Ser Tyr Ala Glu Gln Ala Thr Glu Ala Glu Ile Leu
            115                     120                     125

Val Thr Gly Ile Lys Val Val Asp Leu Leu Ala Pro Tyr Ser Lys Gly
        130                     135                     140

Gly Lys Val Gly Leu Phe Gly Gly Ala Gly Val Gly Lys Thr Val Leu
145                     150                     155                     160

Ile Met Glu Leu Ile Asn Asn Val Ala Lys Ala His Gly Gly Tyr Ser
                165                     170                     175

Val Phe Ala Gly Val Gly Glu Arg Thr Arg Glu Gly Asn Asp Leu Tyr
            180                     185                     190

His Glu Met Ile Glu Ser Asn Val Asn Lys Asp Pro His Glu Asn Asn
            195                     200                     205

Gly Ser Ala Ala Gly Ser Lys Cys Ala Leu Val Tyr Gly Gln Met Asn
        210                     215                     220

Glu Pro Pro Gly Ala Arg Ala Arg Val Ala Leu Thr Gly Leu Thr Val
225                     230                     235                     240

Ala Glu His Phe Arg Asp Gln Gly Gln Asp Val Leu Phe Phe Val Asp
                245                     250                     255

Asn Ile Phe Arg Phe Thr Gln Ala Gly Ser Glu Val Ser Ala Leu Leu
            260                     265                     270

Gly Arg Ile Pro Ser Ala Val Gly Tyr Gln Pro Thr Leu Ala Thr Asp
            275                     280                     285

Met Gly Gln Leu Gln Glu Arg Ile Thr Thr Thr Thr Lys Gly Ser Ile
        290                     295                     300

Thr Ser Val Gln Ala Ile Tyr Val Pro Ala Asp Asp Leu Thr Asp Pro
305                     310                     315                     320

Ala Pro Ala Ala Ser Phe Ala His Leu Asp Ala Thr Thr Val Leu Ser
                325                     330                     335

Arg Ser Ile Ala Glu Lys Gly Ile Tyr Pro Ala Val Asp Pro Leu Asp
            340                     345                     350

Ser Thr Ser Arg Met Leu Ser Pro Ala Ile Leu Gly Asp Glu His Tyr
            355                     360                     365

Asn Thr Ala Arg Gln Val Gln Gln Thr Leu Gln Arg Tyr Lys Ala Leu
        370                     375                     380

Gln Asp Ile Ile Ala Ile Leu Gly Met Asp Glu Leu Ser Glu Glu Asp
385                     390                     395                     400

Lys Leu Thr Val Ala Arg Ala Arg Lys Ile Glu Arg Phe Leu Ser Gln
                405                     410                     415

Pro Phe His Val Ala Glu Val Phe Thr Gly Ser Pro Gly Lys Leu Val
                420                     425                     430

Asp Leu Ala Asp Thr Ile Lys Gly Phe Lys Gly Leu Val Asp Gly Lys

```
         435                440                445
Tyr Asp Tyr Leu Pro Glu Gln Ala Phe Tyr Met Val Gly Thr Ile Glu
    450                455                460

Glu Ala Ile Glu Lys Gly Lys Lys Leu Ala Ala Glu Ala Ala
465                470                475
```

<210> SEQ ID NO 34
<211> LENGTH: 876
<212> TYPE: DNA
<213> ORGANISM: Unknown
<220> FEATURE:
<223> OTHER INFORMATION: novel strain

<400> SEQUENCE: 34

```
atggcgagtc tgaaggacct gagaaaccgc attgcctcgg tgaaggcgac gcagaagatc    60
accaaggcga tgcagatggt cgccgcggcg aagctgcgtc gcgcccaggc ggcggctgaa   120
gcggcccgtc cctatgcgga acgcatggag acggtgctcg gaaatcttgc ctccggcatg   180
gtggtgggcg cgcaggcgcc tgttctcatg accgggacgg gcaagagcga cacccacctg   240
ctgctggtgt gcaccggcga gcgcggcctg tgcggcgcct tcaactcgtc catcgtgcgc   300
ttcgcccgcg agcgggcgca gctgctgctg gccgagggca agaaggtgaa aatcctgtgc   360
gtgggccgca agggccacga gcagctgcgc cgcatctacc ggacaacat catcgacgtg    420 gtggacctgc gcgcggtgcg caacatcggc ttcaaggagg ccgacgccat cgcccgcaag   480
gtgctggccc tgctcgatga aggcgcattc gacgtctgca cgctcttcta ctcccacttc   540
aggagcgtga tcgcccaggt gccgacggcc agcagctca ttccggccac cttcgacgag    600
cggccggccg tcgccgatgc gccggtctat gaatatgagc cggaggagga ggagatcctc   660
gccgagctgc tgccgcgcaa cgtggcggtg cagatcttca aggccctcct cgagaaccag   720
gcttcttctt atggctccca gatgagcgcc atggacaacg ccacgcgcaa tgcgggcgag   780
atgatcaaga agcagacgct cacctacaac cgtacccgcc aggccatgat cacgaaggaa   840
ctcatcgaga tcatctccgg cgccgaggcc gtctga                            876
```

<210> SEQ ID NO 35
<211> LENGTH: 291
<212> TYPE: PRT
<213> ORGANISM: Unknown
<220> FEATURE:
<223> OTHER INFORMATION: novel strain

<400> SEQUENCE: 35

```
Met Ala Ser Leu Lys Asp Leu Arg Asn Arg Ile Ala Ser Val Lys Ala
1                5                 10                 15

Thr Gln Lys Ile Thr Lys Ala Met Gln Met Val Ala Ala Ala Lys Leu
            20                 25                 30

Arg Arg Ala Gln Ala Ala Ala Glu Ala Ala Arg Pro Tyr Ala Glu Arg
        35                 40                 45

Met Glu Thr Val Leu Gly Asn Leu Ala Ser Gly Met Val Val Gly Ala
    50                 55                 60

Gln Ala Pro Val Leu Met Thr Gly Thr Gly Lys Ser Asp Thr His Leu
65                 70                 75                 80

Leu Leu Val Cys Thr Gly Glu Arg Gly Leu Cys Gly Ala Phe Asn Ser
                85                 90                 95

Ser Ile Val Arg Phe Ala Arg Glu Arg Ala Gln Leu Leu Leu Ala Glu
            100                105                110
```

```
Gly Lys Lys Val Lys Ile Leu Cys Val Gly Arg Lys Gly His Glu Gln
        115                 120                 125

Leu Arg Arg Ile Tyr Pro Asp Asn Ile Ile Asp Val Val Asp Leu Arg
        130                 135                 140

Ala Val Arg Asn Ile Gly Phe Lys Glu Ala Asp Ala Ile Ala Arg Lys
145                 150                 155                 160

Val Leu Ala Leu Leu Asp Glu Gly Ala Phe Asp Val Cys Thr Leu Phe
                165                 170                 175

Tyr Ser His Phe Arg Ser Val Ile Ala Gln Val Pro Thr Ala Gln Gln
                180                 185                 190

Leu Ile Pro Ala Thr Phe Asp Glu Arg Pro Ala Val Ala Asp Ala Pro
                195                 200                 205

Val Tyr Glu Tyr Glu Pro Glu Glu Glu Ile Leu Ala Glu Leu Leu
        210                 215                 220

Pro Arg Asn Val Ala Val Gln Ile Phe Lys Ala Leu Leu Glu Asn Gln
225                 230                 235                 240

Ala Ser Phe Tyr Gly Ser Gln Met Ser Ala Met Asp Asn Ala Thr Arg
                245                 250                 255

Asn Ala Gly Glu Met Ile Lys Lys Gln Thr Leu Thr Tyr Asn Arg Thr
                260                 265                 270

Arg Gln Ala Met Ile Thr Lys Glu Leu Ile Glu Ile Ile Ser Gly Ala
        275                 280                 285

Glu Ala Val
    290
```

```
<210> SEQ ID NO 36
<211> LENGTH: 1530
<212> TYPE: DNA
<213> ORGANISM: Unknown
<220> FEATURE:
<223> OTHER INFORMATION: novel strain

<400> SEQUENCE: 36
atggacattc gagccgctga aatctctgcc atcctgaaag agcagatcca gaatttcggc      60
caggaggcgg aagtctccga ggtgggtcag gttctgtccg tgggtgacgg catcgcgcgc     120
gtctacggcc tcgacaacgt ccaggcgggc gagatggtcg agttcgagaa cggcacgcgc     180
ggcatggcgc tgaacctcga gctcgacaat gtcggcatcg tgatcttcgg ttccgaccgc     240
gagatcaagg aaggccagac cgtcaagcgg accggcgcca tcgtggacgc ccccgtcggc     300
aagggcctgc tcggccgcgt cgtggacgct ctcggcaacc cgatcgacgg caagggcccg     360
atcatgttca ccgagcgtcg ccgggtcgac gtgaaggcgc cggcatcat cccgcgcaag     420 tcggtgcacg agcccatgca gaccggcctg aaggccatcg atgcgctcat ccccatcggc     480
cgcggccagc gcgagctcat catcggcgac cgccagaccg gcaagaccgc cgtggcgctc     540
gactcgatcc tgaaccagaa gcccatcaac caggggcgacg acgagaaggc caagctctac     600
tgcgtctatg tcgcggtggg ccagaagcgt tccactgtcg cgcagttcgt gaaggtgctc     660
gaggagcacg gcgcgctgga atattccatc gtcgtcgccg ccaccgcctc ggacgcggcc     720
cccatgcagt cctggcgcc gttcaccggc accgccatgg gcgagtattt ccgcgacaac     780
ggcatgcacg ccctcatcat ccatgatgac ctgtccaagc aggccgtggc ctaccgccag     840
atgtcgctgc tgctgcgccg cccgccgggc gcgagggcct atcccggcga tgtgttctac     900
ctgcactccc gcctcttgga gcgcgccgcc aagctcaatg acgagcacgg cgccggctcg     960
ctgaccgccc tgccggtgat cgagacccag gccaacgacg tgtcggccta catcccgacc    1020
```

-continued

```
aacgtgatct ccatcaccga cggtcagatc ttccttgaat ccgatctgtt ctaccagggc    1080
atccgcccgg cggtgaacgt gggcctgtcg gtgtcgcgcg tgggctcttc ggcccagatc    1140
aaggcgatga agcaggtggc cggcaagatc aagggcgagc tcgcccagta tcgcgagctg    1200
gcggccttcg cccagttcgg ttcggacctg gacgcggcca cccagaagct gctgaaccgc    1260
ggcgcccgcc tcaccgagct gctgaagcag agccagttct cgcccctcaa ggtggaggag    1320
caggtggcgt gatctatgc cggcaccaat ggctatctcg atccgctgcc ggtctccaag    1380
gtgcgcgagt cgagcaggg tctgctcctg tcgctgcgct cgcagcatcc ggagatcctg    1440
gacgccatcc gcacgtccaa ggagctttcc aaggacaccg ccgagaagct gacgaaggcc    1500
atcgacgcct cgccaagag cttctcctga                                      1530
```

```
<210> SEQ ID NO 37
<211> LENGTH: 509
<212> TYPE: PRT
<213> ORGANISM: Unknown
<220> FEATURE:
<223> OTHER INFORMATION: novel strain

<400> SEQUENCE: 37

Met Asp Ile Arg Ala Ala Glu Ile Ser Ala Ile Leu Lys Glu Gln Ile
1               5                   10                  15

Gln Asn Phe Gly Gln Glu Ala Glu Val Ser Glu Val Gly Gln Val Leu
            20                  25                  30

Ser Val Gly Asp Gly Ile Ala Arg Val Tyr Gly Leu Asp Asn Val Gln
        35                  40                  45

Ala Gly Glu Met Val Glu Phe Glu Asn Gly Thr Arg Gly Met Ala Leu
    50                  55                  60

Asn Leu Glu Leu Asp Asn Val Gly Ile Val Ile Phe Gly Ser Asp Arg
65                  70                  75                  80

Glu Ile Lys Glu Gly Gln Thr Val Lys Arg Thr Gly Ala Ile Val Asp
                85                  90                  95

Ala Pro Val Gly Lys Gly Leu Leu Gly Arg Val Val Asp Ala Leu Gly
            100                 105                 110

Asn Pro Ile Asp Gly Lys Gly Pro Ile Met Phe Thr Glu Arg Arg Arg
        115                 120                 125

Val Asp Val Lys Ala Pro Gly Ile Ile Pro Arg Lys Ser Val His Glu
    130                 135                 140

Pro Met Gln Thr Gly Leu Lys Ala Ile Asp Ala Leu Ile Pro Ile Gly
145                 150                 155                 160

Arg Gly Gln Arg Glu Leu Ile Ile Gly Asp Arg Gln Thr Gly Lys Thr
                165                 170                 175

Ala Val Ala Leu Asp Ser Ile Leu Asn Gln Lys Pro Ile Asn Gln Gly
            180                 185                 190

Asp Asp Glu Lys Ala Lys Leu Tyr Cys Val Tyr Val Ala Val Gly Gln
        195                 200                 205

Lys Arg Ser Thr Val Ala Gln Phe Val Lys Val Leu Glu Glu His Gly
    210                 215                 220

Ala Leu Glu Tyr Ser Ile Val Val Ala Ala Thr Ala Ser Asp Ala Ala
225                 230                 235                 240

Pro Met Gln Phe Leu Ala Pro Phe Thr Gly Thr Ala Met Gly Glu Tyr
                245                 250                 255

Phe Arg Asp Asn Gly Met His Ala Leu Ile Ile His Asp Asp Leu Ser
            260                 265                 270
```

-continued

```
Lys Gln Ala Val Ala Tyr Arg Gln Met Ser Leu Leu Leu Arg Arg Pro
    275                 280                 285

Pro Gly Arg Glu Ala Tyr Pro Gly Asp Val Phe Tyr Leu His Ser Arg
    290                 295                 300

Leu Leu Glu Arg Ala Ala Lys Leu Asn Asp Glu His Gly Ala Gly Ser
305                 310                 315                 320

Leu Thr Ala Leu Pro Val Ile Glu Thr Gln Ala Asn Asp Val Ser Ala
                325                 330                 335

Tyr Ile Pro Thr Asn Val Ile Ser Ile Thr Asp Gly Gln Ile Phe Leu
                340                 345                 350

Glu Ser Asp Leu Phe Tyr Gln Gly Ile Arg Pro Ala Val Asn Val Gly
                355                 360                 365

Leu Ser Val Ser Arg Val Gly Ser Ser Ala Gln Ile Lys Ala Met Lys
    370                 375                 380

Gln Val Ala Gly Lys Ile Lys Gly Glu Leu Ala Gln Tyr Arg Glu Leu
385                 390                 395                 400

Ala Ala Phe Ala Gln Phe Gly Ser Asp Leu Asp Ala Ala Thr Gln Lys
                405                 410                 415

Leu Leu Asn Arg Gly Ala Arg Leu Thr Glu Leu Leu Lys Gln Ser Gln
                420                 425                 430

Phe Ser Pro Leu Lys Val Glu Glu Gln Val Ala Val Ile Tyr Ala Gly
                435                 440                 445

Thr Asn Gly Tyr Leu Asp Pro Leu Pro Val Ser Lys Val Arg Glu Phe
    450                 455                 460

Glu Gln Gly Leu Leu Leu Ser Leu Arg Ser Gln His Pro Glu Ile Leu
465                 470                 475                 480

Asp Ala Ile Arg Thr Ser Lys Glu Leu Ser Lys Asp Thr Ala Glu Lys
                485                 490                 495

Leu Thr Lys Ala Ile Asp Ala Phe Ala Lys Ser Phe Ser
                500                 505

<210> SEQ ID NO 38
<211> LENGTH: 555
<212> TYPE: DNA
<213> ORGANISM: Unknown
<220> FEATURE:
<223> OTHER INFORMATION: novel strain

<400> SEQUENCE: 38
gtggcggaaa cgatcgtgtc aggcatggcg ggacgctatg cgaccgcgct gttcgagctg      60
gcggacgaag ccggtgccat cgattccgtc caggcggatc ttgatcgcct gtccggcctt     120
ctggccgaga gcgcggatct ggcgcggctg gtcaagagcc cggtcttcac cgccgagcag     180
cagctcggcg cgatggcggc cattctcgat caagcaggca tttccggcct tgcgggcaaa     240
ttcgtgaagc tggtggcgca gaaccgccgc ctgttcgcac tgccgcgcat gattgccgaa     300
tacgccgtcc tggtggcccg gaagaagggc gagacctcgg cgagcgtgac cgttgccacc     360
cccctgagcg atgagcatct ggccacgctc aaggcggccc tggctgaaaa gaccggcaag     420
gacgtgaagc tcgacgtcac cgtcgatccg tccatcctcg gtggtctcat cgtgaagctc     480
ggctcgcgca tggtcgatgc ttccctgaag accaaactca attctatccg gcatgcgatg     540
aaagaggtcc gctga                                                      555

<210> SEQ ID NO 39
<211> LENGTH: 184
```

<212> TYPE: PRT
<213> ORGANISM: Unknown
<220> FEATURE:
<223> OTHER INFORMATION: novel strain

<400> SEQUENCE: 39

```
Met Ala Glu Thr Ile Val Ser Gly Met Ala Gly Arg Tyr Ala Thr Ala
1               5                   10                  15

Leu Phe Glu Leu Ala Asp Glu Ala Gly Ala Ile Asp Ser Val Gln Ala
            20                  25                  30

Asp Leu Asp Arg Leu Ser Gly Leu Leu Ala Glu Ser Ala Asp Leu Ala
            35                  40                  45

Arg Leu Val Lys Ser Pro Val Phe Thr Ala Glu Gln Gln Leu Gly Ala
        50                  55                  60

Met Ala Ala Ile Leu Asp Gln Ala Gly Ile Ser Gly Leu Ala Gly Lys
65                  70                  75                  80

Phe Val Lys Leu Val Ala Gln Asn Arg Arg Leu Phe Ala Leu Pro Arg
                85                  90                  95

Met Ile Ala Glu Tyr Ala Val Leu Val Ala Arg Lys Lys Gly Glu Thr
            100                 105                 110

Ser Ala Ser Val Thr Val Ala Thr Pro Leu Ser Asp Glu His Leu Ala
            115                 120                 125

Thr Leu Lys Ala Ala Leu Ala Glu Lys Thr Gly Lys Asp Val Lys Leu
        130                 135                 140

Asp Val Thr Val Asp Pro Ser Ile Leu Gly Gly Leu Ile Val Lys Leu
145                 150                 155                 160

Gly Ser Arg Met Val Asp Ala Ser Leu Lys Thr Lys Leu Asn Ser Ile
                165                 170                 175

Arg His Ala Met Lys Glu Val Arg
                180
```

<210> SEQ ID NO 40
<211> LENGTH: 492
<212> TYPE: DNA
<213> ORGANISM: Unknown
<220> FEATURE:
<223> OTHER INFORMATION: novel strain

<400> SEQUENCE: 40

```
atgaccgaaa tggaactggc tgagctctgg gtcgccatcg ccttcctggt tttcgtaggc        60
ctcctgatct atgcgggcgc ccaccgcgcc atcgtctccg ccctggattc ccgcggctcg       120
cgcatcgcct cggaactgga ggaggcccgt cggctcaagg aagaggccca gaagctggtg       180
gccgaattca gcgcaagca gcgcgaggcc gaggccgagg ccgaatccat cgtcaccggc       240
gccaaggccg aggccgagcg cctcgccgcc gaggccaagg cgaagatcga ggatttcgtc       300
acccgccgca ccaagatggc cgaggacaag atcgcccagg ccgagcatca ggctctggcg       360
gacgtgaagt ccatcgccgc cgaggcggcg gccaaggcgg ccgaggtgat cctcggcgcc       420
caggccaccg gcgcggtggc ggagcgtctg ctgtcgggcg ccatctccga ggtcaagacc       480
aagctcaact ga                                                           492
```

<210> SEQ ID NO 41
<211> LENGTH: 163
<212> TYPE: PRT
<213> ORGANISM: Unknown
<220> FEATURE:
<223> OTHER INFORMATION: novel strain

<400> SEQUENCE: 41

```
Met Thr Glu Met Glu Leu Ala Glu Leu Trp Val Ala Ile Ala Phe Leu
1               5                   10                  15

Val Phe Val Gly Leu Leu Ile Tyr Ala Gly Ala His Arg Ala Ile Val
                20                  25                  30

Ser Ala Leu Asp Ser Arg Gly Ser Arg Ile Ala Ser Glu Leu Glu Glu
            35                  40                  45

Ala Arg Arg Leu Lys Glu Glu Ala Gln Lys Leu Val Ala Glu Phe Lys
        50                  55                  60

Arg Lys Gln Arg Glu Ala Glu Ala Glu Ala Glu Ser Ile Val Thr Gly
65                  70                  75                  80

Ala Lys Ala Glu Ala Glu Arg Leu Ala Ala Glu Ala Lys Ala Lys Ile
                85                  90                  95

Glu Asp Phe Val Thr Arg Arg Thr Lys Met Ala Glu Asp Lys Ile Ala
                100                 105                 110

Gln Ala Glu His Gln Ala Leu Ala Asp Val Lys Ser Ile Ala Ala Glu
            115                 120                 125

Ala Ala Ala Lys Ala Ala Glu Val Ile Leu Gly Ala Gln Ala Thr Gly
        130                 135                 140

Ala Val Ala Glu Arg Leu Leu Ser Gly Ala Ile Ser Glu Val Lys Thr
145                 150                 155                 160

Lys Leu Asn
```

<210> SEQ ID NO 42
<211> LENGTH: 729
<212> TYPE: DNA
<213> ORGANISM: Unknown
<220> FEATURE:
<223> OTHER INFORMATION: novel strain

<400> SEQUENCE: 42

```
atgatgattg catggaagcg gaccttcgca gtcgtgacct tcggggccgc cctgatggcc    60
atgcccgtcg cgggcgtggt cgcagctgag acttctcccg ctccggcggc agtggcgcag   120
gccgatcatg cggtgcccac cgaggcggcc ggccagggca ccgccgatgc ggcccatgcc   180
gccgcgccgg gcgaggccgc ccatggtggc gcggccaagc acgaaaccca tttcccgccc   240
ttcgacggca ccaccttcgc ctcccagttg ctgtggctcg ccgtcacctt cggcctgctt   300
tactacctca tgagcaaggt cacgctgccg cgcatcggcc gcatcctgga agagcgccac   360
gaccgcatcg ccgatgatct ggaggaagcc tccaagcatc gcgccgagag cgaggccgcc   420
cagcgggcct atgagaaggc gctgagcgag gcccgcgcga aggcccattc catcgccgcg   480
gaaacccgcg accgccttgc cgcccacgcc gacaccaacc gcaaggcgct ggagagcgag   540
ctcaccgcca agctgcaggc ggccgaggag cgcatcgcca ccaccaagag cgaagccctc   600
acccatgtgc gcggcatcgc ggtggacgcc acccaatcca tcgtctccac cctcatcggt   660
gtcgcgcccg cggcggccga cgtggaaaaa gcggtggacg cgcccctgtc ccagcacggc   720
caggcctga                                                          729
```

<210> SEQ ID NO 43
<211> LENGTH: 242
<212> TYPE: PRT
<213> ORGANISM: Unknown
<220> FEATURE:
<223> OTHER INFORMATION: novel strain

<400> SEQUENCE: 43

```
Met Met Ile Ala Trp Lys Arg Thr Phe Ala Val Val Thr Phe Gly Ala
1               5                   10                  15

Ala Leu Met Ala Met Pro Val Ala Gly Val Val Ala Ala Glu Thr Ser
            20                  25                  30

Pro Ala Pro Ala Ala Val Ala Gln Ala Asp His Ala Val Pro Thr Glu
        35                  40                  45

Ala Ala Gly Gln Gly Thr Ala Asp Ala Ala His Ala Ala Ala Pro Gly
    50                  55                  60

Glu Ala Ala His Gly Gly Ala Ala Lys His Glu Thr His Phe Pro Pro
65                  70                  75                  80

Phe Asp Gly Thr Thr Phe Ala Ser Gln Leu Leu Trp Leu Ala Val Thr
                85                  90                  95

Phe Gly Leu Leu Tyr Tyr Leu Met Ser Lys Val Thr Leu Pro Arg Ile
            100                 105                 110

Gly Arg Ile Leu Glu Glu Arg His Asp Arg Ile Ala Asp Asp Leu Glu
        115                 120                 125

Glu Ala Ser Lys His Arg Ala Glu Ser Glu Ala Ala Gln Arg Ala Tyr
    130                 135                 140

Glu Lys Ala Leu Ser Glu Ala Arg Ala Lys Ala His Ser Ile Ala Ala
145                 150                 155                 160

Glu Thr Arg Asp Arg Leu Ala Ala His Ala Asp Thr Asn Arg Lys Ala
                165                 170                 175

Leu Glu Ser Glu Leu Thr Ala Lys Leu Gln Ala Ala Glu Glu Arg Ile
            180                 185                 190

Ala Thr Thr Lys Ser Glu Ala Leu Thr His Val Arg Gly Ile Ala Val
            195                 200                 205

Asp Ala Thr Gln Ser Ile Val Ser Thr Leu Ile Gly Val Ala Pro Ala
    210                 215                 220

Ala Ala Asp Val Glu Lys Ala Val Asp Gly Ala Leu Ser Gln His Gly
225                 230                 235                 240

Gln Ala
```

```
<210> SEQ ID NO 44
<211> LENGTH: 228
<212> TYPE: DNA
<213> ORGANISM: Unknown
<220> FEATURE:
<223> OTHER INFORMATION: novel strain

<400> SEQUENCE: 44
atggaagcgg aagctggaaa gttcatcggt gccggcctcg cctgcctcgg catgggtctc        60
gctggcgtcg gcgtcggtaa catcttcggt aacttcctct ccggcgccct gcgcaacccg       120
tccgctgccg acggccagtt cgcccgcgcc ttcatcggcg ccgccctcgc ggaaggtctc       180
ggcatcttct cgctggtcgt tgcgctcgtc ctgctgttcg tggcctga                    228
```

```
<210> SEQ ID NO 45
<211> LENGTH: 75
<212> TYPE: PRT
<213> ORGANISM: Unknown
<220> FEATURE:
<223> OTHER INFORMATION: novel strain

<400> SEQUENCE: 45

Met Glu Ala Glu Ala Gly Lys Phe Ile Gly Ala Gly Leu Ala Cys Leu
1               5                   10                  15
```

```
Gly Met Gly Leu Ala Gly Val Gly Val Gly Asn Ile Phe Gly Asn Phe
            20                  25                  30

Leu Ser Gly Ala Leu Arg Asn Pro Ser Ala Ala Asp Gly Gln Phe Ala
        35                  40                  45

Arg Ala Phe Ile Gly Ala Ala Leu Ala Glu Gly Leu Gly Ile Phe Ser
    50                  55                  60

Leu Val Val Ala Leu Val Leu Leu Phe Val Ala
65                  70                  75
```

<210> SEQ ID NO 46
<211> LENGTH: 753
<212> TYPE: DNA
<213> ORGANISM: Unknown
<220> FEATURE:
<223> OTHER INFORMATION: novel strain

<400> SEQUENCE: 46

```
atgaccgtcg atccgatcca ccagttcgag atcaagcgct acgtggatct gctgaacgtc        60
ggcggtgtcc agttctcctt caccaacgca acggtgttca tgattggcat cgtcctggtg       120
attttcttct tcctgacttt cgcgacacgc ggtcgcaccc ttgtgccggg ccggatgcag       180
tcggcggcgg agctgagcta cgagttcatc gccaagatgg tgcgcgacgc ggccggcagc       240
gagggaatgg tgttctttcc cttcgtcttc tcgctcttca tgttcgtgct ggtggcgaac       300 gtattgggc tcatccccta caccttcacg gtgaccgccc acctcatcgt caccgccgcc       360
ctggcggcga cggtgatcct caccgtcatc atctacggct cgtgcggca cggcacccac       420 ttcctgcacc tgttcgtgcc gtcgggcgtg ccgggcttcc tcctgccctt cctcgtggtg       480
atcgaggtgg tgtcgttcct gtcgcggccc atcagcctct cgctgcgtct gttcgccaac       540
atgctggcgg ccacatcgc cctcaaggtg ttcgccttct tcgtcgtggg actggcctcg       600
gccggcgcga tcggctggtt cggcgccacc ctgcccttct tcatgatcgt ggcgctcacc       660
gcgctggagc tgctggtggc ggtgctgcag gcctacgtgt tcgcggtgct gacctcgatc       720
tacctcaacg acgccatcca tcccggccac tga                                    753
```

<210> SEQ ID NO 47
<211> LENGTH: 250
<212> TYPE: PRT
<213> ORGANISM: Unknown
<220> FEATURE:
<223> OTHER INFORMATION: novel strain

<400> SEQUENCE: 47

```
Met Thr Val Asp Pro Ile His Gln Phe Glu Ile Lys Arg Tyr Val Asp
1               5                   10                  15

Leu Leu Asn Val Gly Gly Val Gln Phe Ser Phe Thr Asn Ala Thr Val
            20                  25                  30

Phe Met Ile Gly Ile Val Leu Val Ile Phe Phe Leu Thr Phe Ala
        35                  40                  45

Thr Arg Gly Arg Thr Leu Val Pro Gly Arg Met Gln Ser Ala Ala Glu
    50                  55                  60

Leu Ser Tyr Glu Phe Ile Ala Lys Met Val Arg Asp Ala Ala Gly Ser
65                  70                  75                  80

Glu Gly Met Val Phe Phe Pro Phe Val Phe Ser Leu Phe Met Phe Val
                85                  90                  95

Leu Val Ala Asn Val Leu Gly Leu Ile Pro Tyr Thr Phe Thr Val Thr
                100                 105                 110
```

-continued

```
Ala His Leu Ile Val Thr Ala Ala Leu Ala Ala Thr Val Ile Leu Thr
        115                 120                 125

Val Ile Ile Tyr Gly Phe Val Arg His Gly Thr His Phe Leu His Leu
    130                 135                 140

Phe Val Pro Ser Gly Val Pro Gly Phe Leu Leu Pro Phe Leu Val Val
145                 150                 155                 160

Ile Glu Val Val Ser Phe Leu Ser Arg Pro Ile Ser Leu Ser Leu Arg
                165                 170                 175

Leu Phe Ala Asn Met Leu Ala Gly His Ile Ala Leu Lys Val Phe Ala
                180                 185                 190

Phe Phe Val Val Gly Leu Ala Ser Ala Gly Ala Ile Gly Trp Phe Gly
                195                 200                 205

Ala Thr Leu Pro Phe Phe Met Ile Val Ala Leu Thr Ala Leu Glu Leu
        210                 215                 220

Leu Val Ala Val Leu Gln Ala Tyr Val Phe Ala Val Leu Thr Ser Ile
225                 230                 235                 240

Tyr Leu Asn Asp Ala Ile His Pro Gly His
                245                 250
```

```
<210> SEQ ID NO 48
<211> LENGTH: 390
<212> TYPE: DNA
<213> ORGANISM: Unknown
<220> FEATURE:
<223> OTHER INFORMATION: novel strain

<400> SEQUENCE: 48
atgtccgagc cgaatgatcc atcccgcagg gacggtgcga aggcgaaaga cgagacgcag      60
gactcccggc ccggtgaggc ggatcttgct cggcgcctcg atgcgctcgg cacctccatc     120
ggtcaggtca agtccagaag cggggagccc gcggcgacgc cgcgcaagga cacctcctcg     180
gcctccggcg cggccctggc gtttcggctg ggcgccgagt ttgtttcagg cgtgctggtg     240
ggctcgctca tcggctacgg gttggattat gcgtttgcga tttcgccctg ggggctgatc     300
gccttcacgc tgatcggctt tgccgccggc gtcctgaaca tgctgcgcgt ggcgaacagc     360
gatgccaagc gccacagcgc ggacaggtga                                      390
```

```
<210> SEQ ID NO 49
<211> LENGTH: 129
<212> TYPE: PRT
<213> ORGANISM: Unknown
<220> FEATURE:
<223> OTHER INFORMATION: novel strain

<400> SEQUENCE: 49
```

```
Met Ser Glu Pro Asn Asp Pro Ser Arg Arg Asp Gly Ala Lys Ala Lys
1               5                   10                  15

Asp Glu Thr Gln Asp Ser Arg Pro Gly Glu Ala Asp Leu Ala Arg Arg
                20                  25                  30

Leu Asp Ala Leu Gly Thr Ser Ile Gly Gln Val Lys Ser Arg Ser Gly
            35                  40                  45

Glu Pro Ala Ala Thr Pro Arg Lys Asp Thr Ser Ser Ala Ser Gly Ala
        50                  55                  60

Ala Leu Ala Phe Arg Leu Gly Ala Glu Phe Val Ser Gly Val Leu Val
65                  70                  75                  80

Gly Ser Leu Ile Gly Tyr Gly Leu Asp Tyr Ala Phe Ala Ile Ser Pro
                85                  90                  95
```

```
Trp Gly Leu Ile Ala Phe Thr Leu Ile Gly Phe Ala Ala Gly Val Leu
        100                 105                 110

Asn Met Leu Arg Val Ala Asn Ser Asp Ala Lys Arg His Ser Ala Asp
        115                 120                 125

Arg

<210> SEQ ID NO 50
<211> LENGTH: 1929
<212> TYPE: DNA
<213> ORGANISM: Unknown
<220> FEATURE:
<223> OTHER INFORMATION: novel strain

<400> SEQUENCE: 50
atgagttcgc tctccgccac tattcaacag gtcttcaacg agccgggctg cgcgaagaac      60
cagaataagt ccgaggcgga gaagaagaag ggctgcacca agcagctgca acccggcgga     120
gcggccggcg gctgcgcgtt cgacggcgcg aagatcgcgc tccagccctt gaccgacgtc     180
gcccacctgg tgcacggccc catcgcctgc gaaggcaatt cctgggacaa tcgtggcgcc     240
aagtcctccg gctcgaacat ctggcgcacc ggcttcacca cggacatcaa cgaaaccgac     300
gtggtgttcg gcggcgagaa gcgtctgttc aagtccatca ggaaatcat cgagaagtac     360 gacccgccgg ccgtcttcgt ctatcagacc tgcgtccccg ccatgatcgg cgacgacatc     420
gacgcggtgt gcaaggcggc cagggagaag ttcggaaagc cggtgatccc gatcaattcc     480
cccggcttcg tggggccgaa gaatctcggc aacaagctcg ccggcgaggc gctcctcgac     540
catgtgatcg gcaccgagga gcccgattac acgacggcct acgacatcaa catcatcggc     600
gaatacaatc tctccggcga gttgtggcag gtgaagccgc tgctggacga gctgggcatc     660
cgcatcctcg cctgcatctc cggcgacggg aagtacaagg atgtggcgtc ctcccaccgc     720
gccaaggcgg cgatgatggt gtgctccaag gccatgatca acgtggcccg caagatggag     780
gagcgctacg acatcccctt cttcgaaggc tccttctacg gcatcgagga tagctccgat     840
tccctgcgcg agattgcgcg catgctcatc gagaagggcg ccgatccgga gctgatggac     900
cgcaccgagg cgctgattga gcgggaagag aagaaggcgt gggacgccat cgccgcctac     960 aagcccccgct tcaaggacaa gaaggtgctg ctcatcaccg gcggcgtgaa atcctggtcg    1020
gtggtggcag cgctccagga agccggcctc gaactggtgg gcacctcggt gaagaagtcc    1080
accaaggagg acaaggagcg catcaaggaa ctgatgggcc aggacgccca catgatcgac    1140
gacatgacgc cccgcgaaat gtacaagatg ctgaaggacg ccaaggcgga catcatgctc    1200
tcgggcgggc gctcgcaatt catcgcgctc aaggccgcca tgccctggct cgacatcaac    1260
caggagcgcc accacgccta tatgggctat gtgggcatgg tgaagctggt cgaggagatc    1320
gacaaggcgc tctacaatcc cgtgtgggaa caggtgcgca agcccgcccc gtgggaaaat    1380
ccggaagaca cctggcaggc ccgtgcgctc gccgaaatgg aggcggaggc cgccgcgctc    1440
gccgccgatc cggtgcgcgc ggaagaggtg cgccggtcca agaagatctg caattgcaag    1500
agcgtcgacc tcggaaccat tgaggacgcc atcaaggctc acgcgctgac caccgtggag    1560
ggtgtgcgag agcacaccaa tgcctcggga ggctgcggag cctgcagcgg cggatcgag    1620 gagatcttcg aggccgtggg cgttgtcgcc gccccgcctc ccgcggaggc cgccccgtct    1680
ccgcaggaga tcgcgcccga tccgctcgct gcggaggaaa agcgccgcgc caagaaggcc    1740
tgcggctgca aggaggtagc ggtcggcacc attgaggatg ccatccgcgc caagggtctg    1800
cgaaacatcg cggaggtgcg tgcggccacc gatgccaaca ccggctgcgg caattgccag    1860
```

-continued gagcgggtgg aggggcatcct cgaccgggtt ctcgccgagg cggcctcaga actccaggcg    1920
gcggaatag                                                             1929

<210> SEQ ID NO 51
<211> LENGTH: 642
<212> TYPE: PRT
<213> ORGANISM: Unknown
<220> FEATURE:
<223> OTHER INFORMATION: novel strain

<400> SEQUENCE: 51

Met Ser Ser Leu Ser Ala Thr Ile Gln Gln Val Phe Asn Glu Pro Gly
1               5                   10                  15

Cys Ala Lys Asn Gln Asn Lys Ser Glu Ala Glu Lys Lys Gly Cys
            20                  25                  30

Thr Lys Gln Leu Gln Pro Gly Gly Ala Ala Gly Gly Cys Ala Phe Asp
        35                  40                  45

Gly Ala Lys Ile Ala Leu Gln Pro Leu Thr Asp Val Ala His Leu Val
    50                  55                  60

His Gly Pro Ile Ala Cys Glu Gly Asn Ser Trp Asp Asn Arg Gly Ala
65                  70                  75                  80

Lys Ser Ser Gly Ser Asn Ile Trp Arg Thr Gly Phe Thr Thr Asp Ile
            85                  90                  95

Asn Glu Thr Asp Val Val Phe Gly Gly Glu Lys Arg Leu Phe Lys Ser
            100                 105                 110

Ile Lys Glu Ile Ile Glu Lys Tyr Asp Pro Pro Ala Val Phe Val Tyr
        115                 120                 125

Gln Thr Cys Val Pro Ala Met Ile Gly Asp Asp Ile Asp Ala Val Cys
    130                 135                 140

Lys Ala Ala Arg Glu Lys Phe Gly Lys Pro Val Ile Pro Ile Asn Ser
145                 150                 155                 160

Pro Gly Phe Val Gly Pro Lys Asn Leu Gly Asn Lys Leu Ala Gly Glu
            165                 170                 175

Ala Leu Leu Asp His Val Ile Gly Thr Glu Glu Pro Asp Tyr Thr Thr
            180                 185                 190

Ala Tyr Asp Ile Asn Ile Ile Gly Glu Tyr Asn Leu Ser Gly Glu Leu
        195                 200                 205

Trp Gln Val Lys Pro Leu Leu Asp Glu Leu Gly Ile Arg Ile Leu Ala
    210                 215                 220

Cys Ile Ser Gly Asp Gly Lys Tyr Lys Asp Val Ala Ser Ser His Arg
225                 230                 235                 240

Ala Lys Ala Ala Met Met Val Cys Ser Lys Ala Met Ile Asn Val Ala
            245                 250                 255

Arg Lys Met Glu Glu Arg Tyr Asp Ile Pro Phe Phe Glu Gly Ser Phe
            260                 265                 270

Tyr Gly Ile Glu Asp Ser Ser Asp Ser Leu Arg Glu Ile Ala Arg Met
        275                 280                 285

Leu Ile Glu Lys Gly Ala Asp Pro Glu Leu Met Asp Arg Thr Glu Ala
    290                 295                 300

Leu Ile Glu Arg Glu Glu Lys Lys Ala Trp Asp Ala Ile Ala Ala Tyr
305                 310                 315                 320

Lys Pro Arg Phe Lys Asp Lys Lys Val Leu Leu Ile Thr Gly Gly Val
            325                 330                 335

Lys Ser Trp Ser Val Val Ala Ala Leu Gln Glu Ala Gly Leu Glu Leu

-continued

```
                340                 345                 350

Val Gly Thr Ser Val Lys Lys Ser Thr Lys Glu Asp Lys Glu Arg Ile
        355                 360                 365

Lys Glu Leu Met Gly Gln Asp Ala His Met Ile Asp Asp Met Thr Pro
    370                 375                 380

Arg Glu Met Tyr Lys Met Leu Lys Asp Ala Lys Ala Asp Ile Met Leu
385                 390                 395                 400

Ser Gly Gly Arg Ser Gln Phe Ile Ala Leu Lys Ala Ala Met Pro Trp
                405                 410                 415

Leu Asp Ile Asn Gln Glu Arg His His Ala Tyr Met Gly Tyr Val Gly
                420                 425                 430

Met Val Lys Leu Val Glu Glu Ile Asp Lys Ala Leu Tyr Asn Pro Val
            435                 440                 445

Trp Glu Gln Val Arg Lys Pro Ala Pro Trp Glu Asn Pro Glu Asp Thr
        450                 455                 460

Trp Gln Ala Arg Ala Leu Ala Glu Met Glu Ala Glu Ala Ala Ala Leu
465                 470                 475                 480

Ala Ala Asp Pro Val Arg Ala Glu Glu Val Arg Arg Ser Lys Lys Ile
                485                 490                 495

Cys Asn Cys Lys Ser Val Asp Leu Gly Thr Ile Glu Asp Ala Ile Lys
            500                 505                 510

Ala His Ala Leu Thr Thr Val Glu Gly Val Arg Glu His Thr Asn Ala
            515                 520                 525

Ser Gly Gly Cys Gly Ala Cys Ser Gly Arg Ile Glu Glu Ile Phe Glu
        530                 535                 540

Ala Val Gly Val Val Ala Ala Pro Pro Ala Glu Ala Ala Pro Ser
545                 550                 555                 560

Pro Gln Glu Ile Ala Pro Asp Pro Leu Ala Ala Glu Glu Lys Arg Arg
                565                 570                 575

Ala Lys Lys Ala Cys Gly Cys Lys Glu Val Ala Val Gly Thr Ile Glu
                580                 585                 590

Asp Ala Ile Arg Ala Lys Gly Leu Arg Asn Ile Ala Glu Val Arg Ala
            595                 600                 605

Ala Thr Asp Ala Asn Thr Gly Cys Gly Asn Cys Gln Glu Arg Val Glu
        610                 615                 620

Gly Ile Leu Asp Arg Val Leu Ala Glu Ala Ala Ser Glu Leu Gln Ala
625                 630                 635                 640

Ala Glu
```

```
<210> SEQ ID NO 52
<211> LENGTH: 1503
<212> TYPE: DNA
<213> ORGANISM: Unknown
<220> FEATURE:
<223> OTHER INFORMATION: novel strain

<400> SEQUENCE: 52
atgagtgtcg cacagtccca gagcgtcgcc gagatcaagg cgcgcaacaa ggaactcatc      60
gaagaggtcc tcaaggtcta tcccgagaag accgccaagc gccgcgccaa gcacctgaac     120
gtccacgaag ccggcaagtc cgactgcggc gtgaagtcca acatcaagtc catcccgggc     180
gtgatgacca tccgcggttg cgcttatgcc ggctccaagg gtgtggtgtg gggtccatc      240 aaggacatga tccacatctc ccacggcccg gtgggctgcg ccagtatag ctgggccgcc      300 cgccgcaact actatatcgg cacgaccggc atcgacacct tcgtgacgat gcagttcacc     360
```

```
tccgacttcc aggagaagga catcgtcttc ggcggcgaca agaagctcgc caagatcatg     420
gacgagatcc aggagctgtt cccgctgaac aacggcatca ccgttcagtc cgagtgcccc     480
atcggcctca tcggcgacga catcgaggcc gtctccaagc agaagtccaa ggagtatgag     540
ggcaagacca tcgtgccggt cgctgcgag ggcttccgcg gcgtgtccca gtccctgggc     600
caccacatcg ccaacgacgc catccgcgat tgggtgttcg acaagatcgc gcccgacgcc     660
gagccgcgct ttgagccgac cccgtacgac gtcgccatca tcggcgacta caatatcggt     720
ggtgacgcct ggtcgtcccg tatcctcctg gaggagatgg cctgcgcgt gatcgcccag     780 tggtccggcg acggttcgct cgctgagctg gaggccaccc cgaaggccaa gctcaacgtg     840
ctgcactgct accgctccat gaactacatc tcgcgccaca tggaagagaa gtacggtatc     900
ccgtggtgcg agtacaactt cttcggtcct tccaagatcg ccgagtccct cgcgaagatc     960
gccagctact tcgacgacaa gatcaaggaa ggcgcggagc gcgtcatcgc caagtatcag    1020
ccgctcatgg atgcggtgat cgcgaagtat cgtcccgcc tcgagggcaa gaccgtgatg    1080
ctgtacgtgg gcggcctgcg tccccgtcac gtcatcggcg cctacgagga cctgggcatg    1140
gaagtggtcg gcacgggcta cgagttcgcc cataacgacg actaccagcg caccgcccag    1200
cactacgtca aggatggcac catcatctat gacgacgtga ccggctacga gttcgagaag    1260
ttcgtcgaga agatccagcc ggacctggtc ggttcgggca tcaaggaaaa gtacgtcttc    1320
cagaagatgg gcgtgccgtt ccgccagatg cactcctggg actactcggg cccgtaccac    1380
ggctatgacg gcttcgcgat cttcgcgcgc gacatggaca tggccatcaa cagccccgtg    1440
tggaagatga cccaggctcc gtggaagagc gtccccaagc cgacgatgct cgcggctgaa    1500
tga                                                                   1503
```

<210> SEQ ID NO 53
<211> LENGTH: 500
<212> TYPE: PRT
<213> ORGANISM: Unknown
<220> FEATURE:
<223> OTHER INFORMATION: novel strain

<400> SEQUENCE: 53

```
Met Ser Val Ala Gln Ser Gln Ser Val Ala Glu Ile Lys Ala Arg Asn
1               5                   10                  15

Lys Glu Leu Ile Glu Glu Val Leu Lys Val Tyr Pro Glu Lys Thr Ala
            20                  25                  30

Lys Arg Arg Ala Lys His Leu Asn Val His Glu Ala Gly Lys Ser Asp
        35                  40                  45

Cys Gly Val Lys Ser Asn Ile Lys Ser Ile Pro Gly Val Met Thr Ile
        50                  55                  60

Arg Gly Cys Ala Tyr Ala Gly Ser Lys Gly Val Val Trp Gly Pro Ile
65              70                  75                  80

Lys Asp Met Ile His Ile Ser His Gly Pro Val Gly Cys Gly Gln Tyr
                85                  90                  95

Ser Trp Ala Ala Arg Arg Asn Tyr Tyr Ile Gly Thr Thr Gly Ile Asp
            100                 105                 110

Thr Phe Val Thr Met Gln Phe Thr Ser Asp Phe Gln Glu Lys Asp Ile
        115                 120                 125

Val Phe Gly Gly Asp Lys Lys Leu Ala Lys Ile Met Asp Glu Ile Gln
        130                 135                 140

Glu Leu Phe Pro Leu Asn Asn Gly Ile Thr Val Gln Ser Glu Cys Pro
```

-continued

```
145               150               155               160

Ile Gly Leu Ile Gly Asp Asp Ile Glu Ala Val Ser Lys Gln Lys Ser
                165               170               175

Lys Glu Tyr Glu Gly Lys Thr Ile Val Pro Val Arg Cys Glu Gly Phe
                180               185               190

Arg Gly Val Ser Gln Ser Leu Gly His His Ile Ala Asn Asp Ala Ile
                195               200               205

Arg Asp Trp Val Phe Asp Lys Ile Ala Pro Asp Ala Glu Pro Arg Phe
    210               215               220

Glu Pro Thr Pro Tyr Asp Val Ala Ile Ile Gly Asp Tyr Asn Ile Gly
225               230               235               240

Gly Asp Ala Trp Ser Ser Arg Ile Leu Leu Glu Glu Met Gly Leu Arg
                245               250               255

Val Ile Ala Gln Trp Ser Gly Asp Gly Ser Leu Ala Glu Leu Glu Ala
                260               265               270

Thr Pro Lys Ala Lys Leu Asn Val Leu His Cys Tyr Arg Ser Met Asn
                275               280               285

Tyr Ile Ser Arg His Met Glu Glu Lys Tyr Gly Ile Pro Trp Cys Glu
    290               295               300

Tyr Asn Phe Phe Gly Pro Ser Lys Ile Ala Glu Ser Leu Arg Lys Ile
305               310               315               320

Ala Ser Tyr Phe Asp Asp Lys Ile Lys Glu Gly Ala Glu Arg Val Ile
                325               330               335

Ala Lys Tyr Gln Pro Leu Met Asp Ala Val Ile Ala Lys Tyr Arg Pro
                340               345               350

Arg Leu Glu Gly Lys Thr Val Met Leu Tyr Val Gly Gly Leu Arg Pro
                355               360               365

Arg His Val Ile Gly Ala Tyr Glu Asp Leu Gly Met Glu Val Val Gly
    370               375               380

Thr Gly Tyr Glu Phe Ala His Asn Asp Asp Tyr Gln Arg Thr Ala Gln
385               390               395               400

His Tyr Val Lys Asp Gly Thr Ile Ile Tyr Asp Asp Val Thr Gly Tyr
                405               410               415

Glu Phe Glu Lys Phe Val Glu Lys Ile Gln Pro Asp Leu Val Gly Ser
                420               425               430

Gly Ile Lys Glu Lys Tyr Val Phe Gln Lys Met Gly Val Pro Phe Arg
                435               440               445

Gln Met His Ser Trp Asp Tyr Ser Gly Pro Tyr His Gly Tyr Asp Gly
    450               455               460

Phe Ala Ile Phe Ala Arg Asp Met Asp Met Ala Ile Asn Ser Pro Val
465               470               475               480

Trp Lys Met Thr Gln Ala Pro Trp Lys Ser Val Pro Lys Pro Thr Met
                485               490               495

Leu Ala Ala Glu
            500
```

```
<210> SEQ ID NO 54
<211> LENGTH: 1377
<212> TYPE: DNA
<213> ORGANISM: Unknown
<220> FEATURE:
<223> OTHER INFORMATION: novel strain

<400> SEQUENCE: 54
atggccaccg tttccgtctc caagaaggcc tgcgcggtca accccctcaa gatgagccag      60
```

-continued

```
ccggtgggcg gcgcgctcgc cttcatgggc gtgcgcaagg ccatgccgct gctgcacggc        120
tcgcagggct gcacctcctt cggcctggtg ctgttcgtgc gccacttcaa ggaagccatc        180
cccatgcaga ccaccgccat gagcgaggtg gcgacggttc tgggcggcct tgagaatgtg        240
gagcaggcca ttctcaacat ctacaatcgc accaagccgg agatcatcgg catctgctcc        300
accggcgtca ccgagaccaa gggcgatgat gtcgacggct acatcaagct gatccgggac        360
aagtatcccc agctggccga cttcccgctg gtctatgtct ccacccccga tttcaaggac        420
gccttccagg acggttggga agaccgtgcg aagatgg tggaggcgct ggtgaagccc            480
gccgccgaca gcagaagga caagacccgc gtcaacgtcc tgcccggctg ccacctcacg         540
cccggcgatc tggatgagat gcggaccatc ttcgaggatt cgggctcac accctatttc         600 ctgccggatc tggccggctc gctggatggg catatccccg aggacttctc gcccaccacc        660
atcggcggca tcggcatcga tgagatcgcc accatgggcg aggcggccca caccatctgc        720
atcggcgcgc agatgcgccg ggcgggcgag gccatggaga agaagaccgg cattcccttc        780
aagctgttcg agcgcctgtg cggcctggag gcgaacgacg ccttcatcat gcacctgtcg        840
cagatctccg gccggccggt gccggtgaag tatcgccggc agcggggcca gctggtggat        900
gccatgctgg acggccactt ccatctgggc ggtcgcaagg tggccatggg ggcggagccg        960
gacctgctct acgacgtggg ctccttcctg cacgagatgg gcgcccacat cctttccgcg       1020
gtcaccacca cccagtcgcc ggtgctggcg cgcctgcctg ccgaggaggt gcttatcggc       1080
gacctggagg atctggagac ccaggcgaag gcgcgcggat gcgatctcct gctcacccat       1140
tcccatgggc gccaggcggc ggagcgcctc cacatcccct tctaccggat cggcattccc       1200
atgtttgacc ggctggggc gggggcatctg ttgtcggtgg ctatcgcgg cacccgcgac        1260 ctcatcttcc atctcgccaa ccttgtgatc gccgaccacg aggaaaatca cgagccgacg       1320
cccgacacct gggccaccgg ccatggcgag catgccgccg cccccacttc ccattga         1377
```

<210> SEQ ID NO 55
<211> LENGTH: 458
<212> TYPE: PRT
<213> ORGANISM: Unknown
<220> FEATURE:
<223> OTHER INFORMATION: novel strain

<400> SEQUENCE: 55

```
Met Ala Thr Val Ser Val Ser Lys Lys Ala Cys Ala Val Asn Pro Leu
1               5                   10                  15

Lys Met Ser Gln Pro Val Gly Gly Ala Leu Ala Phe Met Gly Val Arg
            20                  25                  30

Lys Ala Met Pro Leu Leu His Gly Ser Gln Gly Cys Thr Ser Phe Gly
        35                  40                  45

Leu Val Leu Phe Val Arg His Phe Lys Glu Ala Ile Pro Met Gln Thr
    50                  55                  60

Thr Ala Met Ser Glu Val Ala Thr Val Leu Gly Gly Leu Glu Asn Val
65                  70                  75                  80

Glu Gln Ala Ile Leu Asn Ile Tyr Asn Arg Thr Lys Pro Glu Ile Ile
                85                  90                  95

Gly Ile Cys Ser Thr Gly Val Thr Glu Thr Lys Gly Asp Asp Val Asp
            100                 105                 110

Gly Tyr Ile Lys Leu Ile Arg Asp Lys Tyr Pro Gln Leu Ala Asp Phe
        115                 120                 125
```

```
Pro Leu Val Tyr Val Ser Thr Pro Asp Phe Lys Asp Ala Phe Gln Asp
    130                 135                 140

Gly Trp Glu Lys Thr Val Ala Lys Met Val Glu Ala Leu Val Lys Pro
145                 150                 155                 160

Ala Ala Asp Lys Gln Lys Asp Lys Thr Arg Val Asn Val Leu Pro Gly
                165                 170                 175

Cys His Leu Thr Pro Gly Asp Leu Asp Glu Met Arg Thr Ile Phe Glu
                180                 185                 190

Asp Phe Gly Leu Thr Pro Tyr Phe Leu Pro Asp Leu Ala Gly Ser Leu
                195                 200                 205

Asp Gly His Ile Pro Glu Asp Phe Ser Pro Thr Thr Ile Gly Gly Ile
    210                 215                 220

Gly Ile Asp Glu Ile Ala Thr Met Gly Glu Ala Ala His Thr Ile Cys
225                 230                 235                 240

Ile Gly Ala Gln Met Arg Arg Ala Gly Glu Ala Met Glu Lys Lys Thr
                245                 250                 255

Gly Ile Pro Phe Lys Leu Phe Glu Arg Leu Cys Gly Leu Glu Ala Asn
                260                 265                 270

Asp Ala Phe Ile Met His Leu Ser Gln Ile Ser Gly Arg Pro Val Pro
                275                 280                 285

Val Lys Tyr Arg Arg Gln Arg Gly Gln Leu Val Asp Ala Met Leu Asp
    290                 295                 300

Gly His Phe His Leu Gly Gly Arg Lys Val Ala Met Gly Ala Glu Pro
305                 310                 315                 320

Asp Leu Leu Tyr Asp Val Gly Ser Phe Leu His Glu Met Gly Ala His
                325                 330                 335

Ile Leu Ser Ala Val Thr Thr Thr Gln Ser Pro Val Leu Ala Arg Leu
                340                 345                 350

Pro Ala Glu Glu Val Leu Ile Gly Asp Leu Glu Asp Leu Glu Thr Gln
                355                 360                 365

Ala Lys Ala Arg Gly Cys Asp Leu Leu Leu Thr His Ser His Gly Arg
    370                 375                 380

Gln Ala Ala Glu Arg Leu His Ile Pro Phe Tyr Arg Ile Gly Ile Pro
385                 390                 395                 400

Met Phe Asp Arg Leu Gly Ala Gly His Leu Leu Ser Val Gly Tyr Arg
                405                 410                 415

Gly Thr Arg Asp Leu Ile Phe His Leu Ala Asn Leu Val Ile Ala Asp
                420                 425                 430

His Glu Glu Asn His Glu Pro Thr Pro Asp Thr Trp Ala Thr Gly His
                435                 440                 445

Gly Glu His Ala Ala Ala Pro Thr Ser His
    450                 455
```

```
<210> SEQ ID NO 56
<211> LENGTH: 1560
<212> TYPE: DNA
<213> ORGANISM: Unknown
<220> FEATURE:
<223> OTHER INFORMATION: novel strain

<400> SEQUENCE: 56
atgccacaaa atgctgacaa tgtgctcgat cacttcgagc tcttccgtgg tcccgaatac        60
cagcagatgc tggccaataa gaaaaagatg ttcgagaacc cccgcgatcc ggccgaagtc       120
gagcgcgtgc gggaatgggc gaagactcct gaatacaagg agctgaactt cgcccgcgag       180
```

```
gcgctcaccg tgaatccggc caaggcttgt cagccgctgg gcgcggtgtt cgtcgccgtc        240
ggcttcgaga gcacgatccc cttcgtgcac ggctcgcagg gttgcgtcgc gtattaccgc        300
tcgcacctct cccgccactt caaggagccg tcctcctgcg tctcctcgtc catgaccgag        360
gatgcggcgg tgttcggcgg cctcaacaac atgattgacg gcctcgccaa cacctacaac        420
atgtacaagc cgaagatgat cgccgtctcc accacctgca tggcggaagt catcggcgac        480
gatctgaacg ccttcatcaa gaccgcgaag gaaaagggct cggttccggc cgaatacgac        540
gtgcccttcg cccacacccc ggcgttcgtc ggcagccatg tcaccggcta cgacaatgcg        600
ctcaagggca tcctcgagca cttctgggac ggcaaggccg gcaccgcgcc gaagctggag        660
cgcgttccca acgagaagat caacttcatc ggcggcttcg acggctacac cgtcggcaac        720
actcgcgaag tgaagcgcat cttcgaggcg ttcggcgccg attacaccat cctcgccgac        780
aattccgaag tgttcgacac cccgaccgac ggcgagttcc gcatgtatga cggcggcacg        840
accctggagg acgcggcgaa cgcggtgcac gccaaggcca ccatctccat gcaggaatac        900
tgcacggaga agaccctgcc catgatcgcc ggtcatggcc aggacgtggt cgccctcaac        960
caccccgtgg gcgtgggcgg caccgacaag ttcctcatgg agatcgcccg cctcaccggc        1020
aaggagatcc ccgaggagct gacccgcgag cgcgggccgtc tcgtggacgc tatcgcggac        1080
tcttccgcgc acatccacgg caagaagttc gccatctacg gcgatccgga tctgtgcctg        1140
ggcctcgccg cgttcctgct ggagctgggc gccgagccga cccatgtgct ggccaccaac        1200
ggcaccaaga gtgggccga gaaggttcag gaactgttcg actcttcgcc gttcggcgcc        1260
aactgcaagg tctatcccgg caaggacctg tggcacatgc gctcgctcct gttcgtggag        1320
ccggtggatt tcatcatcgg caacacctac ggcaagtatc tcgagcgcga cacgggcacc        1380
ccgctgatcc gtatcggctt cccggtgttc gaccgtcacc accaccaccg ccgtccggtg        1440
tggggctatc agggcggcat gaacgtcctg atcacgatcc tcgacaagat ctttgacgag        1500
atcgaccgca acaccaacgt gccggccaag accgactact cgttcgacat cattcgttga        1560
```

<210> SEQ ID NO 57
<211> LENGTH: 519
<212> TYPE: PRT
<213> ORGANISM: Unknown
<220> FEATURE:
<223> OTHER INFORMATION: novel strain

<400> SEQUENCE: 57

```
Met Pro Gln Asn Ala Asp Asn Val Leu Asp His Phe Glu Leu Phe Arg
1               5                   10                  15

Gly Pro Glu Tyr Gln Gln Met Leu Ala Asn Lys Lys Lys Met Phe Glu
                20                  25                  30

Asn Pro Arg Asp Pro Ala Glu Val Glu Arg Val Arg Glu Trp Ala Lys
            35                  40                  45

Thr Pro Glu Tyr Lys Glu Leu Asn Phe Ala Arg Glu Ala Leu Thr Val
        50                  55                  60

Asn Pro Ala Lys Ala Cys Gln Pro Leu Gly Ala Val Phe Val Ala Val
65                  70                  75                  80

Gly Phe Glu Ser Thr Ile Pro Phe Val His Gly Ser Gln Gly Cys Val
                85                  90                  95

Ala Tyr Tyr Arg Ser His Leu Ser Arg His Phe Lys Glu Pro Ser Ser
                100                 105                 110

Cys Val Ser Ser Ser Met Thr Glu Asp Ala Ala Val Phe Gly Gly Leu
                115                 120                 125
```

```
Asn Asn Met Ile Asp Gly Leu Ala Asn Thr Tyr Asn Met Tyr Lys Pro
    130             135             140
```

```
Lys Met Ile Ala Val Ser Thr Thr Cys Met Ala Glu Val Ile Gly Asp
145             150             155             160
```

```
Asp Leu Asn Ala Phe Ile Lys Thr Ala Lys Glu Lys Gly Ser Val Pro
            165             170             175
```

```
Ala Glu Tyr Asp Val Pro Phe Ala His Thr Pro Ala Phe Val Gly Ser
            180             185             190
```

```
His Val Thr Gly Tyr Asp Asn Ala Leu Lys Gly Ile Leu Glu His Phe
            195             200             205
```

```
Trp Asp Gly Lys Ala Gly Thr Ala Pro Lys Leu Glu Arg Val Pro Asn
    210             215             220
```

```
Glu Lys Ile Asn Phe Ile Gly Gly Phe Asp Gly Tyr Thr Val Gly Asn
225             230             235             240
```

```
Thr Arg Glu Val Lys Arg Ile Phe Glu Ala Phe Gly Ala Asp Tyr Thr
            245             250             255
```

```
Ile Leu Ala Asp Asn Ser Glu Val Phe Asp Thr Pro Thr Asp Gly Glu
            260             265             270
```

```
Phe Arg Met Tyr Asp Gly Gly Thr Thr Leu Glu Asp Ala Ala Asn Ala
            275             280             285
```

```
Val His Ala Lys Ala Thr Ile Ser Met Gln Glu Tyr Cys Thr Glu Lys
    290             295             300
```

```
Thr Leu Pro Met Ile Ala Gly His Gly Gln Asp Val Val Ala Leu Asn
305             310             315             320
```

```
His Pro Val Gly Val Gly Gly Thr Asp Lys Phe Leu Met Glu Ile Ala
            325             330             335
```

```
Arg Leu Thr Gly Lys Glu Ile Pro Glu Glu Leu Thr Arg Glu Arg Gly
            340             345             350
```

```
Arg Leu Val Asp Ala Ile Ala Asp Ser Ser Ala His Ile His Gly Lys
            355             360             365
```

```
Lys Phe Ala Ile Tyr Gly Asp Pro Asp Leu Cys Leu Gly Leu Ala Ala
    370             375             380
```

```
Phe Leu Leu Glu Leu Gly Ala Glu Pro Thr His Val Leu Ala Thr Asn
385             390             395             400
```

```
Gly Thr Lys Lys Trp Ala Glu Lys Val Gln Glu Leu Phe Asp Ser Ser
            405             410             415
```

```
Pro Phe Gly Ala Asn Cys Lys Val Tyr Pro Gly Lys Asp Leu Trp His
            420             425             430
```

```
Met Arg Ser Leu Leu Phe Val Glu Pro Val Asp Phe Ile Ile Gly Asn
    435             440             445
```

```
Thr Tyr Gly Lys Tyr Leu Glu Arg Asp Thr Gly Thr Pro Leu Ile Arg
    450             455             460
```

```
Ile Gly Phe Pro Val Phe Asp Arg His His His Arg Arg Pro Val
465             470             475             480
```

```
Trp Gly Tyr Gln Gly Gly Met Asn Val Leu Ile Thr Ile Leu Asp Lys
            485             490             495
```

```
Ile Phe Asp Glu Ile Asp Arg Asn Thr Asn Val Pro Ala Lys Thr Asp
            500             505             510
```

```
Tyr Ser Phe Asp Ile Ile Arg
            515
```

<210> SEQ ID NO 58
<211> LENGTH: 621

```
<212> TYPE: DNA
<213> ORGANISM: Unknown
<220> FEATURE:
<223> OTHER INFORMATION: novel strain

<400> SEQUENCE: 58
gtggagtccg gtggtcctga gccgggcgtg ggctgcgccg gccgcggcgt gatcacctcc      60
atcaacttcc tggaggagaa cggcgcctac gaggacatcg actatgtgtc ctacgacgtg     120
ctgggcgacg tggtgtgcgg cggcttcgcc atgcccatcc gcgagaacaa ggcgcaggaa     180
atctacatcg tgatgtccgg cgagatgatg gccatgtatg cggccaacaa catctccaag     240
ggcatcctga gtatgccaa ttccggcggc gtgcgcctgg gcgggctggt ctgcaacgag      300
cgccagaccg acaaggagct ggagctggcg gaggctctgg cgaagaagct cggcaccgag     360
ctgatctact tcgtgccgcg cgacaacatc gtgcagcatg ccgagctgcg ccgcatgaca     420
gtgatcgagt atgcgcccga ttccgcccag gcccagcact accggaacct ggccgagaag     480
gtgcacgcca acaagggcaa cggcatcatc ccgaccccga tcaccatgga cgagctggaa     540
gacatgctca tggagcacgg catcatgaag gccgtggacg agagccagat cggcaagacc     600
gccgccgagc tcgccgtctg a                                              621

<210> SEQ ID NO 59
<211> LENGTH: 206
<212> TYPE: PRT
<213> ORGANISM: Unknown
<220> FEATURE:
<223> OTHER INFORMATION: novel strain

<400> SEQUENCE: 59

Met Glu Ser Gly Gly Pro Glu Pro Gly Val Gly Cys Ala Gly Arg Gly
1               5                   10                  15

Val Ile Thr Ser Ile Asn Phe Leu Glu Glu Asn Gly Ala Tyr Glu Asp
            20                  25                  30

Ile Asp Tyr Val Ser Tyr Asp Val Leu Gly Asp Val Val Cys Gly Gly
        35                  40                  45

Phe Ala Met Pro Ile Arg Glu Asn Lys Ala Gln Glu Ile Tyr Ile Val
    50                  55                  60

Met Ser Gly Glu Met Met Ala Met Tyr Ala Ala Asn Asn Ile Ser Lys
65                  70                  75                  80

Gly Ile Leu Lys Tyr Ala Asn Ser Gly Gly Val Arg Leu Gly Gly Leu
                85                  90                  95

Val Cys Asn Glu Arg Gln Thr Asp Lys Glu Leu Glu Leu Ala Glu Ala
            100                 105                 110

Leu Ala Lys Lys Leu Gly Thr Glu Leu Ile Tyr Phe Val Pro Arg Asp
            115                 120                 125

Asn Ile Val Gln His Ala Glu Leu Arg Arg Met Thr Val Ile Glu Tyr
        130                 135                 140

Ala Pro Asp Ser Ala Gln Ala Gln His Tyr Arg Asn Leu Ala Glu Lys
145                 150                 155                 160

Val His Ala Asn Lys Gly Asn Gly Ile Ile Pro Thr Pro Ile Thr Met
                165                 170                 175

Asp Glu Leu Glu Asp Met Leu Met Glu His Gly Ile Met Lys Ala Val
            180                 185                 190

Asp Glu Ser Gln Ile Gly Lys Thr Ala Ala Glu Leu Ala Val
        195                 200                 205
```